United States Patent
Bryant et al.

(10) Patent No.: US 8,257,367 B2
(45) Date of Patent: Sep. 4, 2012

(54) SURGICAL CABLE TENSIONING APPARATUS AND METHOD

(75) Inventors: Mark A. Bryant, Auburn, IN (US); Richard A. Lane, Fort Wayne, IN (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 303 days.

(21) Appl. No.: 12/540,303

(22) Filed: Aug. 12, 2009

(65) Prior Publication Data

US 2010/0042106 A1 Feb. 18, 2010

Related U.S. Application Data

(60) Provisional application No. 61/088,078, filed on Aug. 12, 2008.

(51) Int. Cl.
*A61B 17/10* (2006.01)
(52) U.S. Cl. .................................................. 606/140
(58) Field of Classification Search ............. 606/86 A, 606/99, 103, 138–141, 144, 148, 263, 86 R
See application file for complete search history.

(56) References Cited

U.S. PATENT DOCUMENTS

| | | | |
|---|---|---|---|
| 4,966,600 A | 10/1990 | Songer et al. | |
| 5,116,340 A | 5/1992 | Songer et al. | |
| 5,312,410 A | 5/1994 | Miller et al. | |
| 5,395,374 A | 3/1995 | Miller et al. | |
| 5,415,658 A | 5/1995 | Kilpela et al. | |
| 5,649,927 A | 7/1997 | Kilpela et al. | |
| 5,741,260 A | 4/1998 | Songer et al. | |
| 5,788,697 A | 8/1998 | Kilpela et al. | |
| 5,935,130 A | 8/1999 | Kilpela et al. | |
| 6,146,386 A * | 11/2000 | Blackman et al. | 606/103 |
| 6,364,885 B1 | 4/2002 | Kilpela et al. | |
| 6,595,994 B2 | 7/2003 | Kilpela et al. | |
| 6,605,091 B1 | 8/2003 | Iwanski | |
| 6,689,140 B2 * | 2/2004 | Cohen | 606/103 |
| 7,207,993 B1 | 4/2007 | Baldwin et al. | |
| 2002/0058943 A1 | 5/2002 | Kilpela et al. | |
| 2005/0055041 A1 | 3/2005 | Woods | |
| 2006/0229623 A1 | 10/2006 | Bonutti et al. | |
| 2006/0235401 A1 | 10/2006 | Baldwin et al. | |
| 2008/0312705 A1 * | 12/2008 | Schneid et al. | 606/86 R |
| 2009/0082821 A1 * | 3/2009 | Konno et al. | 606/86 A |
| 2009/0138048 A1 * | 5/2009 | Baccelli et al. | 606/263 |

* cited by examiner

*Primary Examiner* — Eduardo C Robert
*Assistant Examiner* — Atiya Mahmud
(74) *Attorney, Agent, or Firm* — Fitch, Even, Tabin & Flannery, LLP

(57) ABSTRACT

A cable tensioning apparatus and method are provided for positioning and tensioning a surgical cable to skeletal tissue or to implants. The invention is most applicable for securing surgical cable and/or orthopedic implants to bone in orthopedic surgery. A linearly translated drive rod attached to cable is driven by a friction drive to create tension on the surgical cable.

8 Claims, 83 Drawing Sheets

2001

3601

SURGICAL CABLE TENSIONING APPARATUS AND METHOD

RELATED APPLICATIONS

This application claims priority to U.S. Provisional Application No. 61/088,078, filed Aug. 12, 2008, the contents of which are hereby incorporated by reference herein in their entirety.

FIELD OF THE INVENTION

This invention pertains generally to surgical methods and apparatus for tensioning cables or wires. More specifically, the invention relates to methods and apparatus for securing cable and/or orthopedic implants to bone or skeletal tissue in orthopedic surgery through the use of cables or wires.

BACKGROUND

Surgical cables and wires are used extensively in orthopedic surgery for securing bones and bone fragments in place and for fastening surgical implants to bones. In the most common type of orthopedic surgery where severe breaks of bones have taken place, or in reconstructive procedures on bones, for example in reconstructive hip procedures or the like, a permanent cable implant is provided to hold bone portions together. For example, during a total hip replacement, press-fit femoral components are inserted into the canal of the femur, resulting in an extremely tight fit in some cases. Seating of these press-fit components has been shown to induce large hoop stresses in the proximal femur, which can result in longitudinal cracks in the femur. Thus, a surgical cable system is applied for providing a counteracting compressive hoop stress, which prevents crack formation and/or propagation.

Typically, surgical cables are implanted using tensioning devices, which apply tension to a cable looped around the bone and the cable implant. The cables are typically formed into a loop, simple or complex, and tightened about the bone structure and implant with a tensioning tool.

These tensioning tools are often cumbersome due to the strength required to support the device while creating high tensile forces in the surgical cables. Cable tensioning tools are also extremely slow to operate because of threaded drives used to create the large tensile forces in the surgical cable. The slow operation of cable tensioners can cause significant delays in the surgery itself. Any delays in surgery prolong the time required for the patient to be under general anesthetic increasing the risk of complications and recovery time of the patient.

Finally, many cable tensioning tools are long and narrow in which cable is thread blindly through the device. These cable tensioning tools are extremely complicated and difficult to operate under the stress and time constraint of surgery especially during trauma cases. Furthermore, complicated mechanisms have an increased likelihood of mechanical malfunctioning, i.e. jamming, and the restoration of function is extremely difficult due to the blind threading of cable in the devices.

One example is shown in U.S. Pat. No. 5,312,410 filed Dec. 7, 1992 to Miller et al. In the Miller example, a rudimentary ratchet mechanism is used to create cable tension thread blindly through the device. The ratchet mechanism causes force to be transmitted from a lever directly to the ratchet teeth of the device causing shock waves from the intermittent motion and imprecise positioning of tensioned cable due to mechanical backlash. The imprecise positioning of the device can cause imprecise tensioning in the attached cable and could further damage the patient's fragile bones.

Another example is shown in U.S. Patent Application Pub. No. US 2006/0229623 A1 filed Feb. 21, 2006 to Bonutti et al. In the Bonutti example, the pistol grip is used only to crimp the cable and the proximal lever is used to actually tension the cable. The Bonutti example requires wrapping the cable around a cylinder by hand and awkwardly rotating the lever to achieve a small amount of cable being drawn through the instrument. Such awkward operation of medical instruments is not intuitive to medical personnel unfamiliar with complicated mechanical systems.

SUMMARY

In accordance with the present invention, the pistol grip tensioning device provides a significantly improved apparatus for tensioning cable used to secure skeletal tissue or bones in orthopedic surgery developed from insights gained by surgeons' experience in the operating room. The pistol grip tensioning device apparatus provides a surgeon all the components to tension surgical cable, but in a more ergonomic and easier to use assembly than conventional cable tensioners.

The rear or proximal cable clamp assemblies lock surgical cable without damaging or deforming the cable as other conventional clamps. The cable attached to the cable clamp assembly is driven away from the patient by a simple drive rod to create tension on the cable around the bone. The drive rod is in turn driven by a surgeon squeezing a handle and lever together to operate the pistol grip tensioner. The surgeon can easily read the amount of tension created by the cable on the bone by reading a gauge or tension indicator integral to the tensioner to prevent over-tightening the cable and potential damage to the patient's bone. An additional cable clamp assembly is located on the tip or distal end of the cable tensioner to allow any amount of cable to be drawn under tension by the device. The distal cable clamp assembly can be used with the proximal cable clamp assembly to draw any length of cable with great force created by the mechanical advantage created by the drive mechanism and mechanical leverage.

In one form, the drive mechanism operates by a canting member fitting around the drive rod that mechanically engages or locks on to the rod, i.e. a friction drive. The drive rod is driven by the force of the surgeon squeezing the grips which is multiplied and transmitted by the drive mechanism on to the rod. A release mechanism allows the surgeon to repeat squeezing of the grips for the rod to travel farther without the rod slipping on the canting member under tension. The release mechanism, in the form of a simple lever or trigger, allows the drive rod to be reset to the initial position simply by pressing the lever of the trigger to draw more length of cable.

In one embodiment, the cable passes through cable clamp assemblies that are offset to the body of the cable tensioning apparatus to allow tactile and visual feedback as to the position of the cable in the tensioning apparatus. The offset cable clamp assemblies also allow manual adjustment and improved visualization of the cable tensioning process. In another embodiment, the cable passes through a central passage or bore to allow smoother mechanical operation and higher loading.

The cable tensioning apparatus may have ducts or flow ports located within the housing to allow cleaning. The ducts or flow ports allow cleaning solutions to flush out and clean all of the internal mechanisms of the cable tensioning apparatus. The cable tensioning apparatus is also modularly designed to allow the apparatus to easily be assembled and disassembled to further aid the cleaning of the apparatus.

One advantage of the cable tensioning apparatus is the cleanability of the cable tensioning apparatus. Cleanability reduces the risk of infection to patients due to cross contamination of biologic materials from patient to patient after repeated uses of the tensioning apparatus. The risk of infection is minimized because of the ease of disassembly and ease of access of internal component through ducts or flow ports throughout the device to allow high pressure flushing of the cable tensioning apparatus. The offset cable clamp assemblies further assist in cleanability because most of the cable passes externally with open access for cleaning.

Another advantage of the cable tensioning apparatus is the rapidity in which surgical cable can be drawn and tensioned. The ability to quickly tension multiple surgical cables used in the typical surgical procedure multiplies the speed in which the surgery itself is performed. In addition, surgical cable can be rapidly "pre-tensioned" to eliminate any slack in the cable to greatly increase the pace of the surgery itself. Any reduction of the time of the surgery is a great benefit because the reduction of the time that the patient is under anesthetic also reduces the risk of infection, the risk of complications from the anesthetic itself, and the recovery time of the patient.

One other advantage of the pistol grip cable tensioning apparatus is the simplicity of operation of the arrangement of basic parts that gives surgeons and medical technicians an intuitive understanding of the operation of the device. The device is intuitive because the operator can see and feel how the device is operating, i.e. tactile and visual feedback. Almost no training is required by medical personnel unlike complex cable tensioning systems. The elegant simplicity of the intuitive components created an unpredicted synergy that led to the rapid learning and adoption by surgeons and technicians of the apparatus without the usual lengthy learning period.

Another advantage of the elegant simplicity from the limited number of mechanical elements is the improved reliability because there are not numerous complex mechanisms, any of which can malfunction under slight deviation from ideal conditions. In addition, the limited number of mechanical elements also reduces the weight and the bulk of the device. The superior overall operation of the cable tensioning apparatus by surgeons in the operating room was unpredicted given the simplicity of the design because of the tactile nature of most surgeons.

Another advantage of the cable tensioning apparatus is the accuracy of the cable tensioning apparatus created by the friction drive. The accuracy is an advantage because a precise amount of tension needs to be applied on the cable. Tension needs to be applied to the surgical cable with surgical precision to prevent the cable, which is typically wrapped around fractured bone, from cutting into the fragile bone of the patient or further fracturing the bone. The extremely smooth and precise motion of the friction drive allows a precise amount of tension to be applied by the friction drive and monitored by the tension indicator. The precision is improved because of the virtual elimination of backlash, i.e. the amount of clearance between mated gear teeth such as on a ratchet. The precision of which tension can be applied to cable is a significant improvement over other cable tensioning mechanisms.

Additional advantages and features of the invention will become apparent from the following description and attached claims taken in combination with the accompanying drawings.

DETAILED DESCRIPTION

Figure 1:
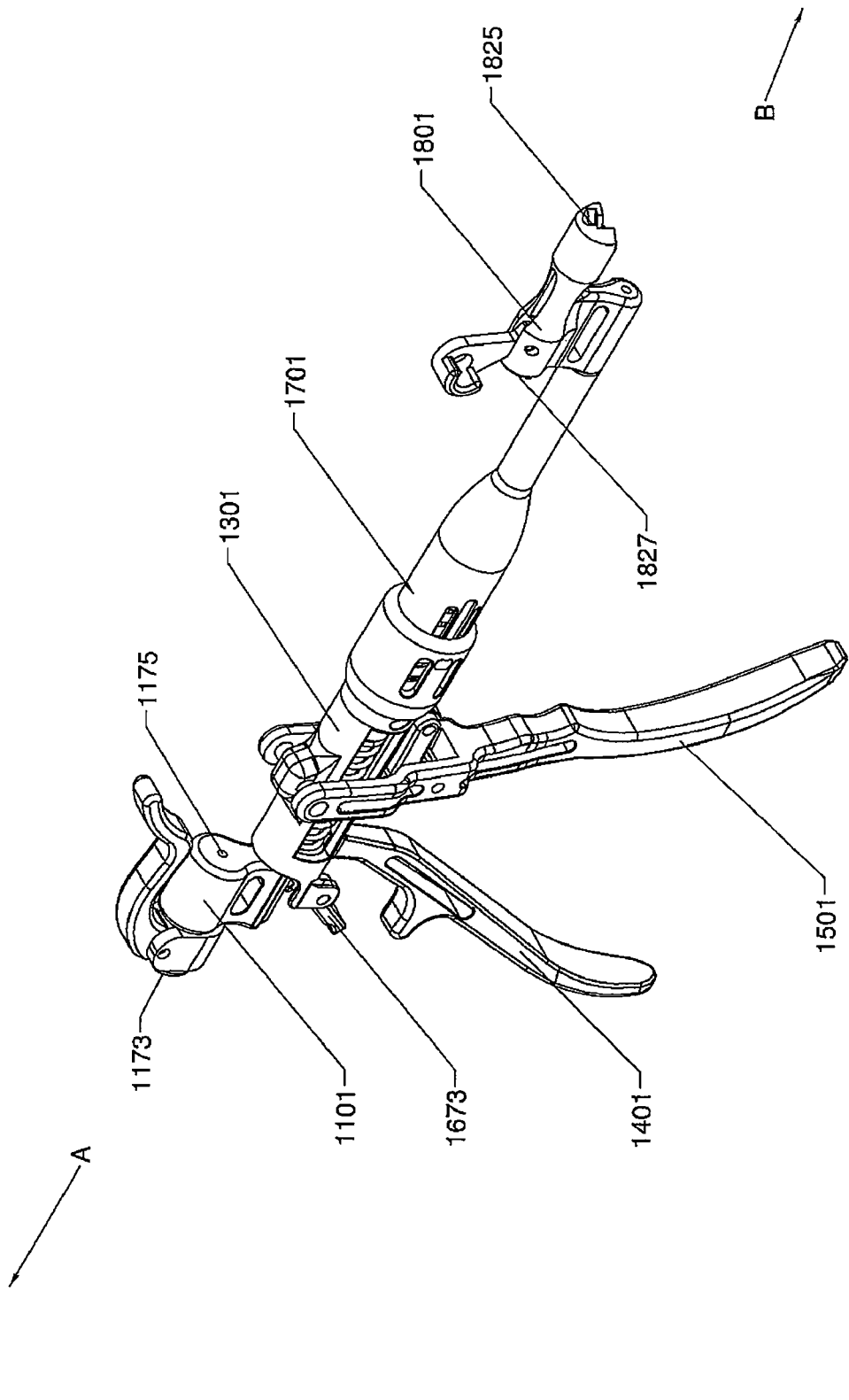
FIG. 1 is an isometric view of the first embodiment of the pistol grip tensioning apparatus in the initial condition.

The following location and direction convention will be used throughout all the described drawings and their written descriptions. In describing the pistol grip cable tensioning device or apparatus of the present invention, the term "proximal" refers to a direction of the device away from the patient and rearwardly towards the user while the term "distal" refers to a direction of the instrument forwardly towards the patient and away from the user. As shown in FIG. 1, the "proximal end" of the insertion apparatus 1001 is shown on the upper left side of the figure near the proximal cable clamp assembly 1101. The "proximal direction" is referring to any motion toward the user and in FIG. 1 is toward the upper left shown as direction A. The "distal end" of the cable tensioning apparatus 1001 is shown on the lower right side of FIG. 1 near the distal cable clamp assembly 1801. The "distal direction" is referring to any motion toward the patient and in FIG. 1 is toward the lower right in direction B.

Cable Tensioning Apparatus Embodiments

Figure 83:
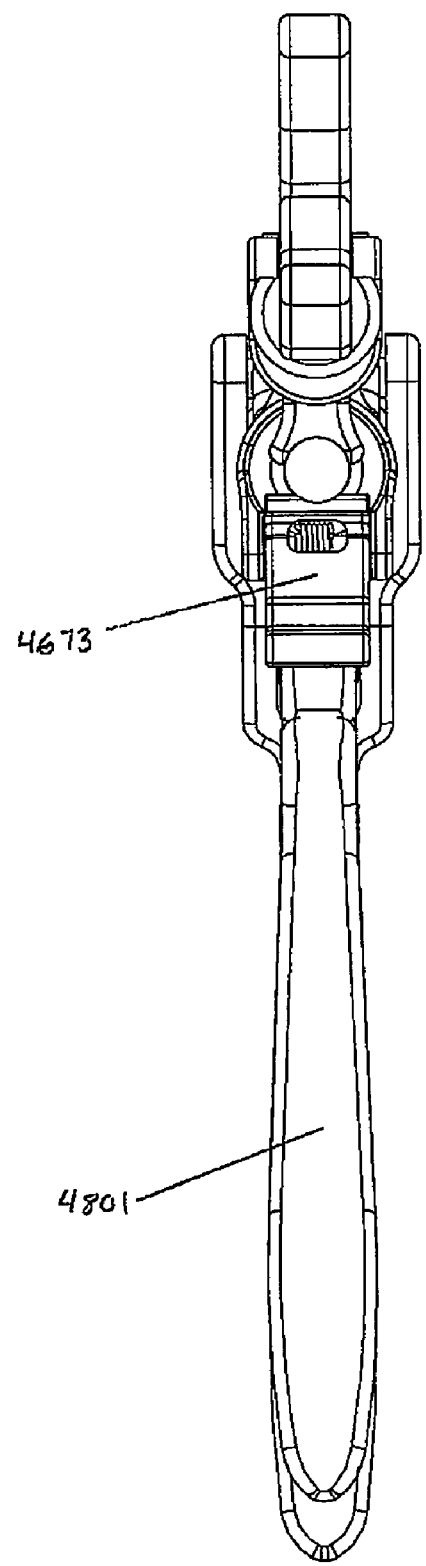
FIG. 83 is a left side view of the fourth embodiment of the pistol grip tensioning apparatus in the initial condition.

The cable tensioning apparatus has four embodiments shown in FIGS. 1 through 83. The first embodiment of the cable tensioning apparatus 1001 is shown in FIG. 1 through FIG. 23. This first apparatus 1001 is operated only by the depression of the lever 1501 causing lever shifts or strokes and is hereinafter referred to as a single action drive. The first embodiment 1001 also has offset cable clamp assemblies 1101, and 1801.

The second cable tensioning apparatus embodiment 2001 is shown in FIG. 24 through FIG. 44. This second apparatus 2001 is again single action, but with centrally aligned located cable clamp assemblies 2101, and 2801.

The third cable tensioning apparatus 3001 is shown in FIG. 52 through FIG. 67. This third apparatus 3001 is actuated by the depression of the lever 3501 in conjunction with the handle 3401 causing handle shifts or strokes and is hereinafter referred to as a double action drive. The third apparatus 3001 also has offset cable clamp assemblies 3101, and 3801.

The fourth cable tensioning apparatus embodiment 4001 is shown in FIG. 68 through FIG. 83. This fourth embodiment 4001 is again single action, but again with offset cable clamp assemblies 4101, and 4801. The fourth embodiment 4001 also has a centrally located bearing 4313 made of polyaryletheretherketone (hereinafter PEEK), as will be described further hereinafter. In addition, the fourth apparatus 4001 has an alternative distal cable clamp assembly 4801 that is configured to allow for access to otherwise inaccessible surgical sites. It is contemplated that the single and double action drive mechanisms can be interchanged as well as a variety of offset and centrally located cable clamp assemblies.

Ergonomic Design and Operation

The cable tensioning apparatuses 1001, 2001, 3001 and 4001 have ergonomically designed levers 1501, 2501, 3501 and 4501 and handles 1401, 2401, 3401 and 4401 to assist the typically gloved hand of the surgeon. The handle/lever combination allows for application of significant tensile force to the surgical cable 12 with direct visual and tactile feedback to the operator as to the progress of the tensioning. For example, the handle/lever combination in the first embodiment provides easy to grip surfaces 1403 and 1503, shown in FIG. 7, for reliable operation of the device when the apparatus 1001 is inevitably soiled by biologic fluids. The ergonomic design is a significant improvement in cable tensioning tools that are operated with slick gloved hands under the stress of surgery. Alternatively, the handle gripping surface 1403 and lever gripping surface 1503 are knurled for any of the embodiments. The cable tensioning apparatus 1001, 2001, 3001 and 4001 is alternatively provided with other surface treatments to improve the grip of the apparatus.

Figure 2:
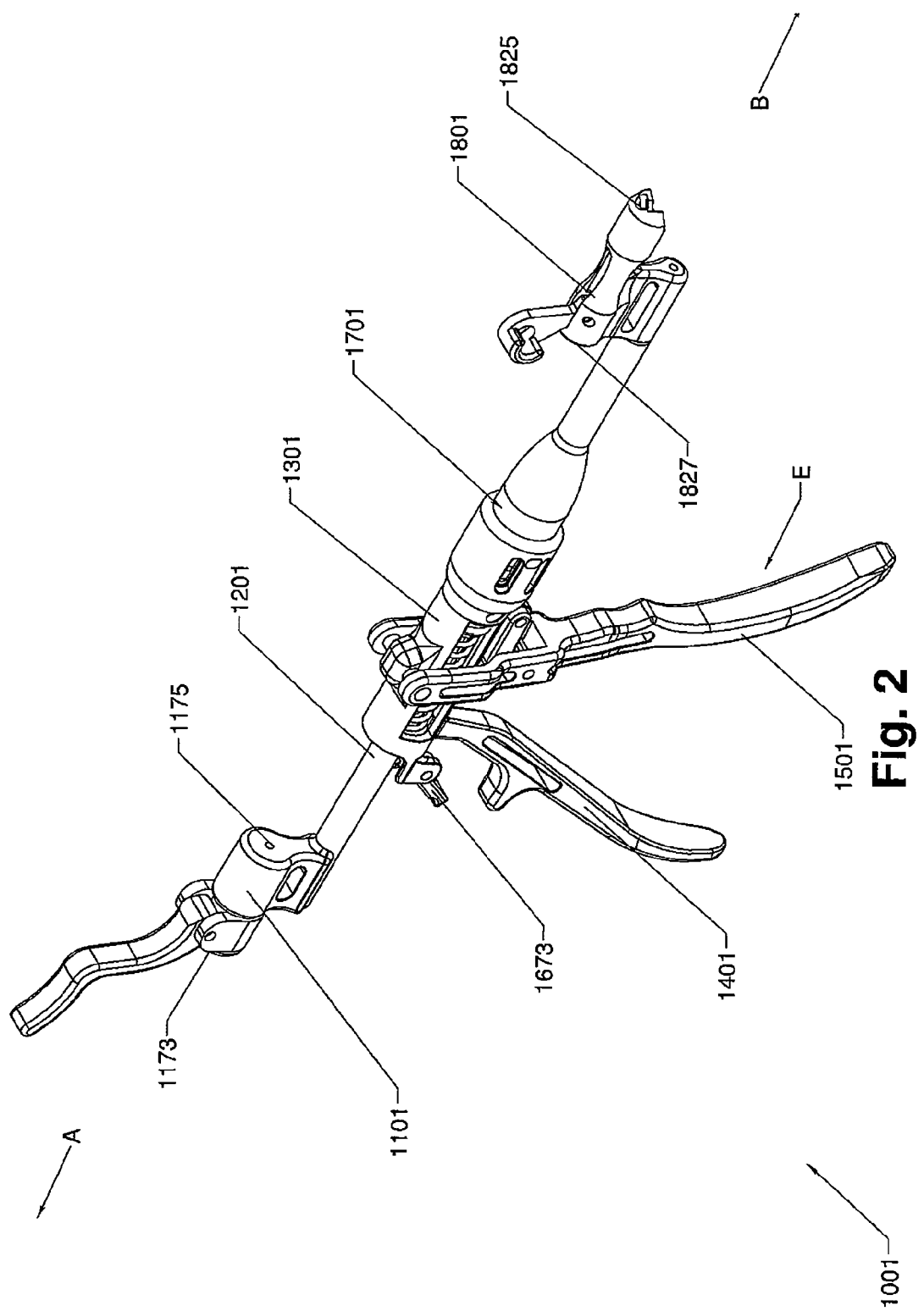
FIG. 2 is an isometric view of the first embodiment of the pistol grip tensioning apparatus in the fully extended condition.
Figure 3:
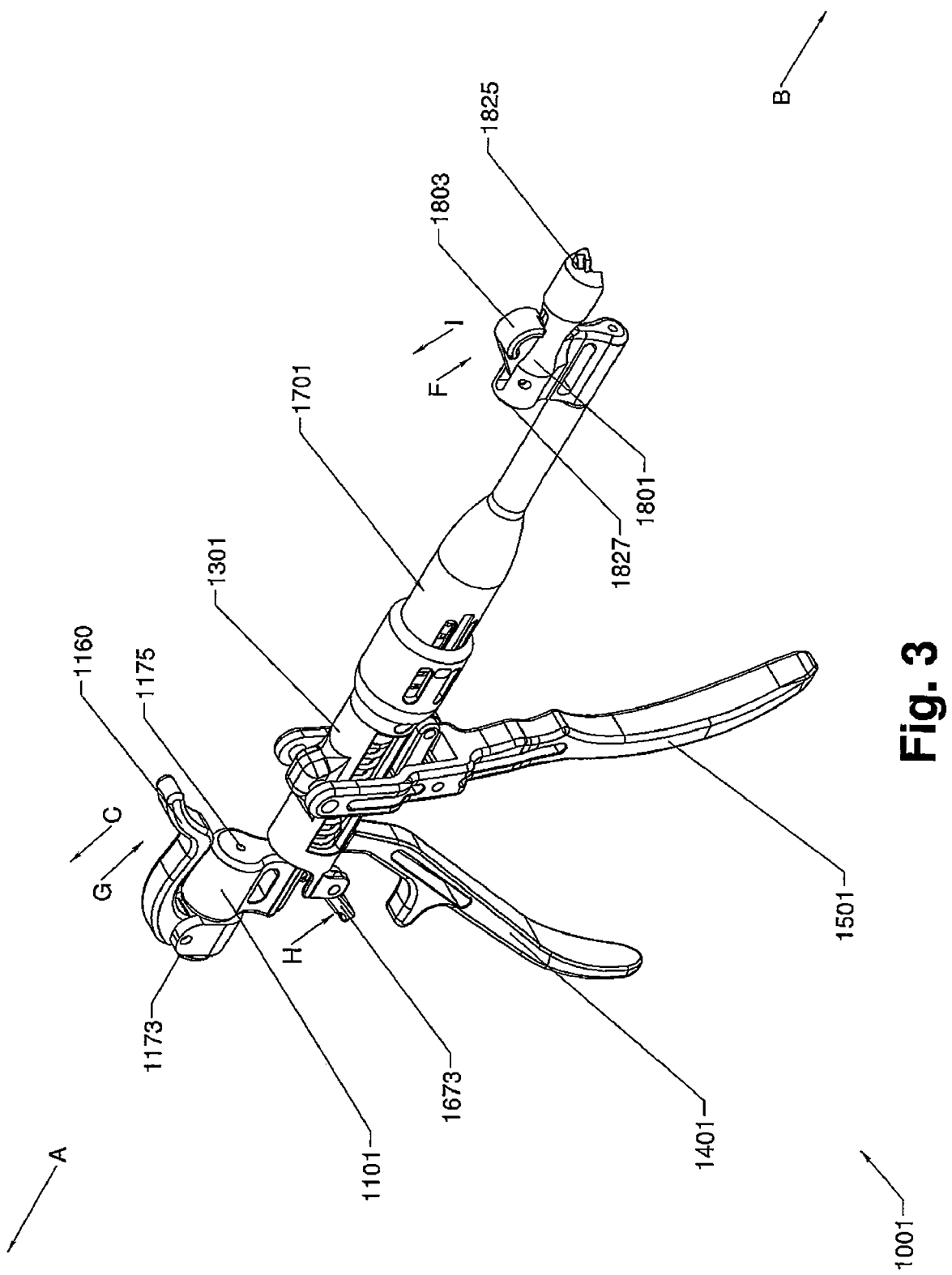
FIG. 3 is an isometric view of the first embodiment of the pistol grip tensioning apparatus in the secured or locked configuration.

The pistol grip tensioning apparatus 1001, 2001, 3001 and 4001 also has ergonomic operation as well. The operation for the first embodiment of the cable tensioning apparatus 1001 is shown in FIGS. 1 through 3. As shown in FIG. 1 for the first cable tensioning apparatus 1001 embodiment, the cable tensioning apparatus 1001 operates by inserting a surgical cable 12 into the cable entrance 1825 of the distal cable clamp assembly 1801 and passing the cable 12 through to the proximal cable clamp assembly 1101 and out the cable exit 1173 with the clamp assemblies 1801 and 1101 in the unsecured or unlocked configuration in the initial condition as shown.

Only the portions of the cable 12 within the passages of the distal and proximal cable clamp assemblies 1801 and 1101 are hidden from view when offset cable clamp assemblies are used. The cable 12 is visible from the distal clamp cable exit 1827 to the proximal clamp cable entrance 1175. The housing member 1301, containing the drive rod 1201 located within, hides the view of the rod 1201.

As shown in FIG. 2, the proximal cable clamp assembly 1101 is then locked and the lever 1501 is repeatedly depressed in direction E by the operator to tension the cable 12. The operator depresses the lever 1501 until the tension indicator 1701 indicates the desired tension has been reached or until the drive rod 1201 is fully rearwardly extended whereby the tensioning process is repeated. The fully extended condition is shown in FIG. 2 whereby the drive rod 1201 has reached its maximum rearwardly extended distance and has become partially visible.

As shown in FIG. 3, the process is repeated first by resetting the drive rod 1201 by depressing the distal clamp lever 1803 of the distal cable clamp assembly 1801 in direction F to lock the cable 12, unlocking the proximal clamp assembly 1101 by depressing the lever 1160 in direction G, and depressing the release lever 1673 in direction H to activate the release mechanism 1671 to reset the drive rod 1201. The pistol grip tensioning apparatus 1001 is finally reset to draw more cable 12 by locking the proximal clamp assembly 1101 by moving the lever 1160 in direction C, and then moving the distal clamp lever 1803 in direction I as shown again in FIG. 3. The process of tensioning then can be repeated as shown in FIG. 1 through 2 to draw another length of cable 12.

Figure 24:
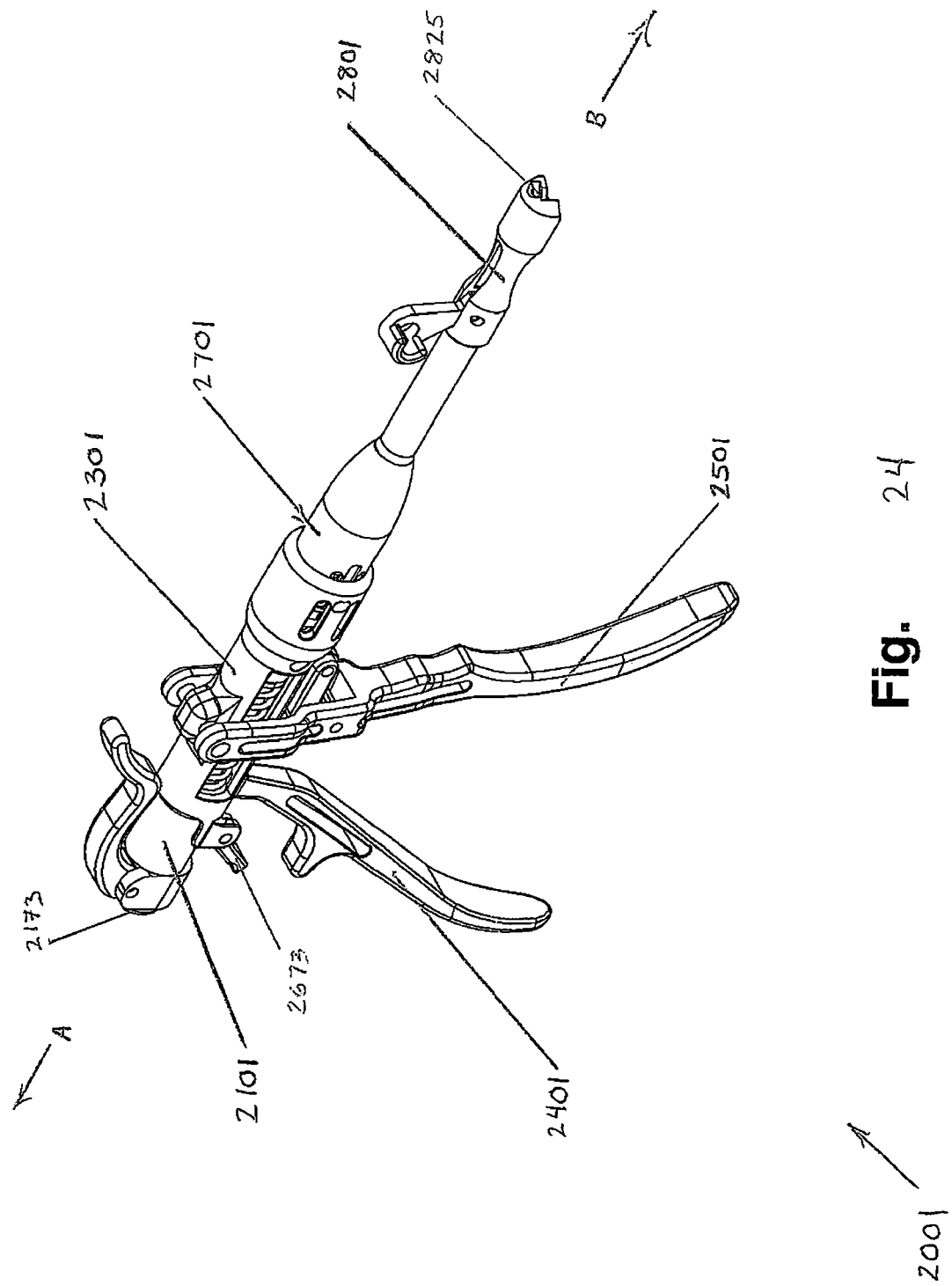
FIG. 24 is an isometric view of the second embodiment of the pistol grip tensioning apparatus in the initial condition.
Figure 25:
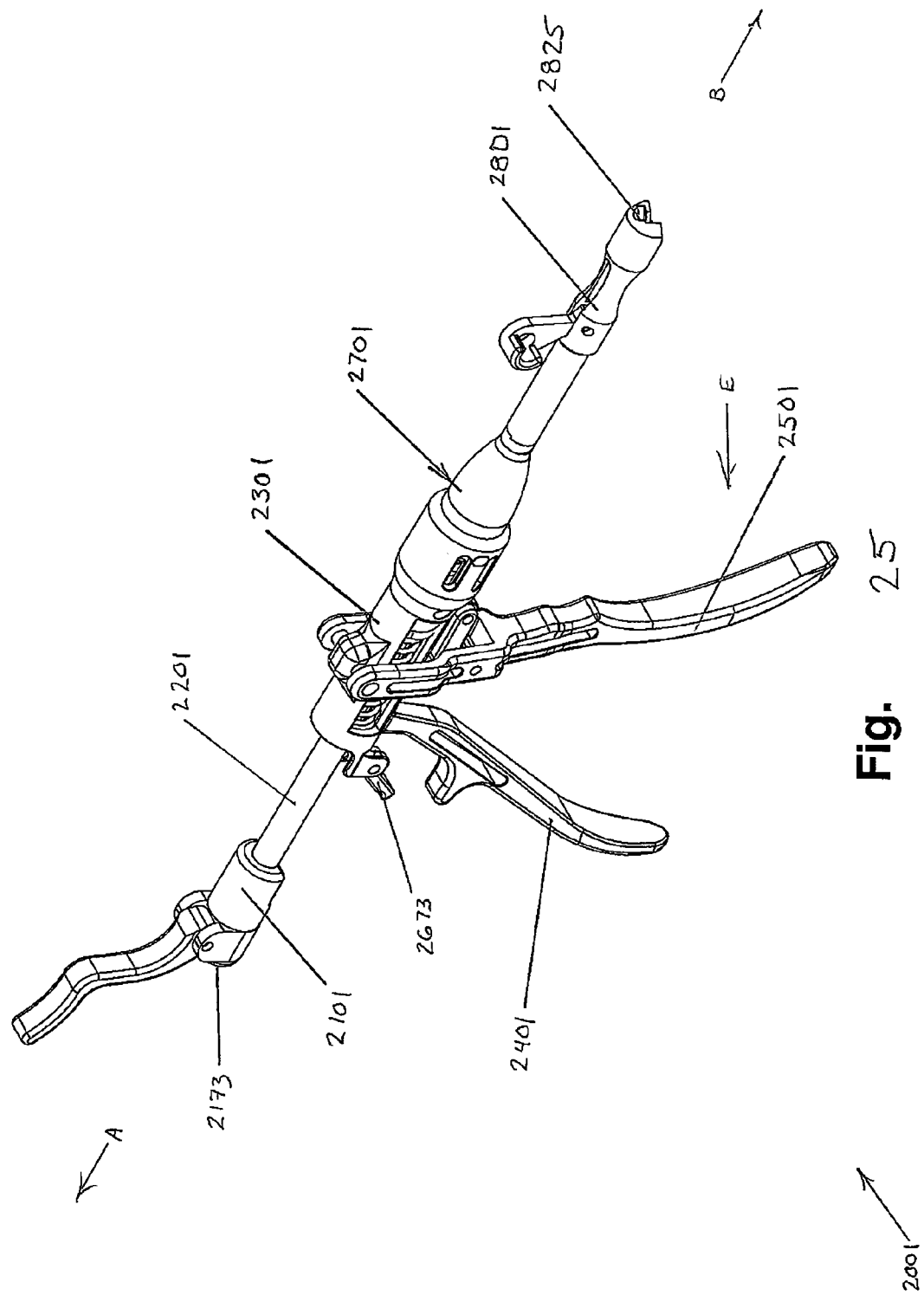
FIG. 25 is an isometric view of the second embodiment of the pistol grip tensioning apparatus in the fully extended condition.
Figure 26:
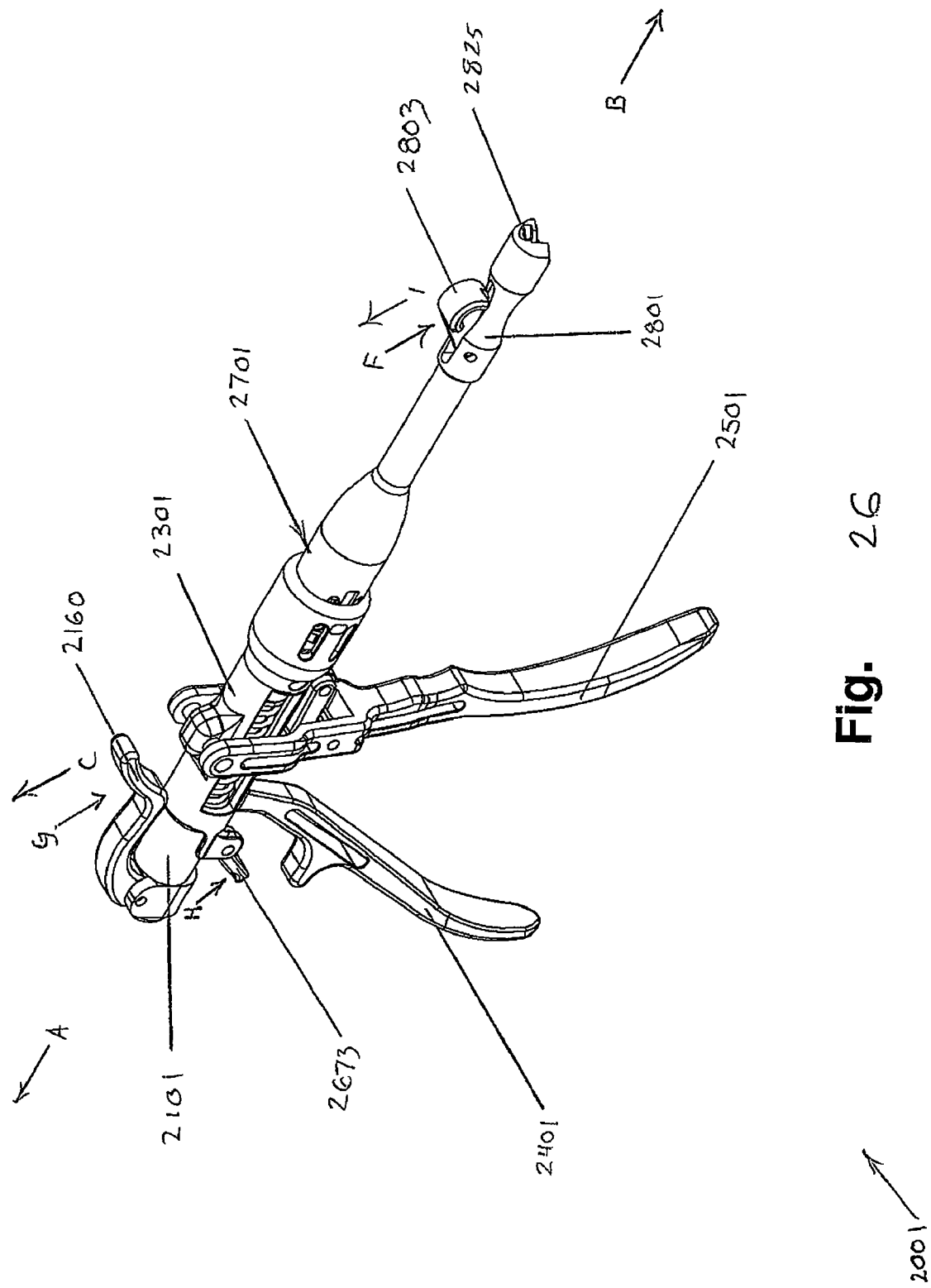
FIG. 26 is an isometric view of the second embodiment of the pistol grip tensioning apparatus in the secured or locked configuration.

The operation of the second embodiment of the pistol grip tensioning apparatus 2001 is nearly identical to the operation of the first embodiment 1001 and is shown in FIGS. 24 through 26. As shown in FIG. 24 for the second cable tensioning apparatus 2001 embodiment, the pistol grip tensioning apparatus 2001 operates by inserting a surgical cable 12 into the cable entrance 2825 of the distal cable clamp assembly 2801 and passing the cable through to the proximal cable clamp assembly 2101 and rearwardly out of the cable exit 2173 with the clamp assemblies 2101 and 2801 in the unsecured or unlocked configuration as shown.

Most of the cable 12 is within the pistol grip tensioning apparatus 2001 and hidden from view. The cable 12 is only visible from the distal clamp assembly 2801 cable entrance 2825 to the incision and any excess cable 12 exiting the proximal clamp cable exit 2173. As shown in FIG. 25, the proximal cable clamp assembly 2101 is then locked and the lever 2501 is repeatedly depressed in direction E by the operator to tension the cable 12. The operator depresses the lever 2501 until the tension indicator 2701 indicates the desired tension has been reached or until the drive rod 2201 is fully rearwardly extended whereby the tensioning process is repeated.

As shown in FIG. 26, the process is repeated first by resetting the drive rod 2201 by depressing the distal clamp lever 2803 of the distal cable clamp assembly 2801 in direction F to lock the cable 12, unlocking the proximal clamp assembly 2101 by depressing the cam lever 2160 in direction G, and depressing the release lever 2673 in direction H to reset the drive rod 2201. The entire pistol grip tensioning apparatus 2001 is finally reset to draw more cable 12 by locking the proximal clamp assembly 2101 by moving the cam lever 2160 in direction C, and then moving the distal clamp lever 2803 in direction I as shown in FIG. 26. The process of tensioning then can be repeated as shown in FIG. 24 through 25 to draw another length of cable 12.

Figure 52:
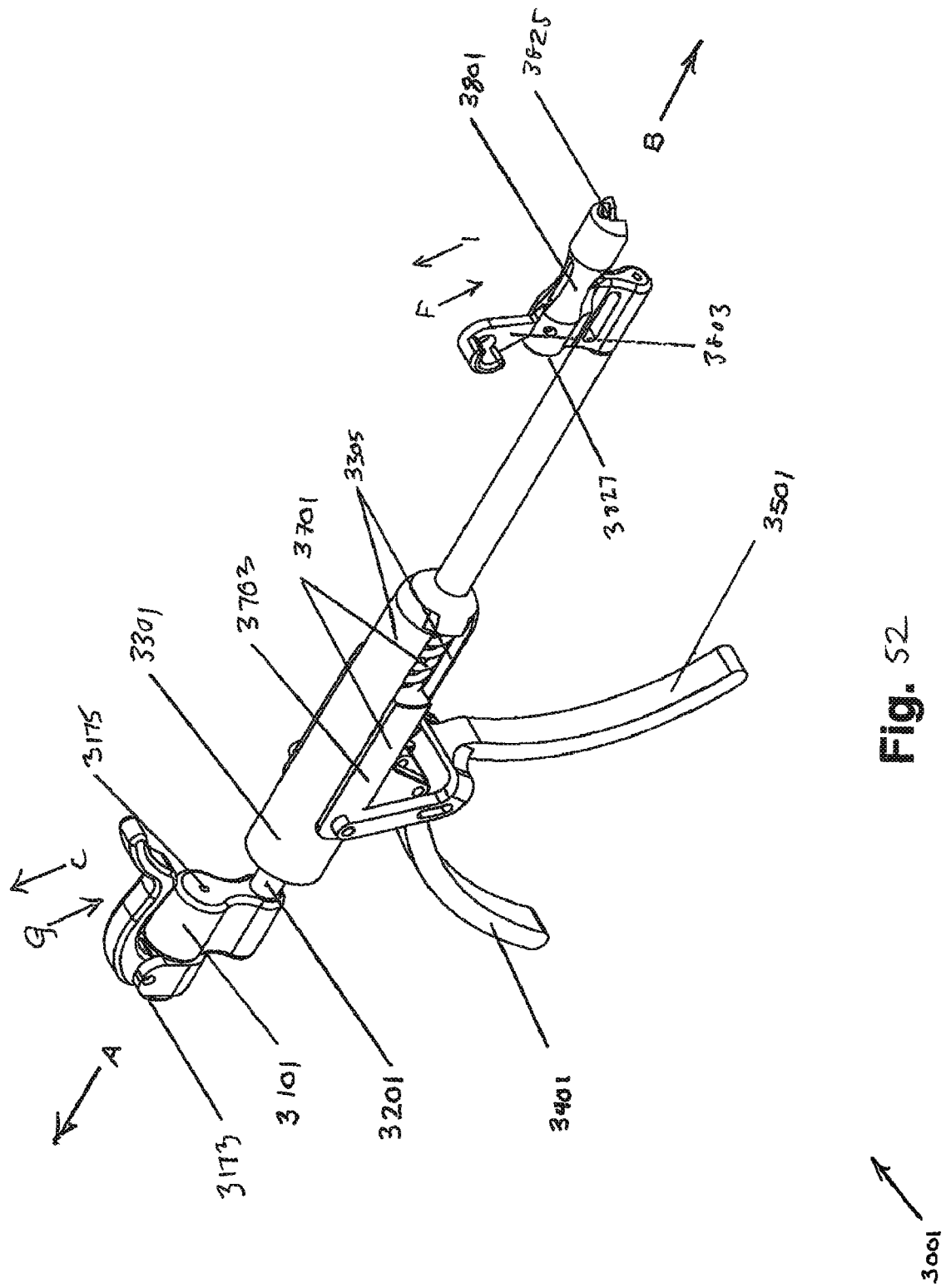
FIG. 52 is an isometric view of the third embodiment of the pistol grip tensioning apparatus in the initial condition.
Figure 53:
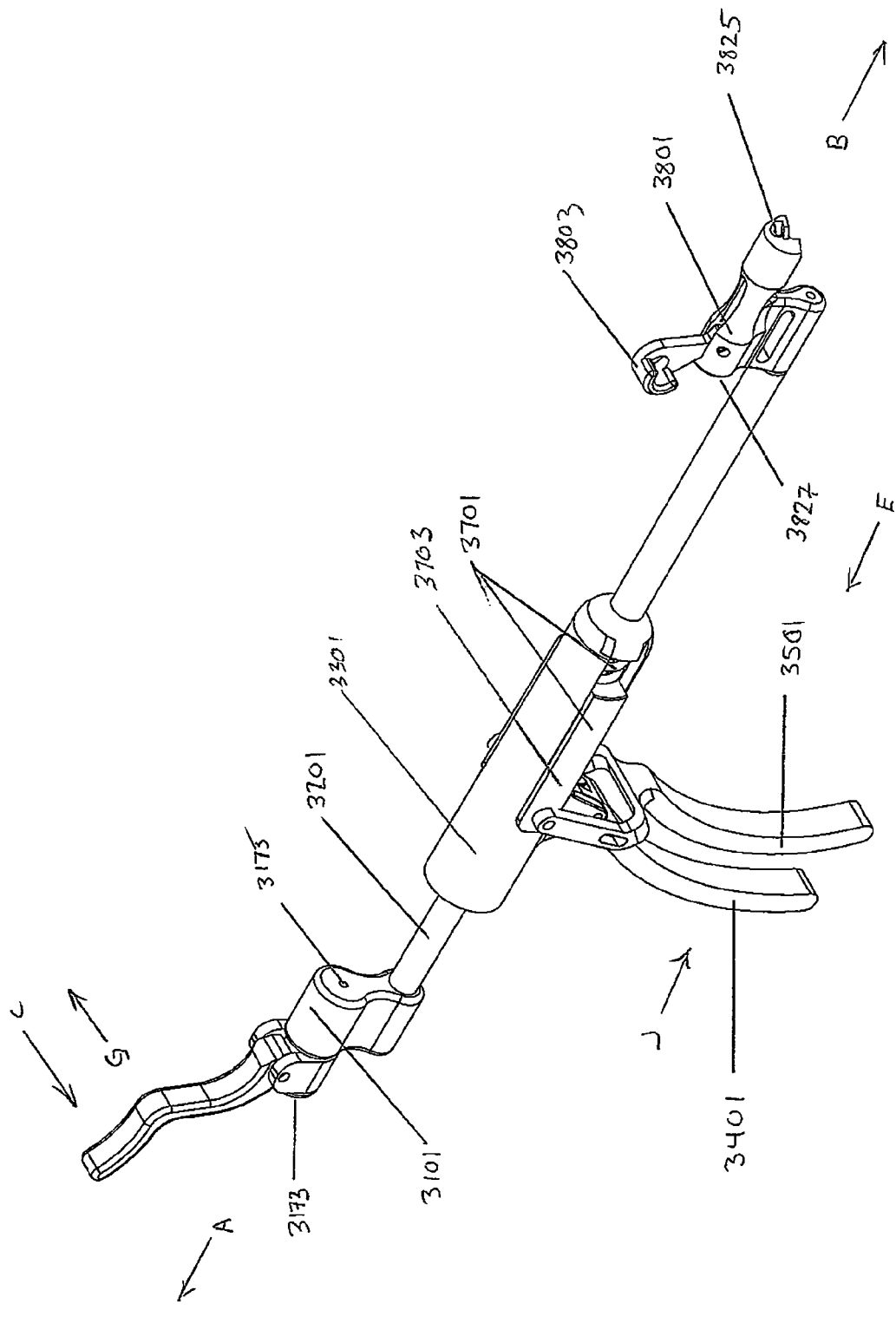
FIG. 53 is an isometric view of the third embodiment of the pistol grip tensioning apparatus in the fully extended condition.

The operation of the third embodiment of the pistol grip tensioning apparatus 3001 is nearly identical to the operation of the first embodiment 1001 with two exceptions and is shown in FIG. 52 and FIG. 53. However, the third embodiment of the pistol grip tensioning apparatus 3001 requires the additional step of depressing both the handle 3401 and lever 3501 simultaneously. The third embodiment of the pistol grip tensioning apparatus 3001 also requires reading the tension indication mechanism 3701 from the sides of the device or apparatus rather than from the top as in the first embodiment.

Figure 68:
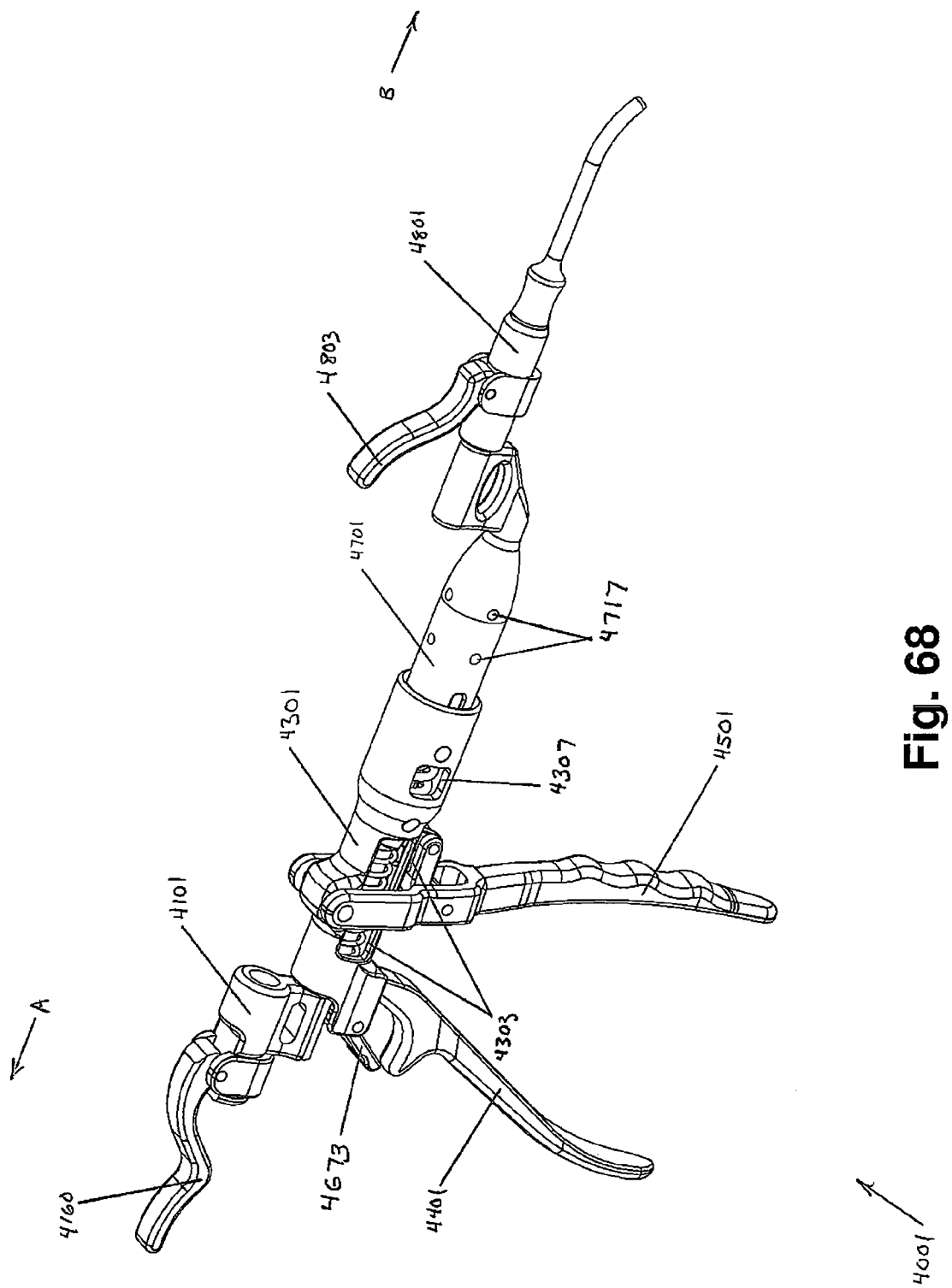
FIG. 68 is an isometric view of the fourth embodiment of the pistol grip tensioning apparatus in the initial condition.
Figure 69:
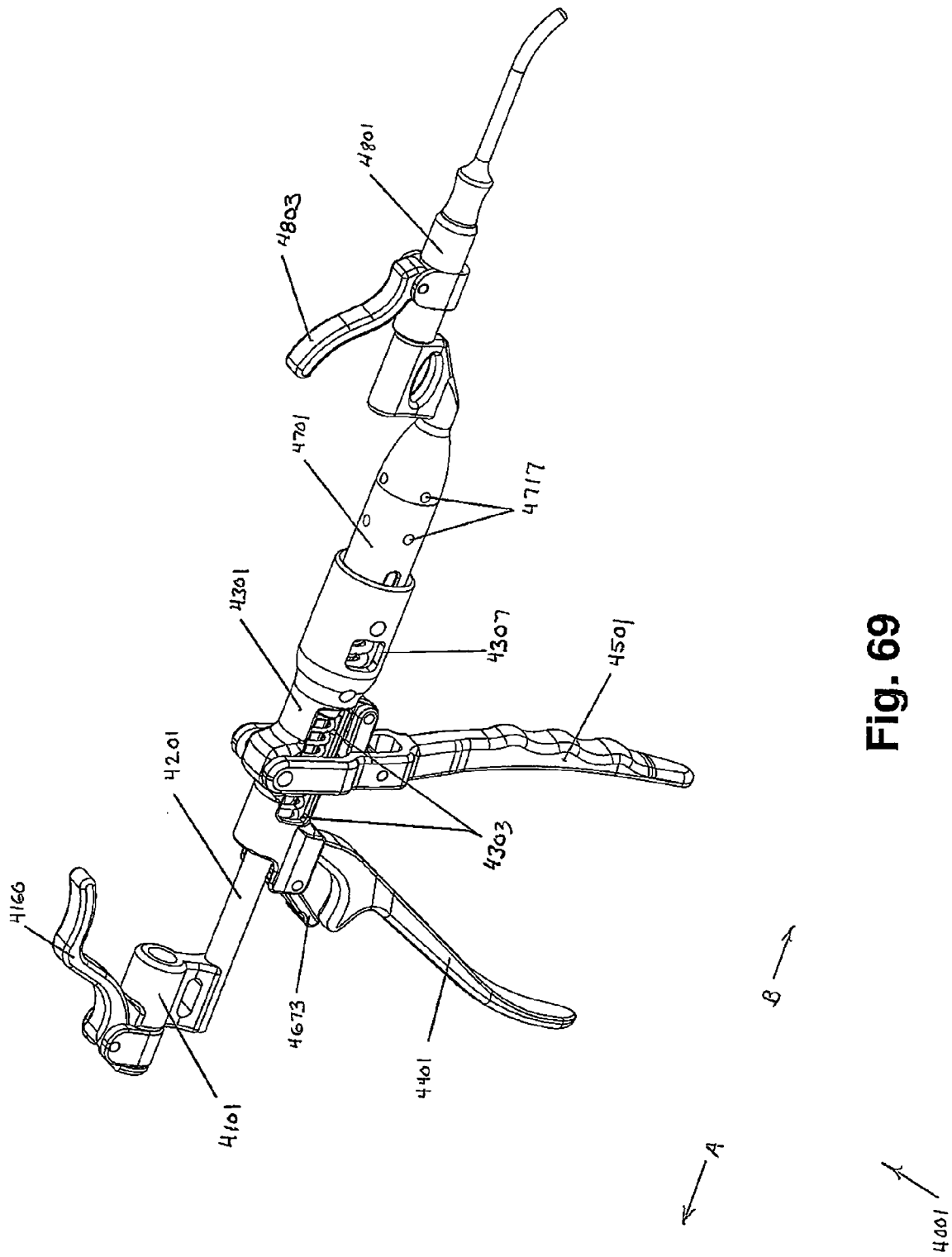
FIG. 69 is an isometric view of the fourth embodiment of the pistol grip tensioning apparatus in the fully extended condition.
Figure 70:
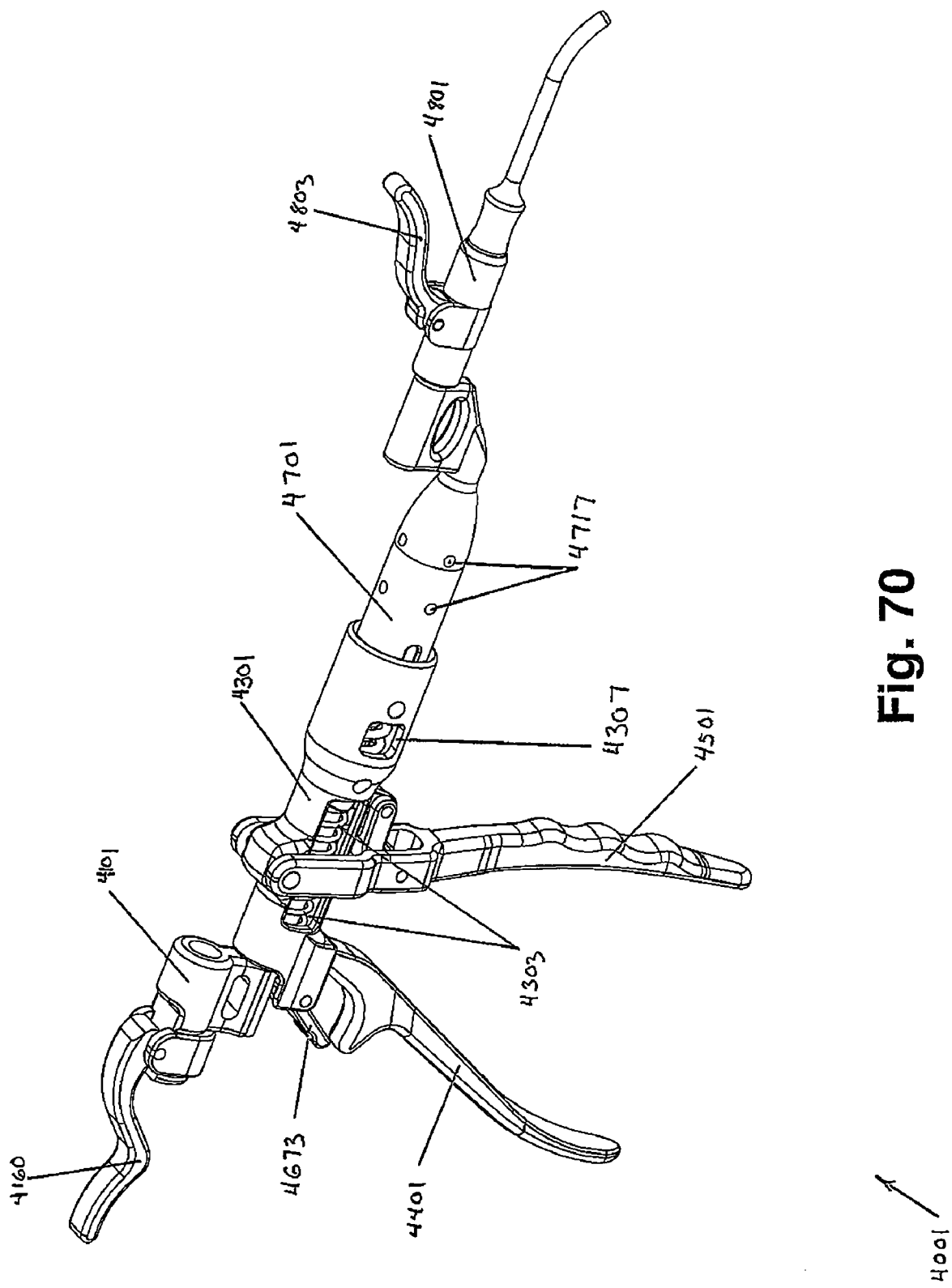
FIG. 70 is an isometric view of the fourth embodiment of the pistol grip tensioning apparatus in the secured or locked configuration.

The operation of the fourth embodiment of the pistol grip tensioning apparatus 4001 is nearly identical to the operation of the first embodiment 1001 with two relevant exceptions as shown in FIG. 68 through FIG. 70. In the fourth pistol grip tensioning apparatus 4001, the surgical connector or crimp 10 does not seat or mechanically interlock with the cable entrance 4825. The operation of the distal and proximal clamp assemblies 4101, 4801 is simplified because rotation of the lever 4803 and 4160 in the distal direction B locks the surgical cable 12 and rotation in the proximal direction A unlocks the cable 12. All of the various embodiments of the pistol grip tensioning apparatus 1001, 2001, 3001 and 4001 can be operated without a surgical connector 10 or crimp depending on surgeon's preference.

The cable tensioning apparatus 1001, 2001, 3001 and 4001 can also have a variety distal cable clamp assemblies 1801, 2801, 3801, and 4801 which correspond to various styles or types of surgical connectors 10 or crimps. The various distal cable clamp assemblies 1801, 2801, 3801, and 4801 have a modular configuration tube so that they can connect and disconnect from the cable tensioning apparatus 1001, 2001, 3001 and 4001 to allow a variety of distal cable clamp assemblies 1801, 2801, 3801, and 4801 to be used.

Typically in most surgeries, the cable 12 is passed around the bone to be cerclaged, i.e. the patient's bone is wrapped with supporting cable. The cable tensioning apparatus 1001, 2001, 3001 and 4001 will be provided to the surgeon and the unattached end of the surgical cable will be passed through the clamp assemblies as previously described. Typically, the surgical connector 10 is pulled or positioned on the distal cable clamp assemblies 1801, 2801, 3801, and 4801 which is in turn in contact with an implant or the patient's bone. However, the distal cable clamp assembly 1801, 2801, 3801, and 4801 can be used with or without a surgical connector 10 to bring the clamp assembly 1801, 2801, 3801, and 4801 directly in contact with the bone.

In most surgeries, a single cycle of the drive rod 1201, 2201, 3201, and 4201 displacement to the fully rearwardly extended will provide enough travel or displacement to fully draw the cable 12 to the desired tension. Once the cable 12 is positioned, then the cable 12 will be locked in place by turning a set screw, a cam lock, or crimped on either the surgical connector 10 or on the implant itself. The release lever 1673, 2673, 3673, and 4673 will then be depressed to reduce tension on the cable 12 to allow the cable tensioning apparatus 1001, 2001, 3001 and 4001 to be removed. The cable 12 will be trimmed or cut in place and the patient will be closed.

However, multiple surgical cables can be tightened with even a single cable tensioning apparatus 1001, 2001, 3001 and 4001 in an iterative fashion because often when the first cable is tightened another adjacent cable will then loosen as the tensile load is taken up by the adjacent cable. The pistol grip tensioning apparatus 1001, 2001, 3001 and 4001 can work iteratively by securing or locking a distal cable clamp assembly 1801, 2801, 3801, and 4801 by rotating the clamp lever (1803, 2803, 3803, 4803) and then disconnecting to the tensioning apparatus 1001, 2001, 3001 and 4001 from the distal cable clamp assembly 1801, 2801, 3801, and 4801. Typically, the release lever 1673, 2673, 3673, and 4673 must be first depressed as well as the proximal cable clamp assemblies' levers 1160, 2160, 3160 and 4160.

Another distal cable clamp assembly 1801, 2801, 3801, and 4801 will then be attached or connected to the tensioning apparatus 1001, 2001, 3001 and 4001 with another cable 12 to be tensioned as previously described. If a cable 12 and distal cable clamp assembly 1801, 2801, 3801, and 4801 needs to be retightened then the tensioning apparatus 1001, 2001, 3001 and 4001 is reattached and more tension is applied as previously described. Each individual cable 12 is then secured with a set screw, cam or crimp and trimmed as previously described.

The operation of the cable tensioning embodiments are surprisingly intuitive because the operator can see and feel how the device is operating since the surgeon can see or feel where the cable 12 is located during the cable tensioning process. For example, in apparatus 1001, housing ducts 1303, shown in FIG. 4, allow for visual inspection of the drive mechanism 1601 for mechanical error detection and correction of the friction drive mechanism 1601. The state of the proximal and distal clamp assemblies 1101 and 1801 in the locked or unlocked configuration, the degree of extension of the drive rod 1201, and even the amount of tension on the cable 12 can be ascertained by touch alone when the vision of the surgeon is obscured by blood or tissue of the patient. The ability to see or feel the components and process of tensioning creates tactile and visual feedback that makes the use of the apparatus 1001 easy and intuitive. Almost no training is required by medical personnel unlike complex cable tensioning systems which are difficult to use due to the hidden operation of key components.

The intuitive nature of the operation of the fourth cable tensioning apparatus 4001 is further improved by the particular design configuration and arrangement of the cable clamp assemblies 4101, 4801. As shown in FIG. 68, the proximal and distal cable clamp assemblies 4101, 4801 are arranged to unlock by moving the levers 4160, 4803 in the proximal direction A to allow surgical cable 12 to be fed in the rearward or proximal direction A. This way the levers 4160, 4803 only need to rotate in one direction to unsecure the surgical cable 12 to allow ease of use and aid in understanding operation for the operator. Conversely, the proximal and distal cable clamp assemblies 4101, 4801 are locked by moving the levers in the distal direction B to secure or lock the clamp assemblies 4101, 4801. In addition, all of the levers 1160, 1803, 2160, 2803, 3160, 3803, 4160, 4803 for the embodiments 1001, 2001, 3001, 4001 have directions of use of the levers laser etched on to the housing (not shown) of the distal and proximal cable clamp assemblies to indicate which direction to lock and unlock the clamp assemblies.

The cable tensioning apparatus 1001, 2001, 3001 and 4001 uses a pistol grip type interface by the user of the apparatus. The depression of the large pistol grip type lever/handle combination allows a large amount of cable 12 to be drawn through the apparatus and still provide sufficient tensile force. The cable tensioning process can easily be repeated through simple operation of the distal and proximal cable clamp assemblies. Other devices do not use a pistol style grip mechanism to tension cable, but rather use pistol grips to crimp sleeves onto cables or wires on cables.

Cleanability

The cleanability of the cable tensioning apparatus 1001, 2001, 3001 or 4001 reduces the risk of infection to patients due to cross contamination of biologic materials from patient to patient after repeated uses of the cable tensioning apparatus 1001, 2001, 3001, and 4001. The risk of infection is minimized because of the ease of partial disassembly or ease of access of internal components, for example through ducts 1303 and 1307 or flow ports throughout the device to allow high pressure flushing of the cable tensioning apparatus. The cleanability was unpredicted in the design of the cable tensioning apparatus 1001, 2001, and 3001 because the combination of ducts 1303 and 1307, the simple construction, and ease of disassembly provided unexpected hygienic results. The pistol grip tensioning apparatus 1001, and 2001 are unique because the apparatus 1001, and 2001 allows partial disassembly for cleaning. Note that most medical instruments are designed not to be disassembled because untrained medical personnel, i.e. OR techs, are not able to effectively reassemble complex medical instruments. The ability to partially disassemble the apparatus 1001 and 2001 provides the optimum balance of the need for hygiene against the need to simplify sterilization procedures for untrained medical personnel.

Figure 4:
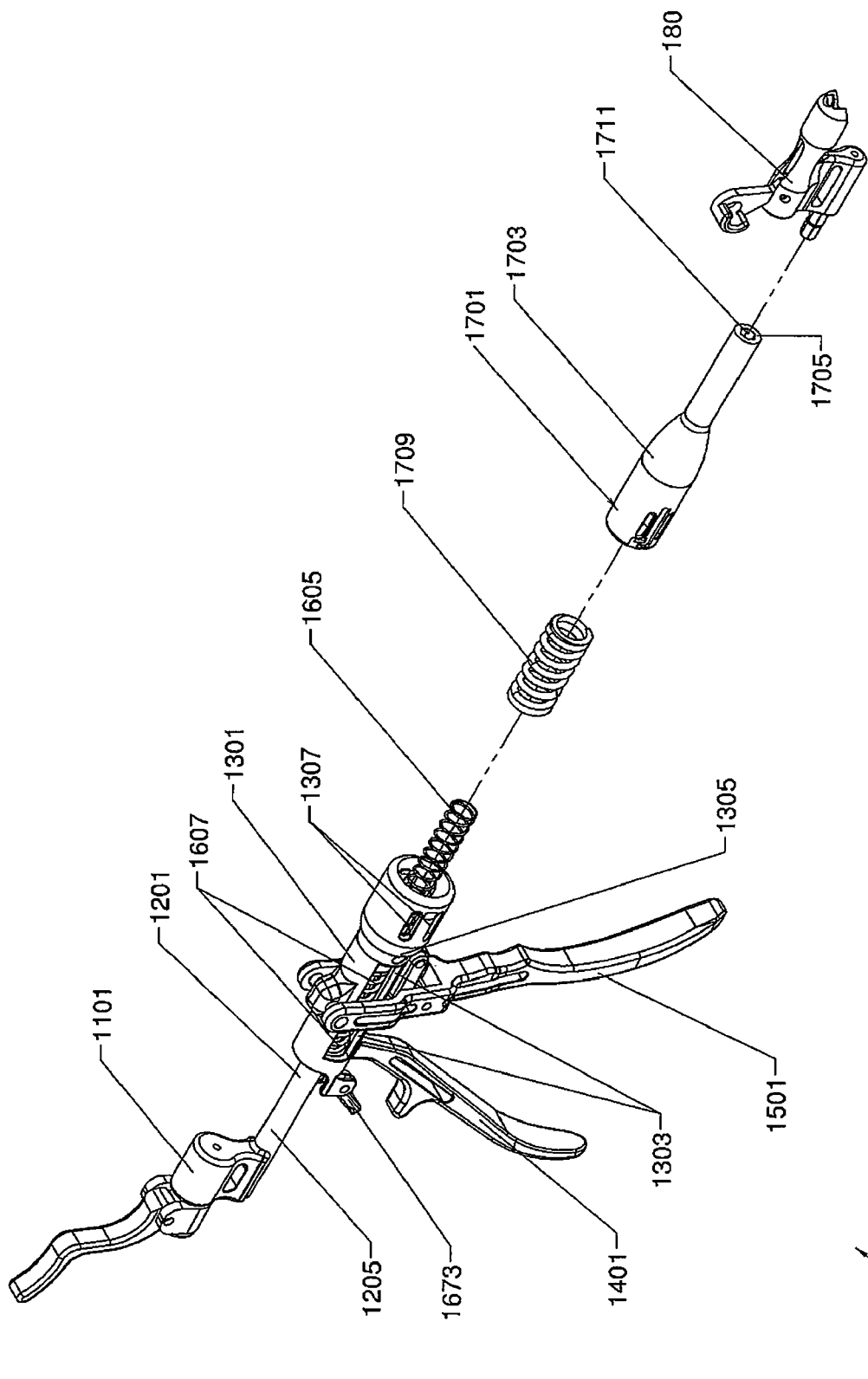
FIG. 4 is an exploded view of the first embodiment of the pistol grip tensioning apparatus.
Figure 5:
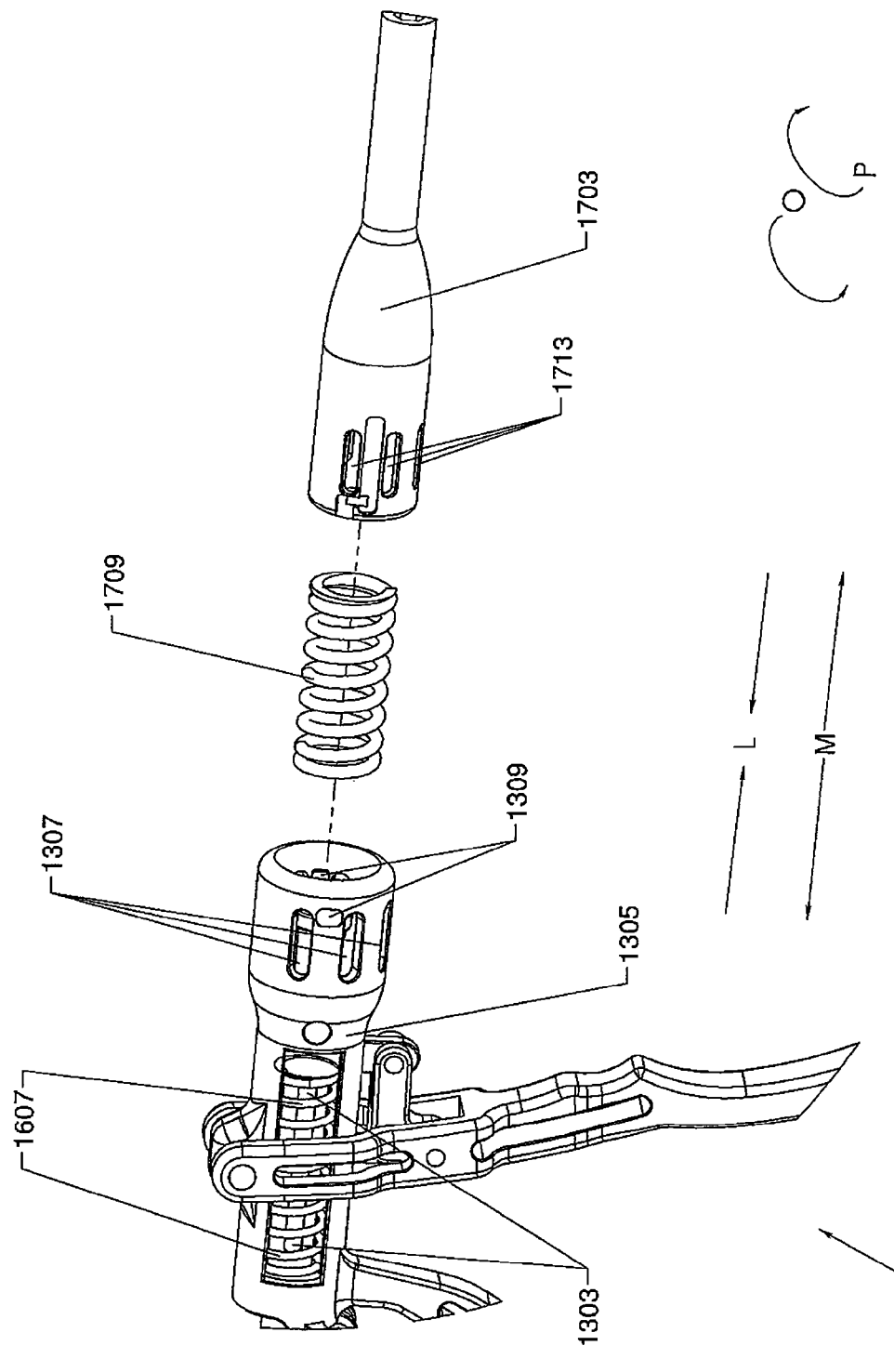
FIG. 5 is a detailed exploded view of the first embodiment of the pistol grip tensioning apparatus.
Figure 27:
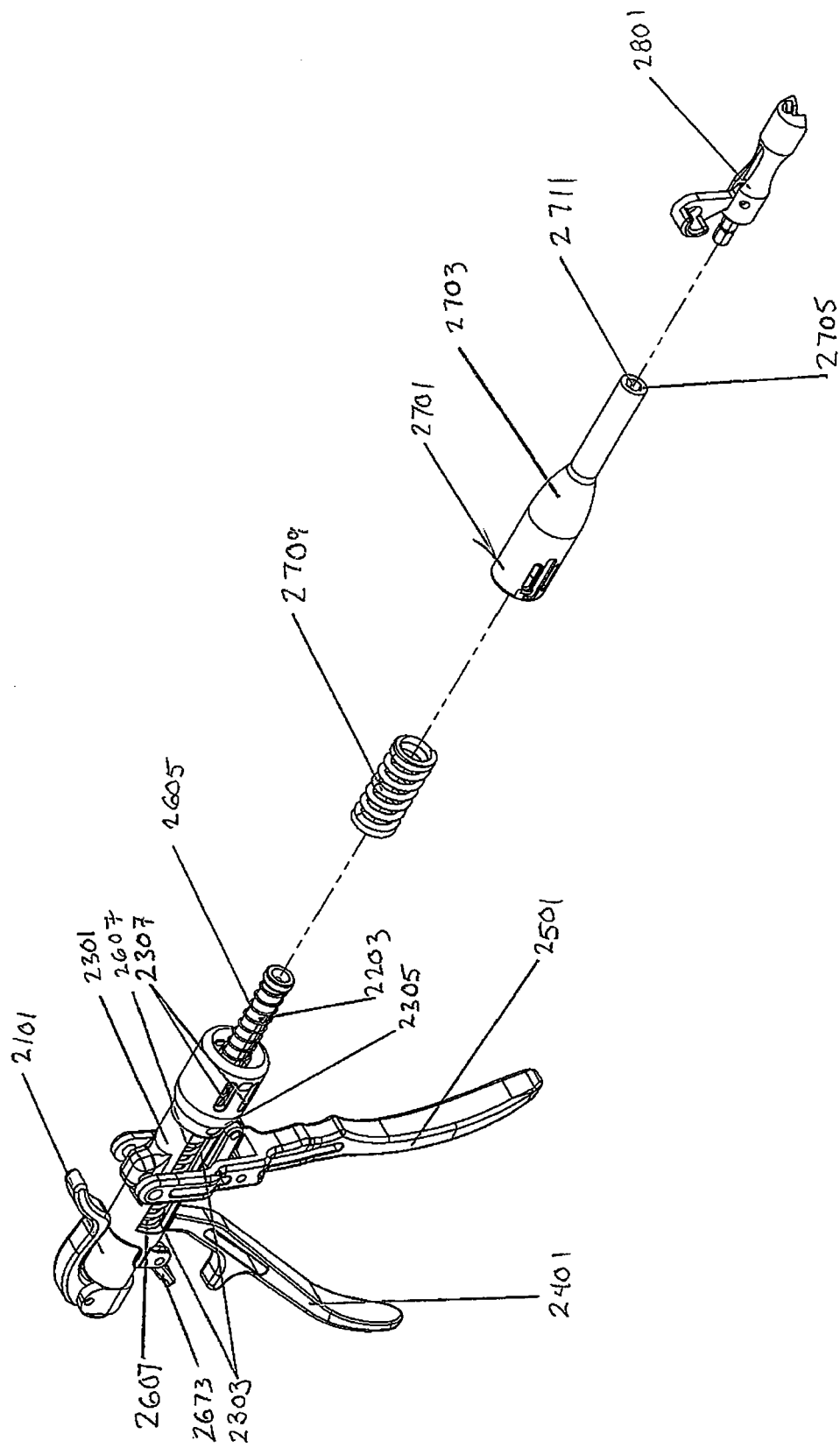
FIG. 27 is an exploded view of the second embodiment of the pistol grip tensioning apparatus.

Ease of disassembly can be best seen in FIG. 4 and FIG. 27 which show how a majority of interior components can be directly accessed upon disassembly. As shown in FIGS. 4, 5, 27 and 28, a bayonet connection allows for the disassembly and reassembly of the cable tensioning apparatus 1001 and 2001 for the first and second embodiments only. (Please note that the second embodiment components are hereinafter distinguished from the first embodiment by the text within the parenthesis.) The bayonet connection and components for the first embodiment of the cable tensioning apparatus 1001 shown in FIGS. 4 and 5 are identical for the second embodiment of the apparatus 2001 shown in FIGS. 27 and 28.

The cable tensioning apparatus 1001 (or 2001) is disassembled as shown in FIG. 4 (or 27) for cleaning and sterilization of the apparatus prior to surgery. To disassemble the core components, the housing structure 1305 (or 2305) is rotated relative to the indicator structure 1703 (or 2703) to disengage the bayonet connection (described in detail subsequently) and disconnect the housing 1301 (or 2301) from the indicator 1701 (or 2701). The drive rod reset spring 1605 (or 2605), the calibrated compression spring 1709 (or 2709), and the interior of the indicator structure 1703 (or 2703) then becomes accessible for cleaning upon partial disassembly as shown in FIG. 4 (or 27). Similarly, the rack portion 1205 (or 2205) of the drive rod 1201 (or 2201) can be exposed for cleaning upon disassembly. The cylindrical portion 1203 (or 2203) of the drive rod 1201 (or 2201) is also accessible upon depression of the release lever 1673 (or 2673).

Figure 28:
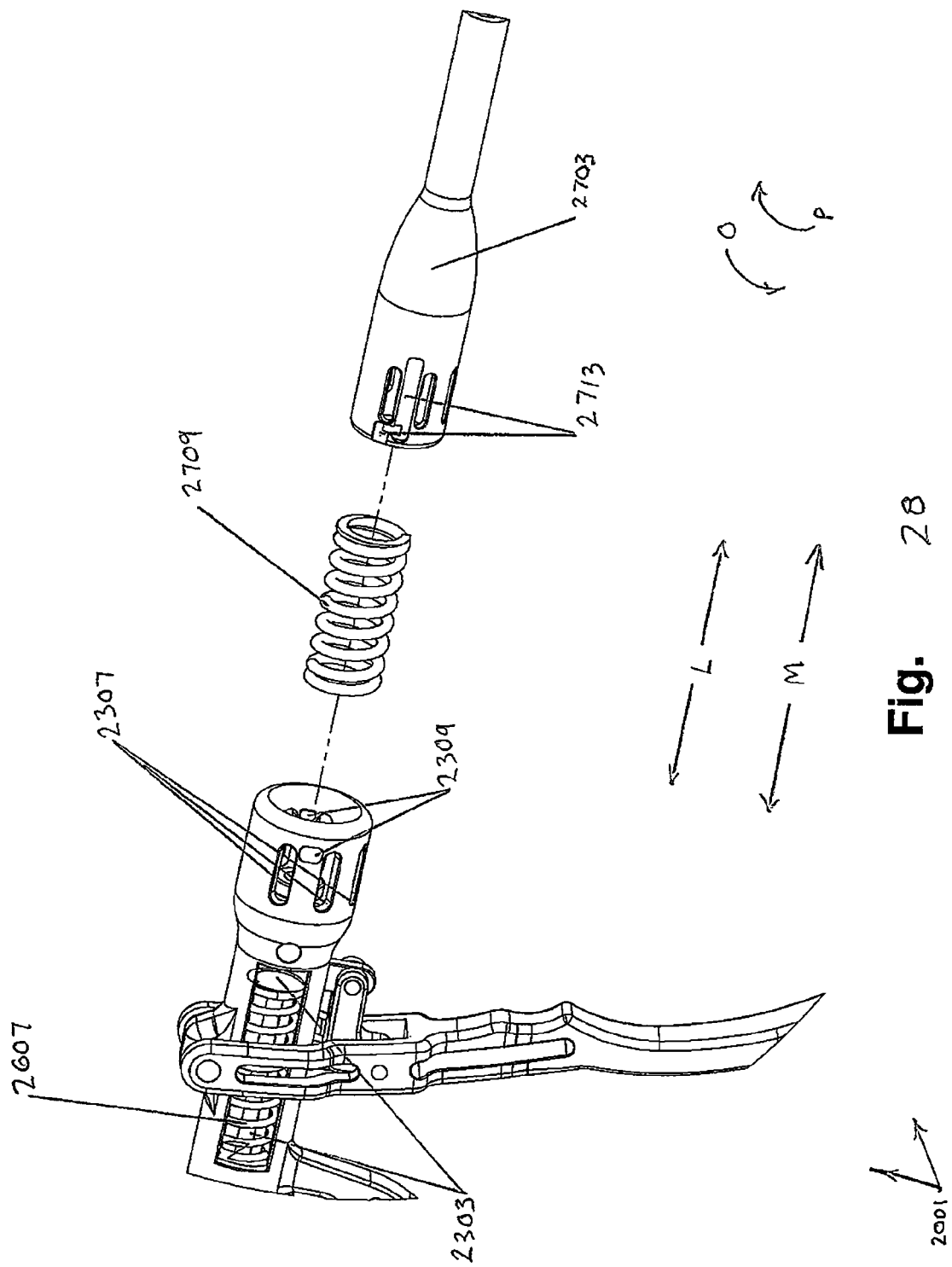
FIG. 28 is a detailed exploded view of the second embodiment of the pistol grip tensioning apparatus.

The bayonet connection is formed from the bayonet lugs 1309 (or 2309) on the housing structure 1305 (or 2305) and the bayonet recess on the indicator structure 1703 (or 2703) as shown in FIGS. 5 and 28. The bayonet lugs 1309 (or 2309) are mounted and project from the housing structure 1305 (or 2305) at points 180 degrees apart on the inner walls of the cylindrical housing structure 1305 (or 2305). The bayonet lugs 1309 (or 2309) provide a male mechanical connection to the corresponding bayonet recesses 1713 (or 2713). The L-shaped bayonet recesses between cleaning ports 1713 (or 2713) are machined from the housing structure 1305 (or 2305) at points 180 degrees apart on the outer walls of the cylindrical indicator structure 1703 (or 2703).

To disassemble the cable tensioning apparatus 1001 (or 2001), the operator compresses the housing structure 1305 (or 2305) against the indicator structure 1703 (or 2703) shown as direction L in FIG. 5 (or FIG. 28). The operator then rotates the indicator structure 1703 (or 2703) in direction O relative to the housing structure 1305 (or 2305), and then extends or separates the housing structure 1305 (or 2305) from the indicator structure 1703 (or 2703) shown as direction M in FIG. 5 (or FIG. 28) to disengage the bayonet connection and disassemble the components.

To assemble or to reassemble the bayonet connection, the operator inserts the indicator structure 1703 (or 2703) into the housing structure 1305 (or 2305) in direction L as shown in FIG. 5 (or FIG. 28) so that the bayonet lugs 1309 (or 2309) mesh with the bayonet recesses 1713 (or 2713). The operator then rotates the indicator structure 1703 (or 2703) in direction P until the indicator structure 1703 (or 2703) and the housing structure 1305 (or 2305) lock together.

The bayonet connection of the cable tensioning apparatus 1001 and 2001 allows access for cleaning which increases the effectiveness of the autoclave sterilization process by preventing insulation to the steam heat. The bayonet connection and ability to partially disassemble the apparatus 1001 (or 2001) also improves hygiene and maintenance of the device.

All of the cables tensioning apparatuses 1001, 2001, 3001, and 4001 have the modular distal cable clamp assemblies

Figure 71:
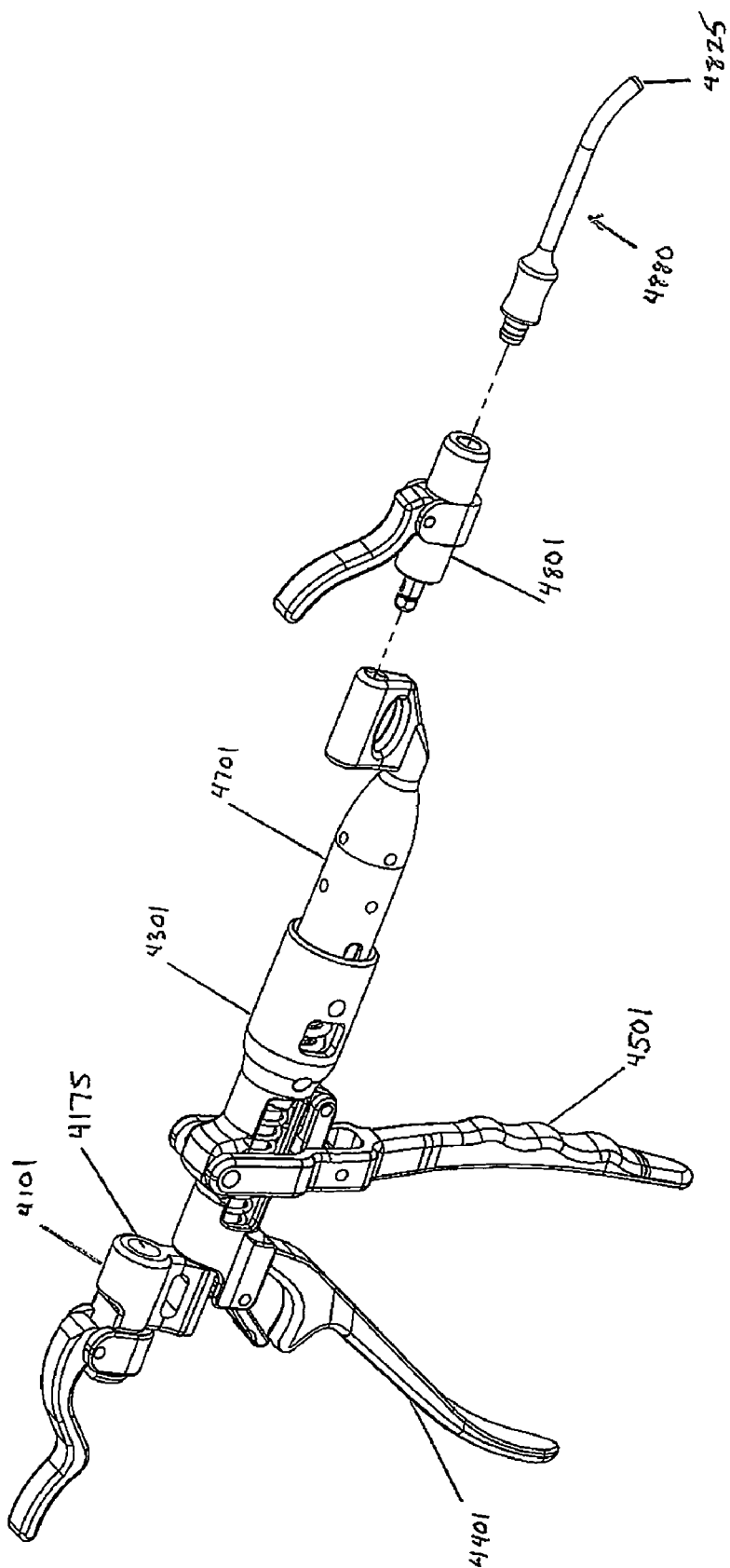
FIG. 71 is an exploded view of the fourth embodiment of the pistol grip tensioning apparatus.

1801, 2801, 3801, and 4801 and that are able to be easily disassembled due to the modular construction shown in FIGS. 4, 27 and 71. The distal cable clamp assembly 1801 (or 2801) can be separated from the indicator structure 1703 (or 2703) to allow cleaning of the tubular extension 1821 (or 2821) surfaces shown in FIGS. 18, 19, 41 and 42. In addition, access is also given to the indicator passage 1711 (or 2711) via the hexagonal socket 1705 (or 2705) for jet washing of the indicator passage 1711 (or 2711) with cleaning solutions as shown in FIGS. 4 and 27. The modular feature of the distal cable clamp assembly 3801 of the third apparatus 3001 of the cable tensioning apparatus 3001 is identical to the first apparatus 1001 and is not repeated for brevity.

The cable tensioning apparatuses 1001, 2001, 3001 and 4001 have ducts 1303, 1307, 2303, 2307, 4303, 4307, 4717 or flow ports so that interior components easily are flushed with cleaning solution to remove tissue or biologic materials best shown in FIGS. 4, and 27. For example, the proximal housing ducts 1303 (or 2303) are provided in the housing member 1301 (or 2301) to allow access to the drive rod reset spring 1605 (or 2605) and other components of the drive mechanism 1601 (or 2601) for jet washing and cleaning. The ducts 1303 (or 2303) are located intermittently throughout the housing member 1301 (or 2301) at strategic points to allow access to internal components at irregular intervals along the apparatus 1001 and yet not interfere with mechanical and structural functions. As shown in FIGS. 4, 5, 27 and 28, the distal housing ducts 1307 (or 2307) provide access to the drive rod reset spring 1605 (or 2605) and to the cylindrical portion 1203 (or 2203) of the drive rod 1201 (or 2201) upon depression of the release lever 1673 (or 2673). The proximal and distal ducts 1303 and 1307 (or 2303 and 2307) again allow for jet washing of the drive mechanism 1601 (or 2601) with cleaning solutions to flush out tissue or biologic materials.

Figure 54:
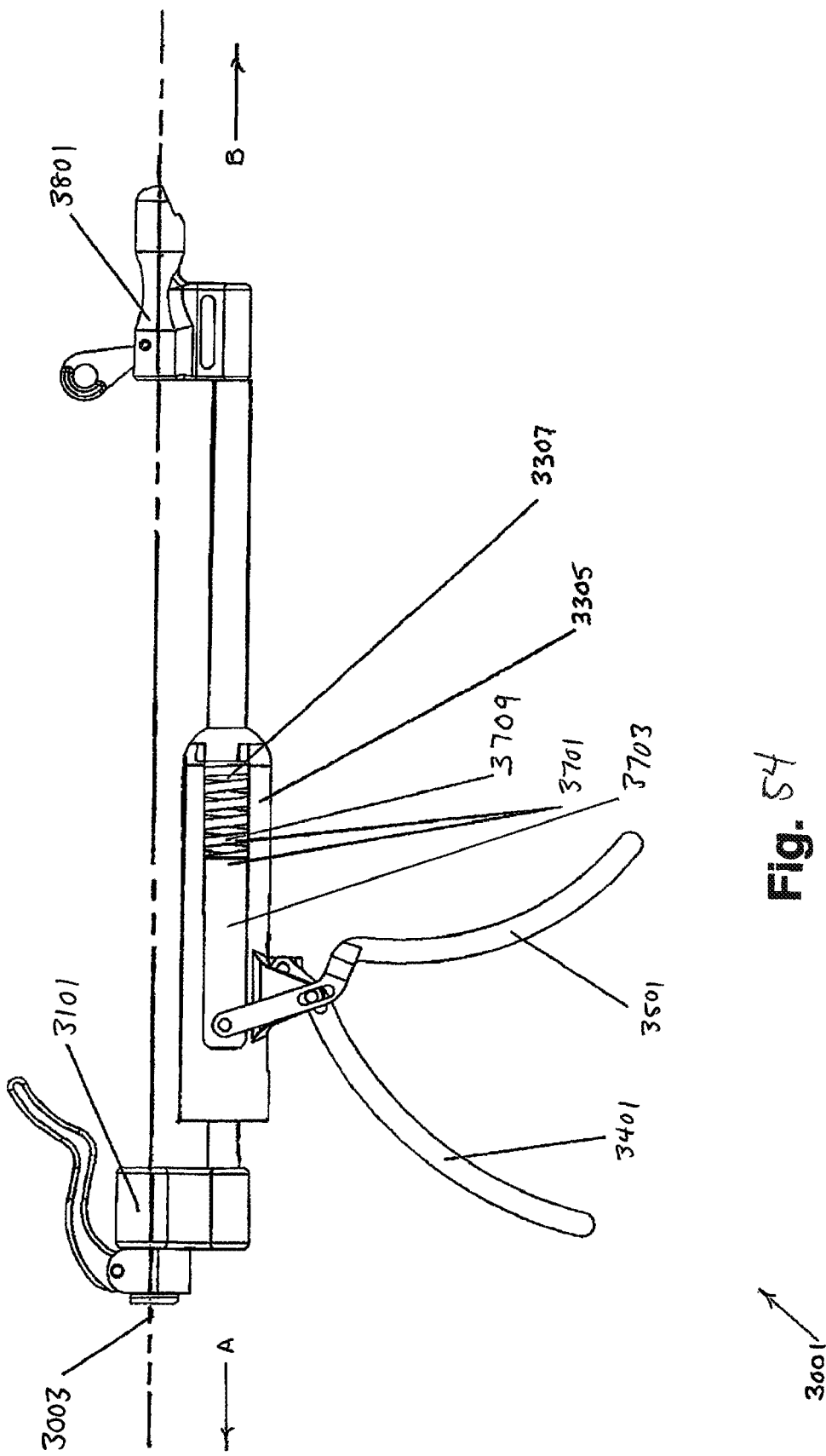
FIG. 54 is a front view of the third embodiment of the pistol grip tensioning apparatus in the initial condition.
Figure 55:
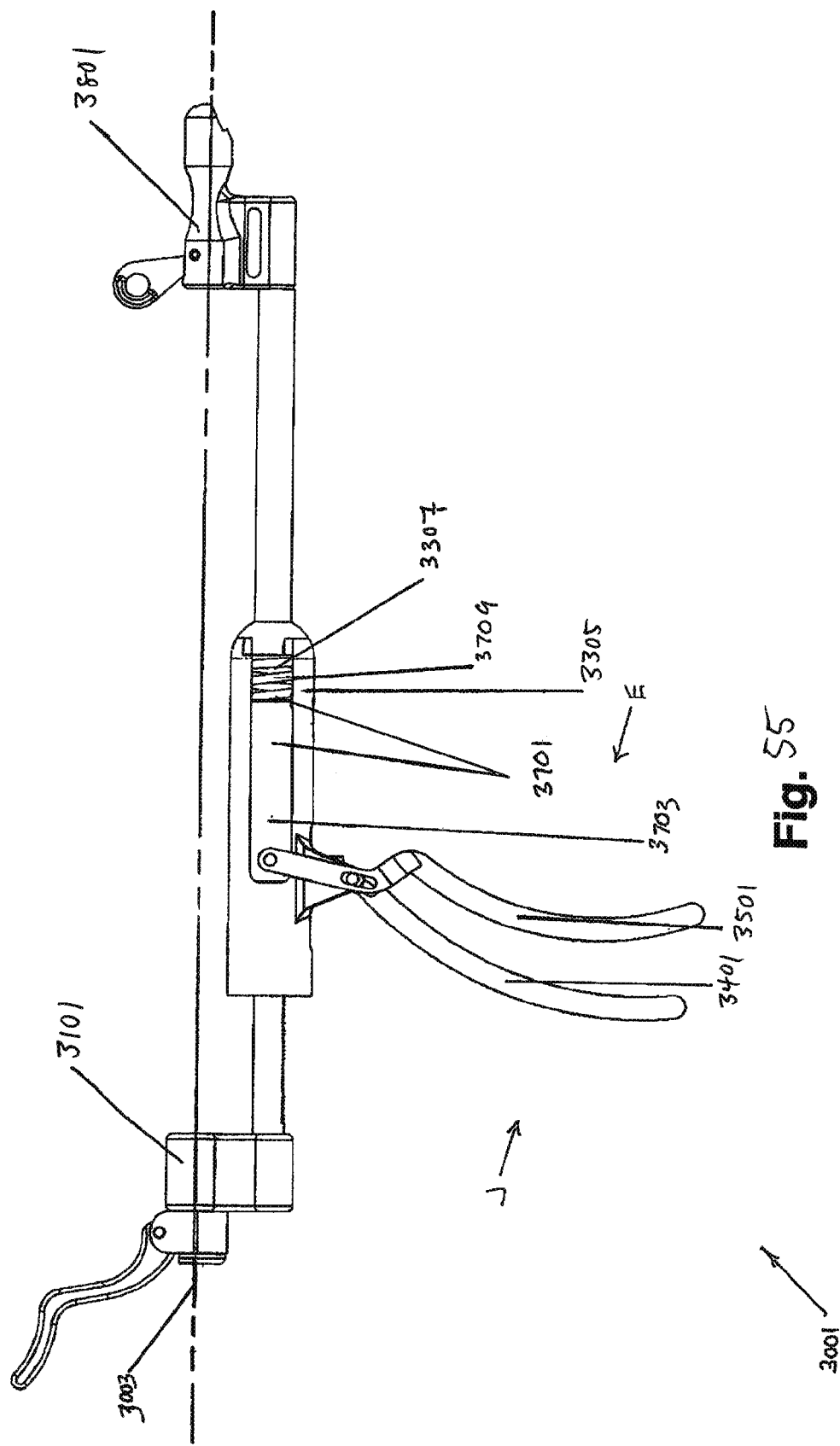
FIG. 55 is a front view of the third embodiment of the pistol grip tensioning apparatus in the fully extended condition.
Figure 62:
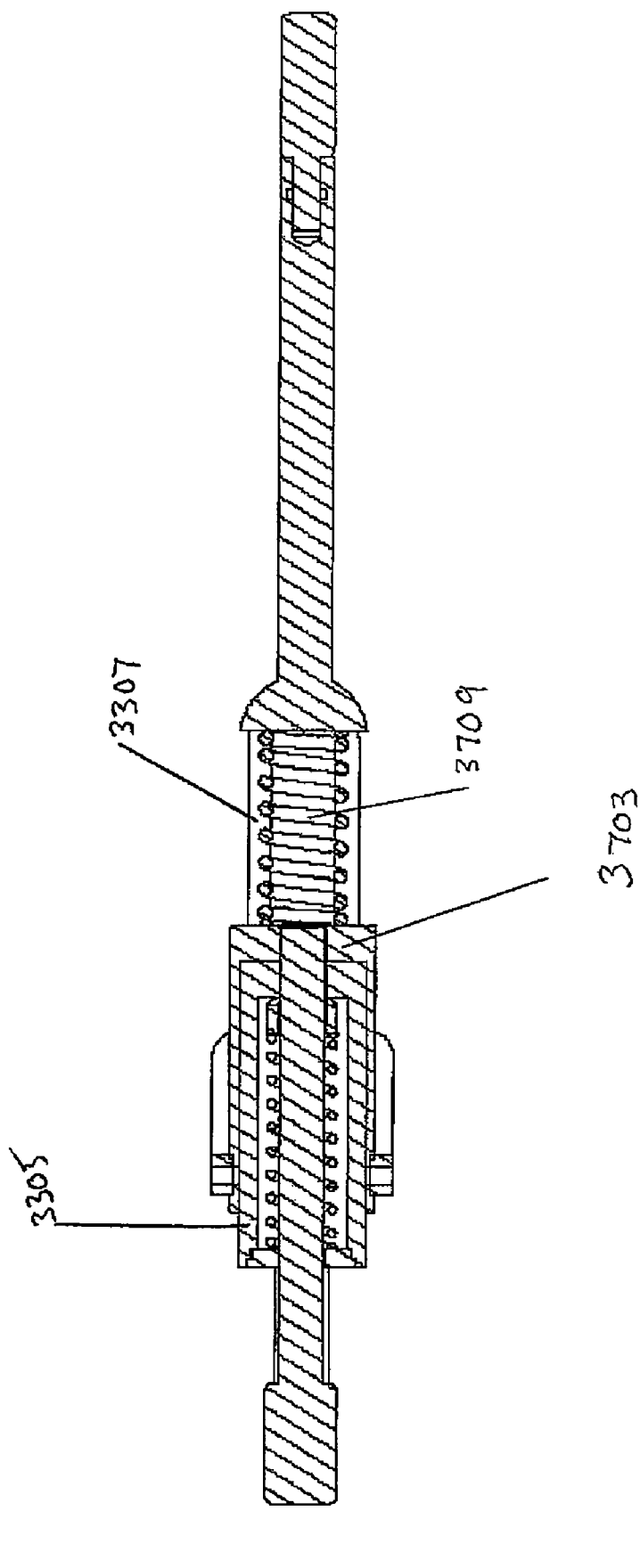
FIG. 62 is a top sectional view of the third embodiment of the pistol grip tensioning apparatus in the initial condition.
Figure 63:
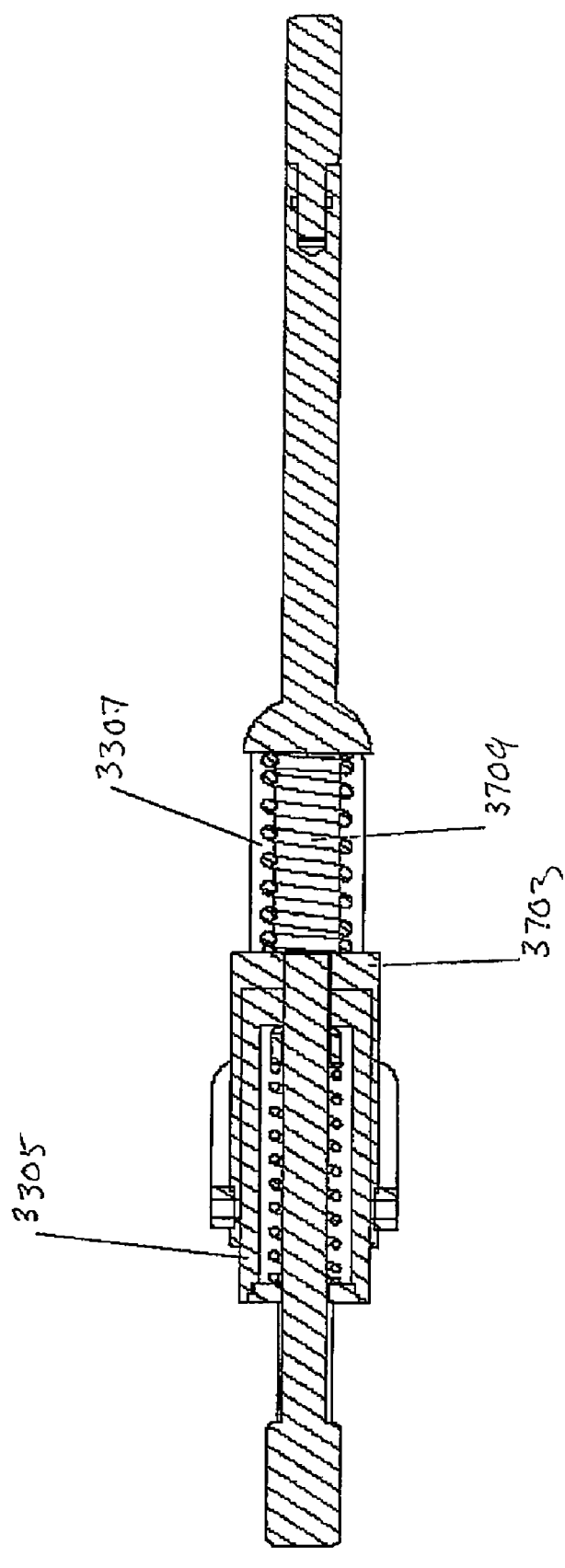
FIG. 63 is a top sectional view of the third embodiment of the pistol grip tensioning apparatus in the fully extended condition.
Figure 64:
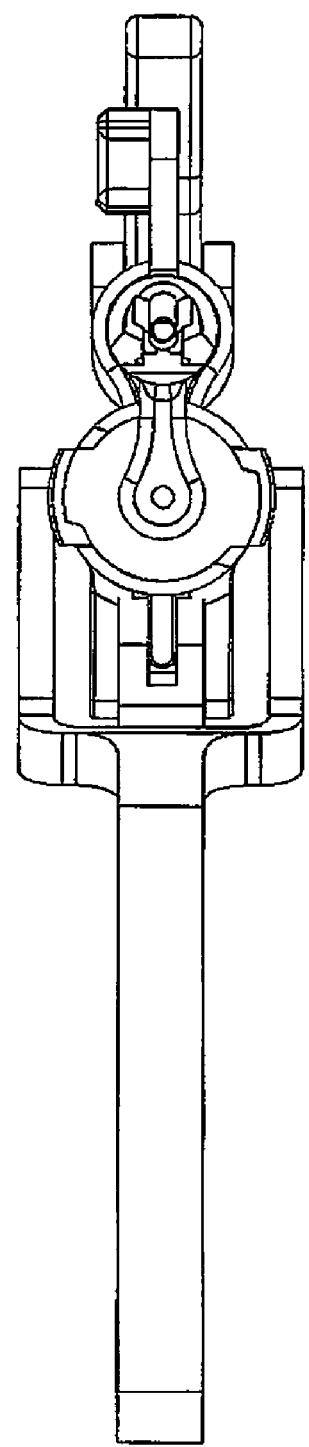
FIG. 64 is a right side view of the third embodiment of the pistol grip tensioning apparatus in the initial condition.
Figure 65:
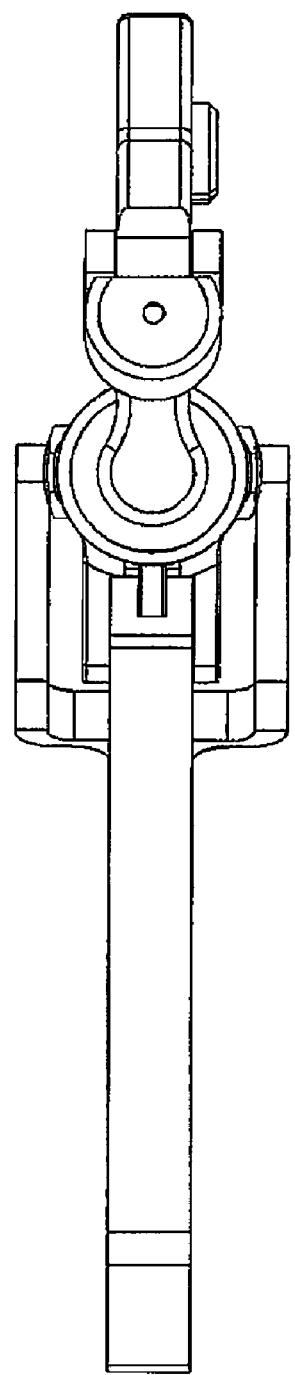
FIG. 65 is a left side view of the third embodiment of the pistol grip tensioning apparatus in the initial condition.
Figure 66:
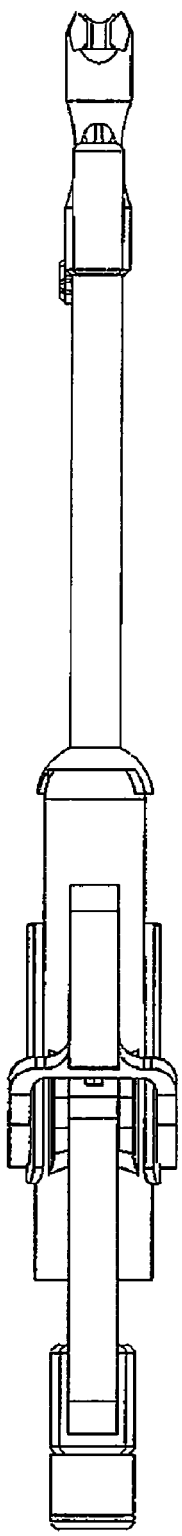
FIG. 66 is a bottom view of the third embodiment of the pistol grip tensioning apparatus in the initial condition.
Figure 67:
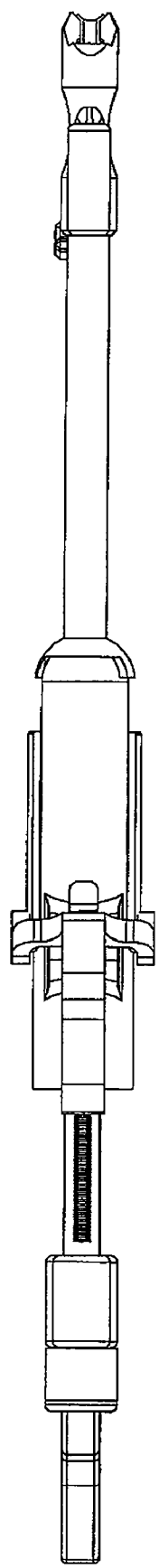
FIG. 67 is a bottom view of the third embodiment of the pistol grip tensioning apparatus in the fully extended condition.

The ducts 3303 and 3307 or flow ports feature of the third embodiment 3001 of the cable tensioning apparatus 3001 are more limited. As shown in FIGS. 54 and 55, the distal housing duct 3307 of the third embodiment 3001 provides access for flushing of the calibrated compression spring 3709. The housing duct 3307 allows cleaning solution to be flushed straight into the housing structure 3305, through the coils of the compression spring 3709, and continue out of the housing structure 3305 as shown in FIGS. 62 and 63.

Figure 72:
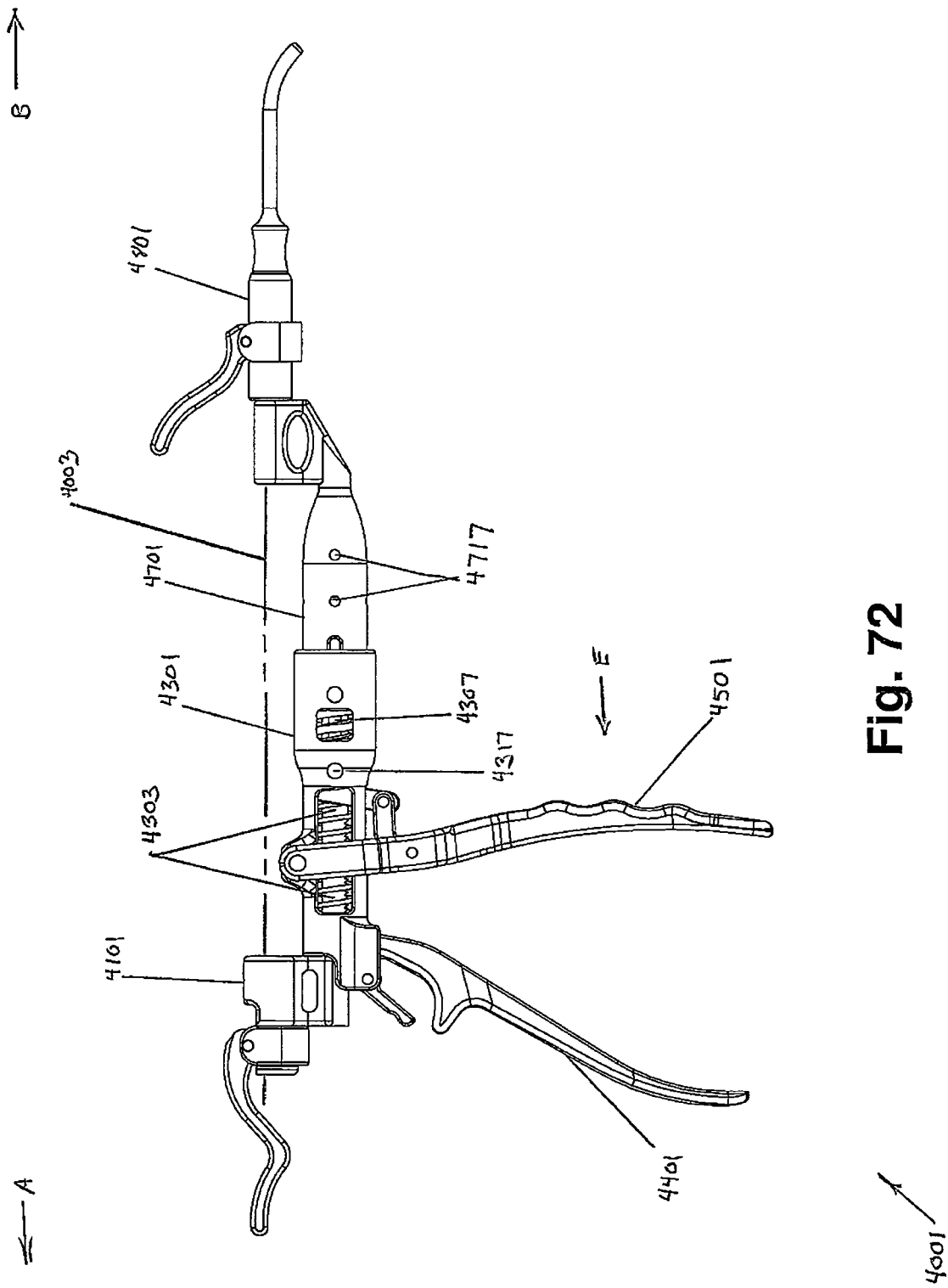
FIG. 72 is a front view of the fourth embodiment of the pistol grip tensioning apparatus in the initial condition.

The ducts 4303, 4307, 4717 or flow ports feature of the fourth apparatus 4001 of the cable tensioning apparatus 4001 are more expansive. As shown in FIGS. 70 and 72, the duct 4303 has been retained from the first two embodiments and the distal housing duct 4307 has been enlarged. In addition, indicator ducts 4717 have been added in the fourth embodiment 4001 because the fourth apparatus 4001 does not allow for disassembly.

Hygiene is improved by all of the aforementioned cleanability design features because tissue or biologic materials should be removed because prions or slow viruses within tissue or biologic materials cannot be sterilized by most conventional sterilization techniques or processes. Certain infectious agents, such as prions or other slow viruses, are difficult to neutralize with standard sterilization techniques such as autoclaves and can carry the fatal Creutzfeldt-Jakob disease (CJD). The risk of infection from tissue or bio-mater creates many attendant costs in mitigating the risk of infection, i.e. the tracking of patients and subsequent risk of liability from an infection.

Universal Applicability

Figure 51:
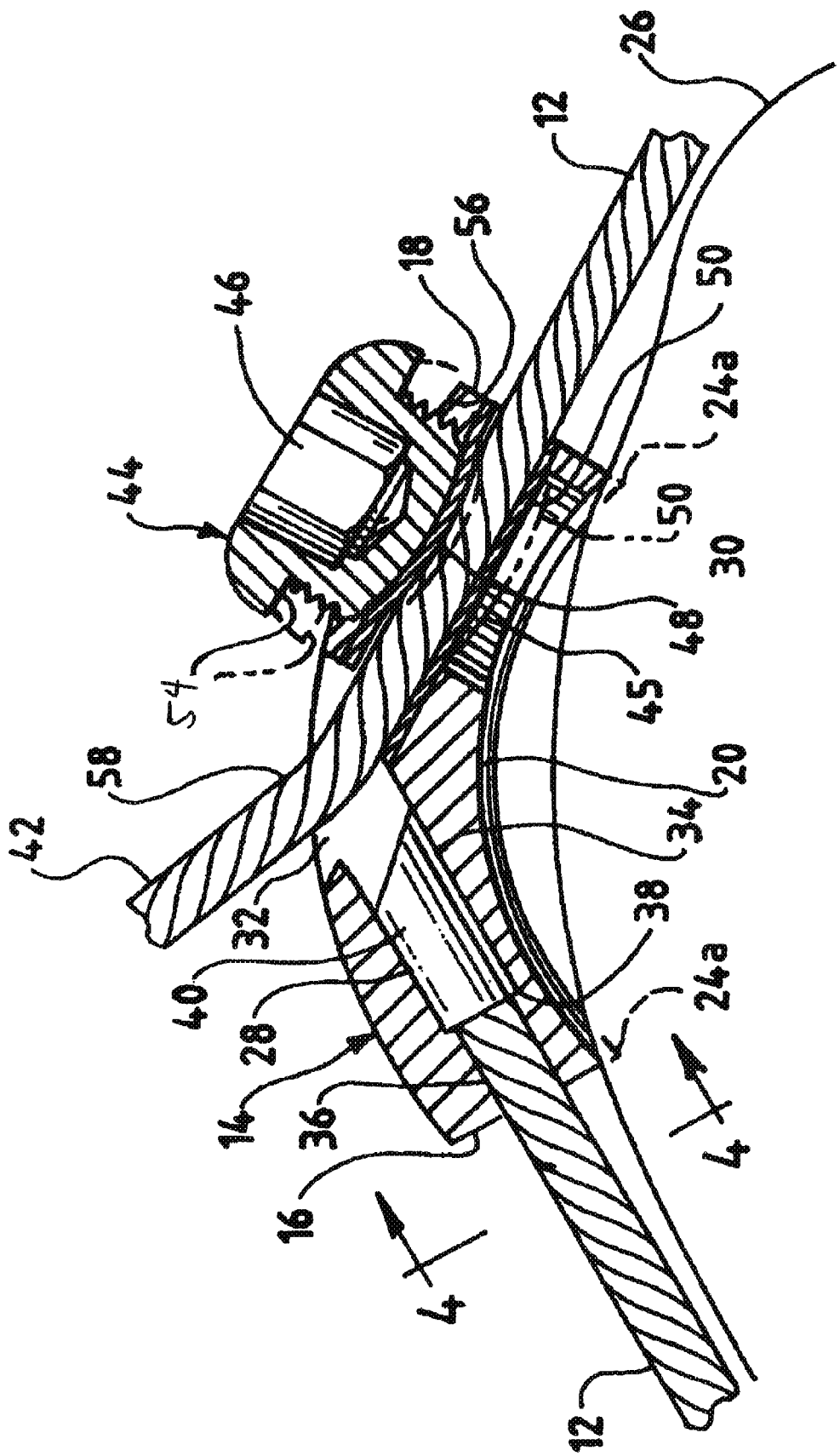
FIG. 51 is a longitudinal sectional view of the connector of FIG. 45, showing its position with a cable loop on a portion of a bone of a patient (which corresponds to FIG. 3 in U.S. Pat. No. 5,415,658).

A key feature of the pistol grip tensioning apparatus 1001, 2001, 3001, and 4001 is its near universal applicability with any type of surgical cable. The surgical cable 12 shown in FIG. 46 though FIG. 51 is hereinafter defined to be any type of surgical cable or wire that is operable within the pistol grip tensioning apparatus 1001, 2001, 3001, and 4001. For example, surgical cable 12 consisting of braided stainless steel, cobalt chrome, or titanium can be used such as described in U.S. Pat. No. 6,605,091 with Ser. No. 09/608,536 filed Jun. 30, 2000 and entitled "Surgical Cable Assembly And Method" which is incorporated herein by reference in its entirety. Alternatively, the surgical cable 12 can be made from other biocompatible materials such as synthetic polymer fibers such as polyglycolic acid (P.G.A.) or polydioxanone (PDS) in monofilament or braided configurations. Alternatively, the ultra-high molecular weight polyethylene (UHMWPE) fiber sold under the name SecureStrand described in U.S. Pat. No. 5,456,722 with Ser. No. 100,458 filed Jul. 30, 1993 and entitled "Load Bearing Polymeric Cable" could also be used and is incorporated herein by reference in its entirety. However, even gut sutures could possibly be used.

Similarly, the pistol grip tensioning apparatus 1001, 2001, 3001, and 4001 has its near universal operability with any type of crimp or surgical connector 10. The surgical connector 10 shown in FIG. 46 though FIG. 51 is only one example of many types of crimps or surgical connectors that can be used with the pistol grip tensioning apparatus 1001, 2001, 3001, and 4001. The crimp or surgical connector 10 shown in FIG. 46 though FIG. 51 is described in U.S. Pat. No. 5,415,658 with application Ser. No. 167,542 filed Dec. 14, 1993 and entitled "Surgical Cable Loop Connector" which is incorporated herein by reference in its entirety.

However, almost any kind of crimps or surgical connector 10 can be used with the pistol grip tensioning apparatus 1001, 2001, 3001, and 4001. Surgical connector 10 is hereinafter defined to be any type of surgical connector or crimp that is operable with pistol grip tensioning apparatus 1001, 2001, 3001, and 4001. For example, the crimp or surgical connector (not shown) described in U.S. Pat. No. 6,605,091 B1 with application Ser. No. 09/608,536 filed Jun. 30, 2000 and entitled "Surgical Cable Assembly And Method," can be used and is incorporated herein by reference in its entirety. In addition, the crimp or surgical connector described in U.S. Pat. No. 5,649,927 (not shown) with application Ser. No. 534,783 filed Sep. 27, 1995 and entitled "Cable Crimp System" can be used and is also incorporated herein by reference in its entirety. Also, the crimp described in U.S. Pat. No. 5,741,260 with application Ser. No. 803,503 filed Feb. 20, 1997 and entitled "Cable System For Bone Securance" can be used and is incorporated herein by reference in its entirety. Alternatively, almost any type of crimp or surgical connector for cable or wire can be used with the pistol grip tensioning apparatus 1001, 2001, 3001, and 4001 because of the cable pensioner's near universal applicability.

Offset Cable Passage

The offset cable race 1003, 3003, and 4003 is another feature which improves cleanability but also the rapidity of operation for the first, third and fourth embodiments of the cable tensioning apparatus 1001, 3001 and 4001. The offset cable race 1003, 3003, and 4003 for the apparatus 1001, 3001 and 4001 is generally more cleanable because most of the surgical cable 12 passes externally with open access for cleaning. Operation of the apparatus 1001, 3001 and 4001 is generally more rapid because surgical cable 12 can be rapidly "pre-tensioned" to eliminate any slack in the cable 12 to greatly increase the pace of the surgery itself.

Figure 6:
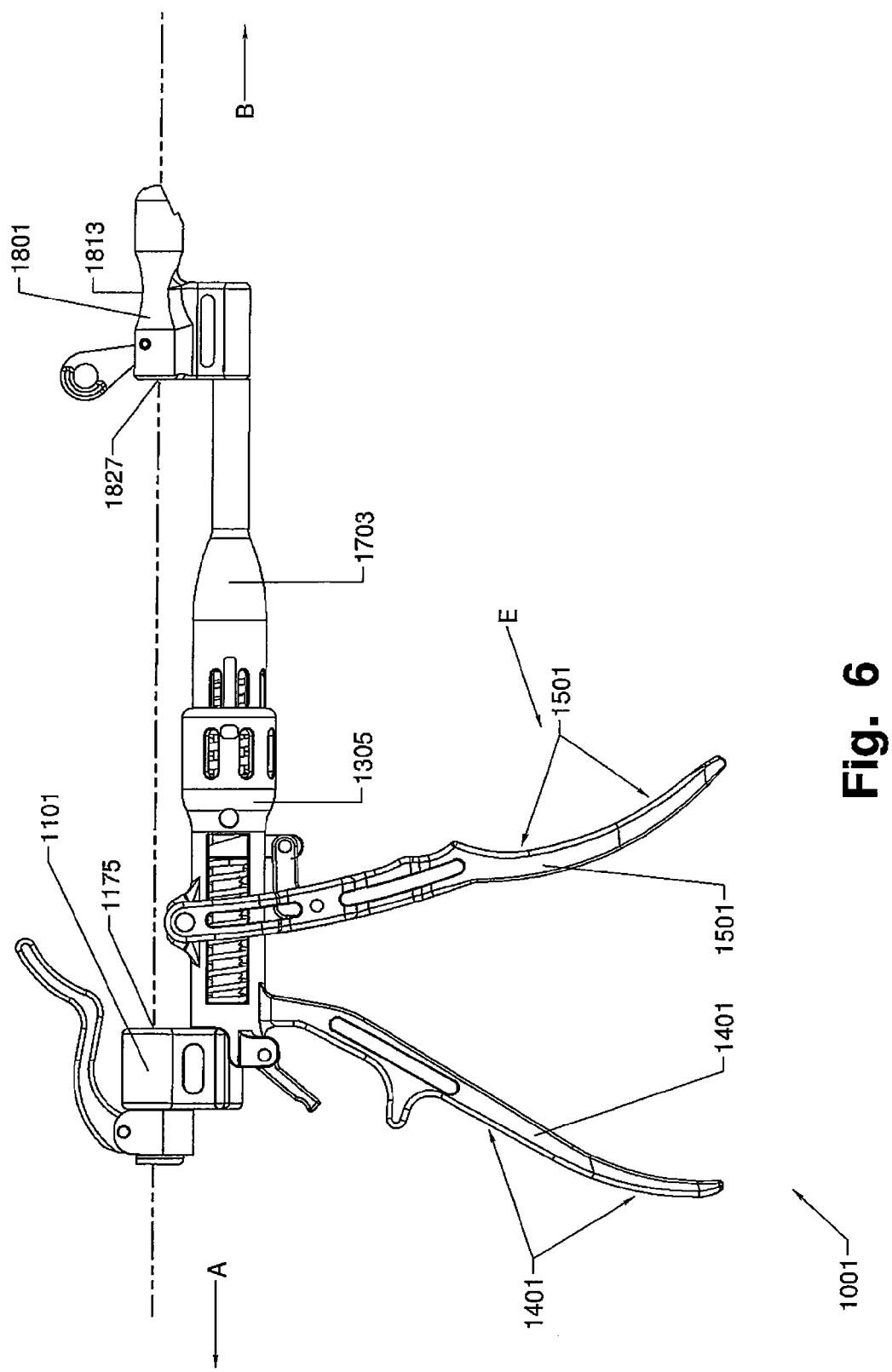
FIG. 6 is a front view of the first embodiment of the pistol grip tensioning apparatus in the initial condition.
Figure 12:
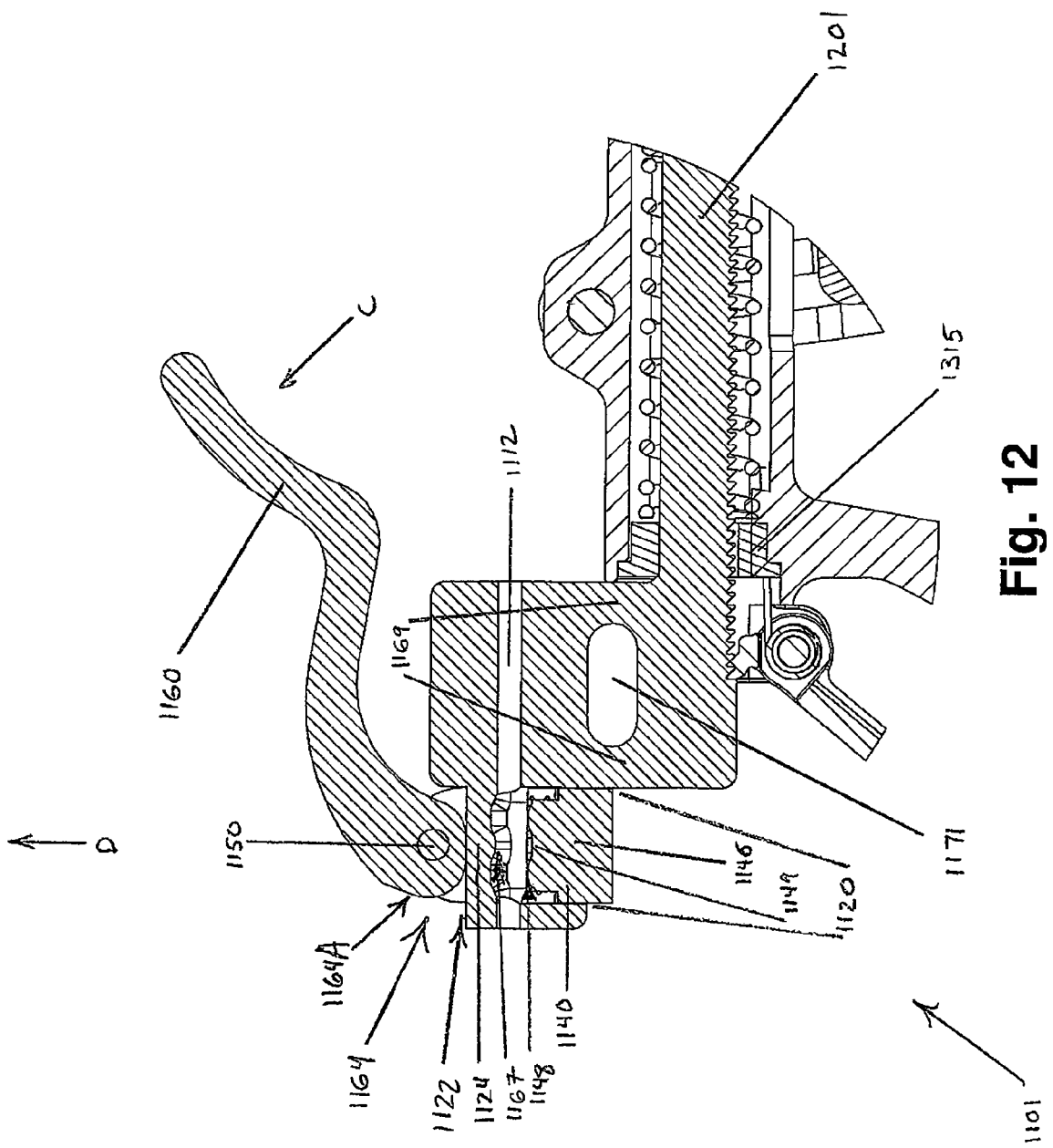
FIG. 12 is a detailed front sectional view of the proximal cable clamp assembly of the first embodiment of the pistol grip tensioning apparatus in the initial condition.

FIG. 6 helps show an example of the enhanced cleanability of the complete offset cable race 1003 shown as the phantom line. The surgical cable 12 is inserted within the offset cable race 1003 to tension the cable 12. As shown in FIG. 6, only the portions of the cable 12 that run within the proximal cable clamp assembly 1101 and the distal cable clamp assembly 1801 require flushing of internal components for sterilization. The short distance of the proximal cable clamp passage 1112 within the proximal cable clamp assembly 1101 allows jets of cleaning solution to maintain high pressure because of the elimination of friction loss from long distances as shown in FIG. 12. The low friction losses from the short passage 1112 also allow high flow volumes of cleaning solution with in the passage 1112.

Figure 18:
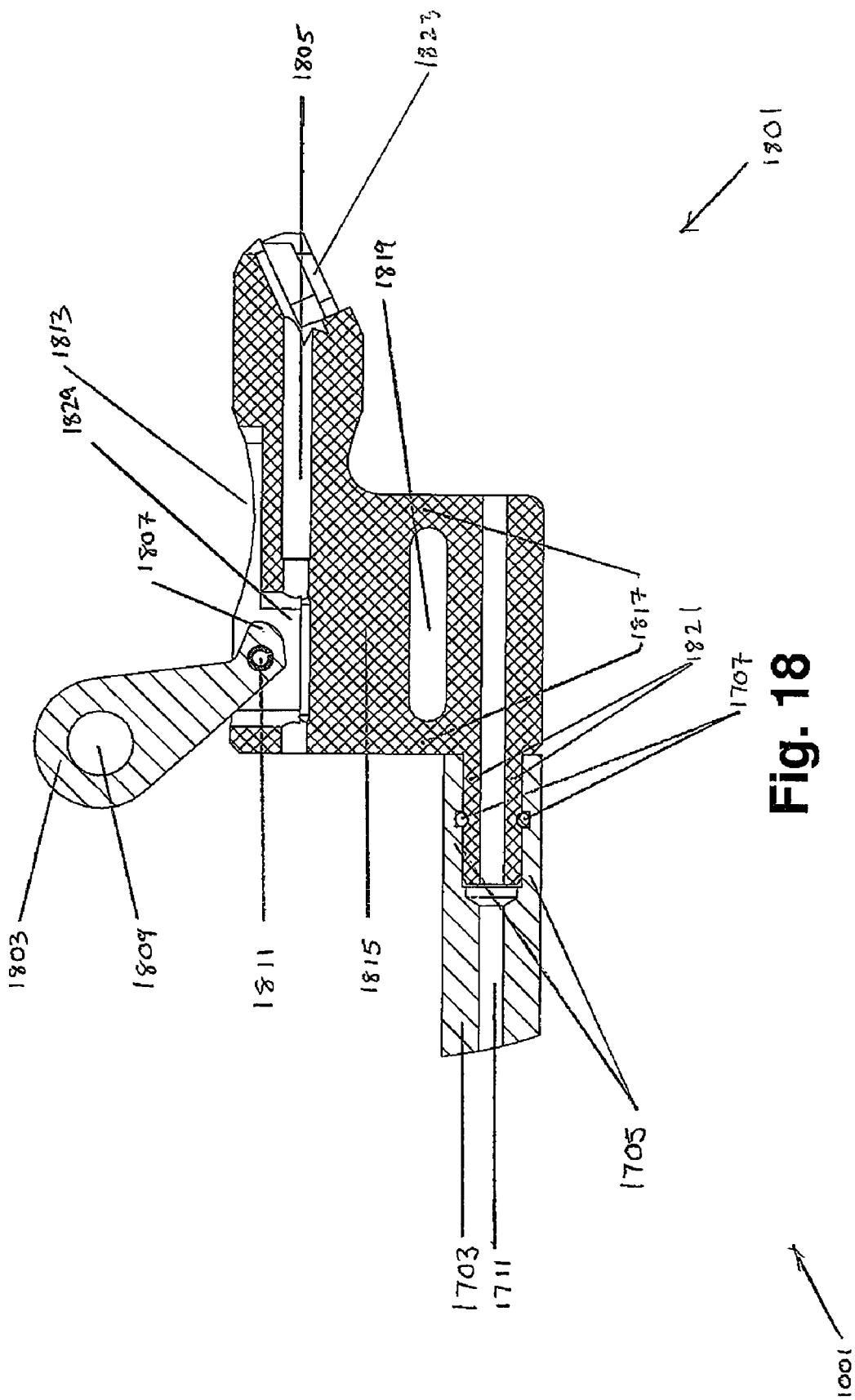
FIG. 18 is a detailed front sectional view of the distal cable clamp assembly in the first embodiment of the pistol grip tensioning apparatus in the initial condition.

Similarly, as shown in FIG. 18, the short distal cable clamp passage 1805 in the distal cable clamp assembly 1801 allows high pressure washing both through the passage 1805 but also through the cam lever access port 1829. Finally, the housing structure 1305 and the indicator structure 1703 protect the bulk of the internal workings of the cable tensioning apparatus 1001 by shielding internal components from contamination due to debris from biologic materials adhering to the surgical cable 12.

Figure 45:
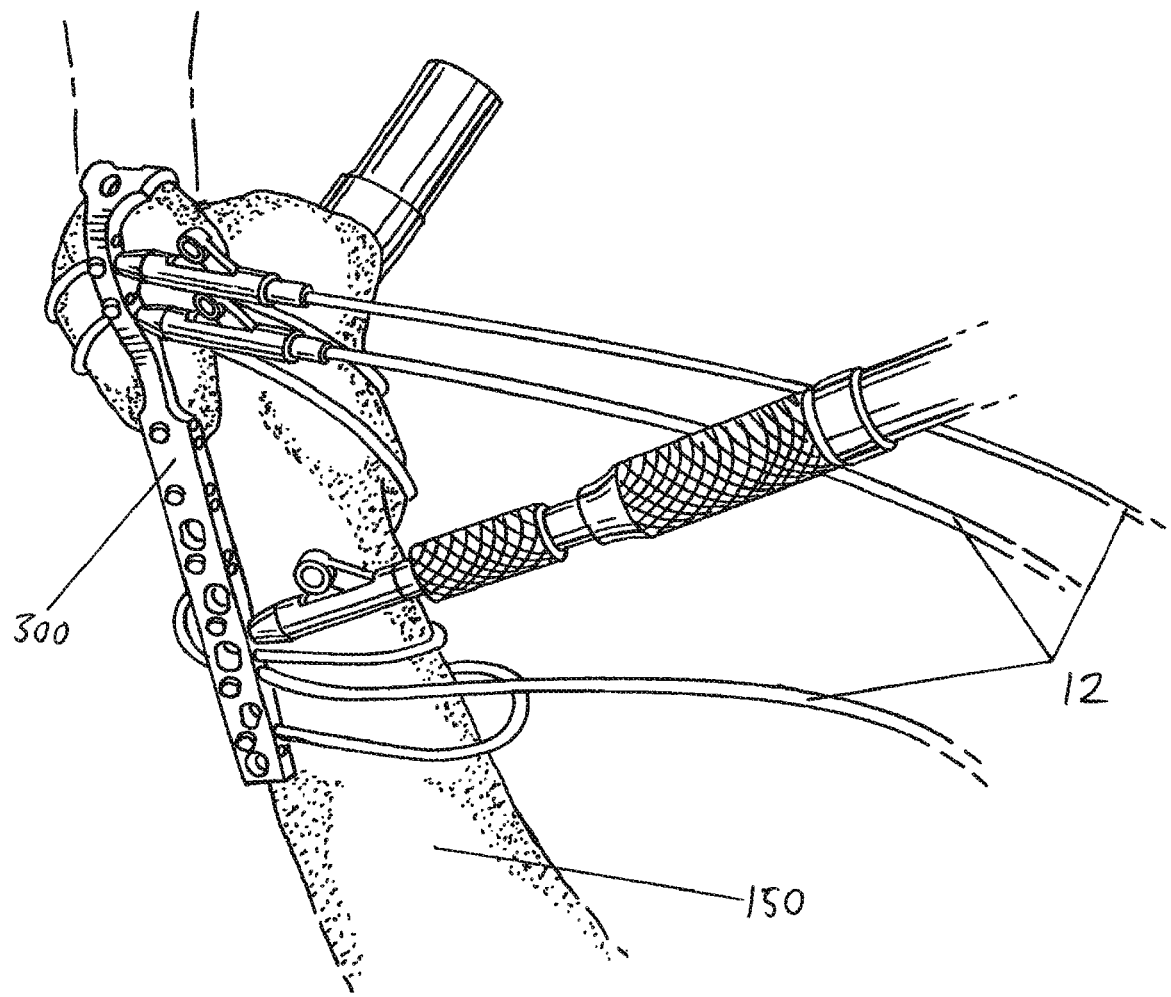
FIG. 45 is an illustration of the surgical procedure which utilizes the distal cable clamp assembly of the second embodiment of the pistol grip tensioning apparatus (which corresponds to FIG. 11 in U.S. Pat. No. 7,207,993 B1).

FIG. 6 shows the enhanced rapidity of "pre-tensioning" of the offset cable race 1003 shown as the phantom line. As shown in FIG. 6, the proximal and distal cable clamp assemblies 1101 and 1801 are shown in the unlocked position to allow surgical cable 12 to pass through the clamp assemblies 1101 and 1801 along the dashed phantom lines. A significant amount of excess cable 12 or slack is present when passing cable 12 into position within the cable tensioning apparatus 1001, 2001, 3001, and 4001 as shown in FIG. 45. The surgeon can remove excess cable 12 or slack when the surgical cable 12 is not yet under significant tension within the apparatus 1001, 2001, 3001, and 4001. The surgeon can simply manually pull the cable 12 for the portions of the cable 12 that are not within the clamp assemblies 1101 and 1801 until the cable 12 is in the desired position and thus "pre-tension" the apparatus.

An example of utilizing cable 12 with a trochanter connector 300 with an implant is illustrated in FIG. 45. As shown in FIG. 45, a significant amount of excess cable 12 or slack can be present in the surgical cable 12 when used with an implant, for example, a trochanter connector 300 used to repair a femur 150 or upper leg bone. The advantage of "pre-tensioning" the surgical cable 12 is illustrated in FIG. 45 because of the long loops of cable 12. As shown in FIG. 45, the trochanter connector 300 requires that the cable 12 to be looped several times around the femur 150 creating a significant amount of excess cable 12 or slack. Little force is required to eliminate the excess slack when the cable 12 is positioned around the femur 150. The cable tensioning apparatus 1001, 2001, 3001, and 4001 takes advantage of this circumstance where little force is required to eliminate slack by providing the offset clamp assemblies allow the rapid manual "pre-tensioning" of the cable 12.

The surgical procedure which utilizes the trochanter connector 300 to secure and support the femur 150 is described in further detail in U.S. Pat. No. 7,207,993 B1 with Ser. No. 09/775,891 filed Feb. 2, 2001 and entitled "Apparatus and Method for Repairing the Femur" which is incorporated by reference in its entirety herein. It should be noted that surgical cable 12 is used in many surgical procedures to repair bones such as the radius or tibia of the arm in conjunction with plates. The aforementioned U.S. Pat. No. 7,207,993 B1 should not be construed to limit the number of surgical applications of the cable tensioning apparatus 1001, 2001, 3001 and 4001. The "Apparatus and Method for Repairing the Femur" is merely used to illustrate as an example a procedure using the cable tensioning apparatus 1001, 2001, 3001 and 4001.

Figure 7:
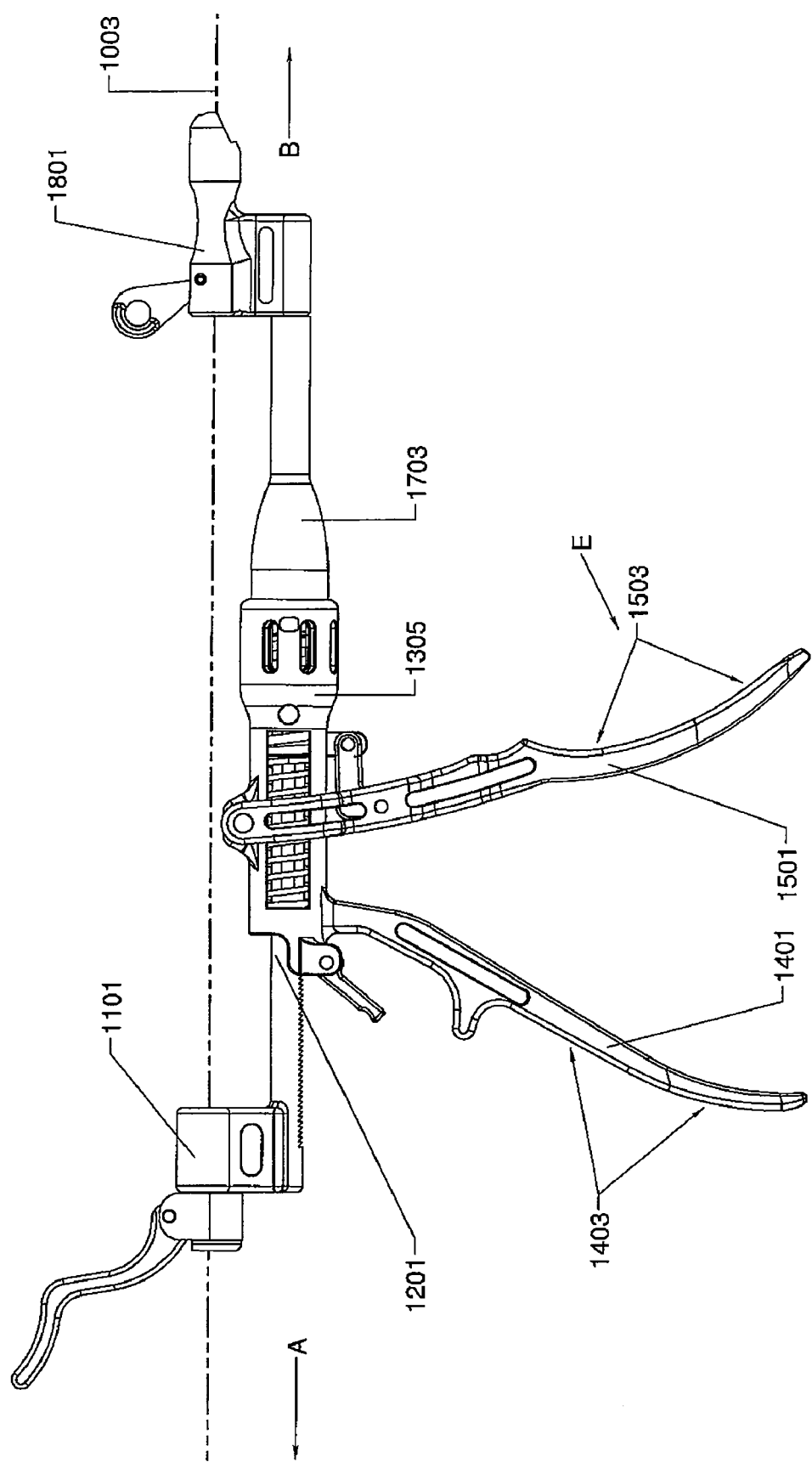
FIG. 7 is a front view of the first embodiment of the pistol grip tensioning apparatus in the fully extended condition.

FIG. 7 shows the enhanced rapidity of the offset cable race 1003 shown as the phantom line. As shown in FIG. 7, the proximal cable clamp assembly 1101 is shown in the locked position to lock the surgical cable 12 to the proximal cable clamp assembly 1101. As the drive rod 1201 is driven in the rearward or proximal direction A by depression or pulling of the lever 1501 in direction E, the surgical cable 12 to passes through the distal cable clamp assembly 1801. As the cable 12 passes through the offset distal clamp assembly 1801, the operator can adjust the cable 12 anywhere along the phantom line in the event of inadvertent mechanical interference from the distal cable clamp assembly 1801 or the housing structure 1305. The drive rod 1201 is driven in the proximal direction A until the rod 1201 is fully rearwardly extended as shown in FIG. 7.

Figure 8:
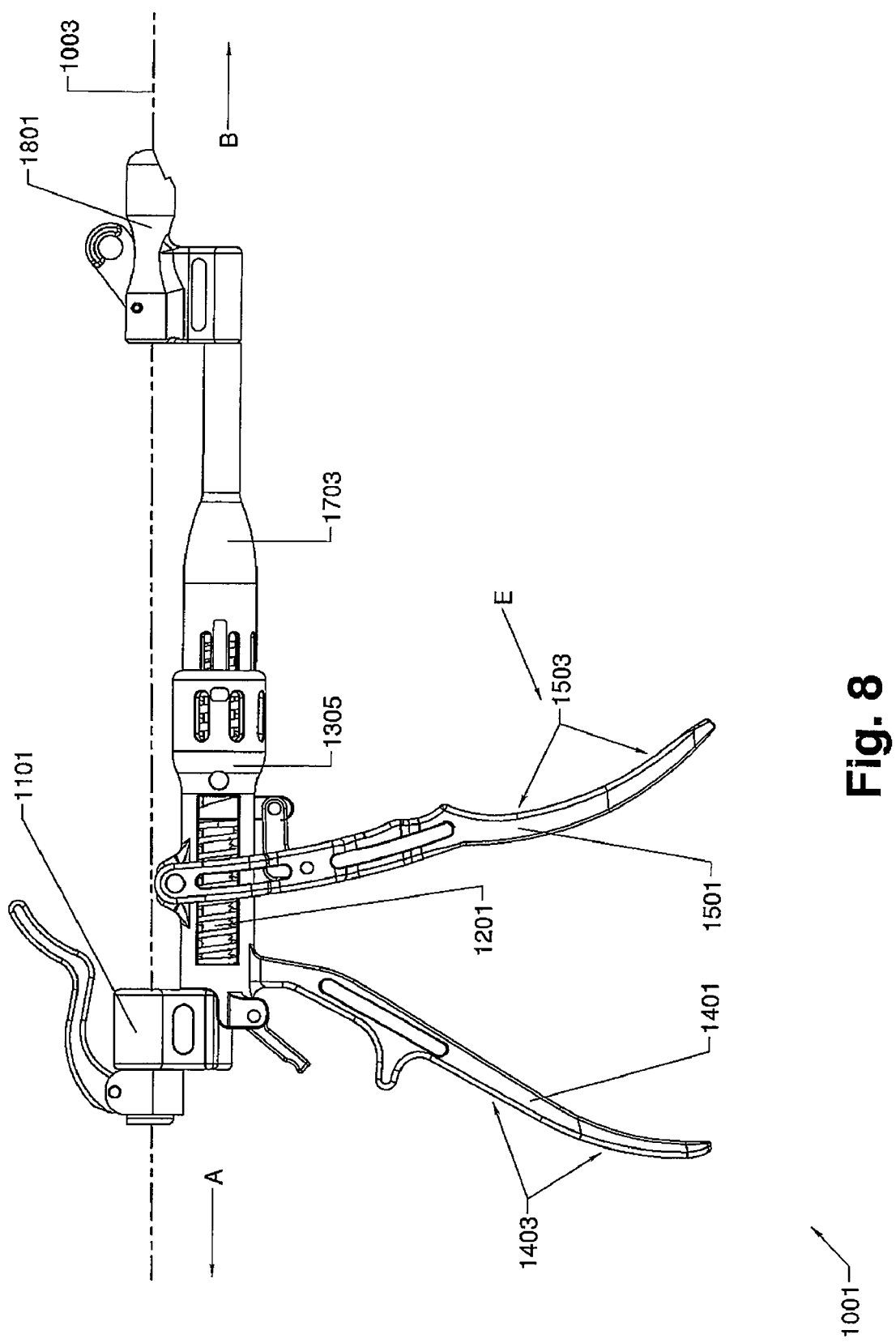
FIG. 8 is a front view of the first embodiment of the pistol grip tensioning apparatus in the secured or locked configuration.

FIG. 8 also shows the improved visualization of the cable tensioning process provided by the offset clamp assemblies 1101 and 1801 during the resetting of the tensioning process. The proximal clamp assembly 1101 in the unsecured or unlocked configuration and distal cable clamp assembly 1801 in the secured or locked configuration allow the drive rod 1201 to be reset from the extended position to the initial position as shown in FIG. 8. During the resetting of the drive rod 1201, a significant amount of excess cable 12 or slack can develop between the cable entrance 1175 and the cable exit 1827 depending upon the amount of friction created in the proximal cable clamp passage 1112 as the rod 1201 travels or translates back in the forward or distal direction B. The surgeon can visually see and tactilely feel the cable 12 position during the resetting process to detect errors or slack as a result of inadvertent mechanical interference. Any such errors, such as snags or "hang ups", can often be readily cleared by simple manual adjustments of the operator.

Figure 16:
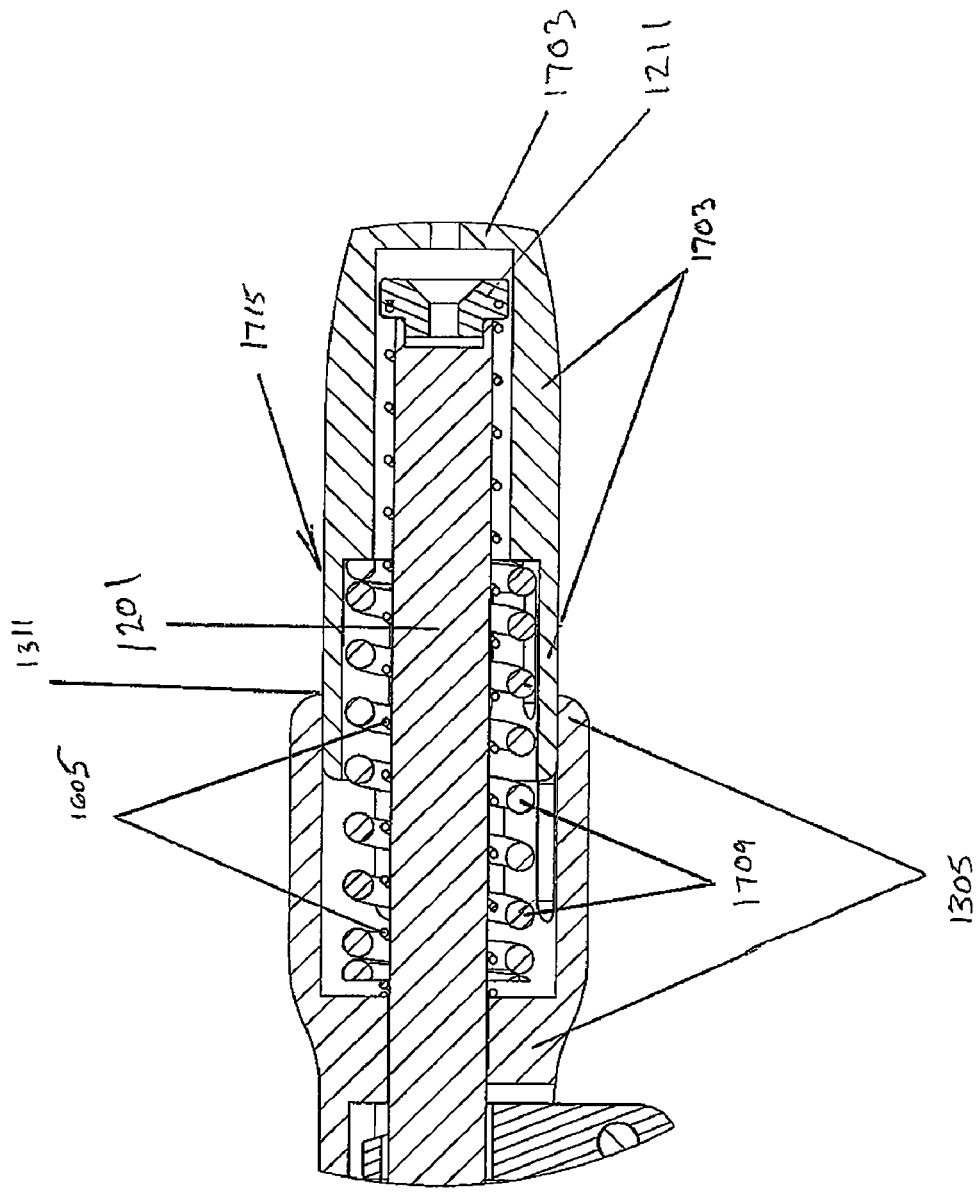
FIG. 16 is a detailed front sectional view of the tension indicator mechanism of the first embodiment of the pistol grip tensioning apparatus in the initial condition.
Figure 59:
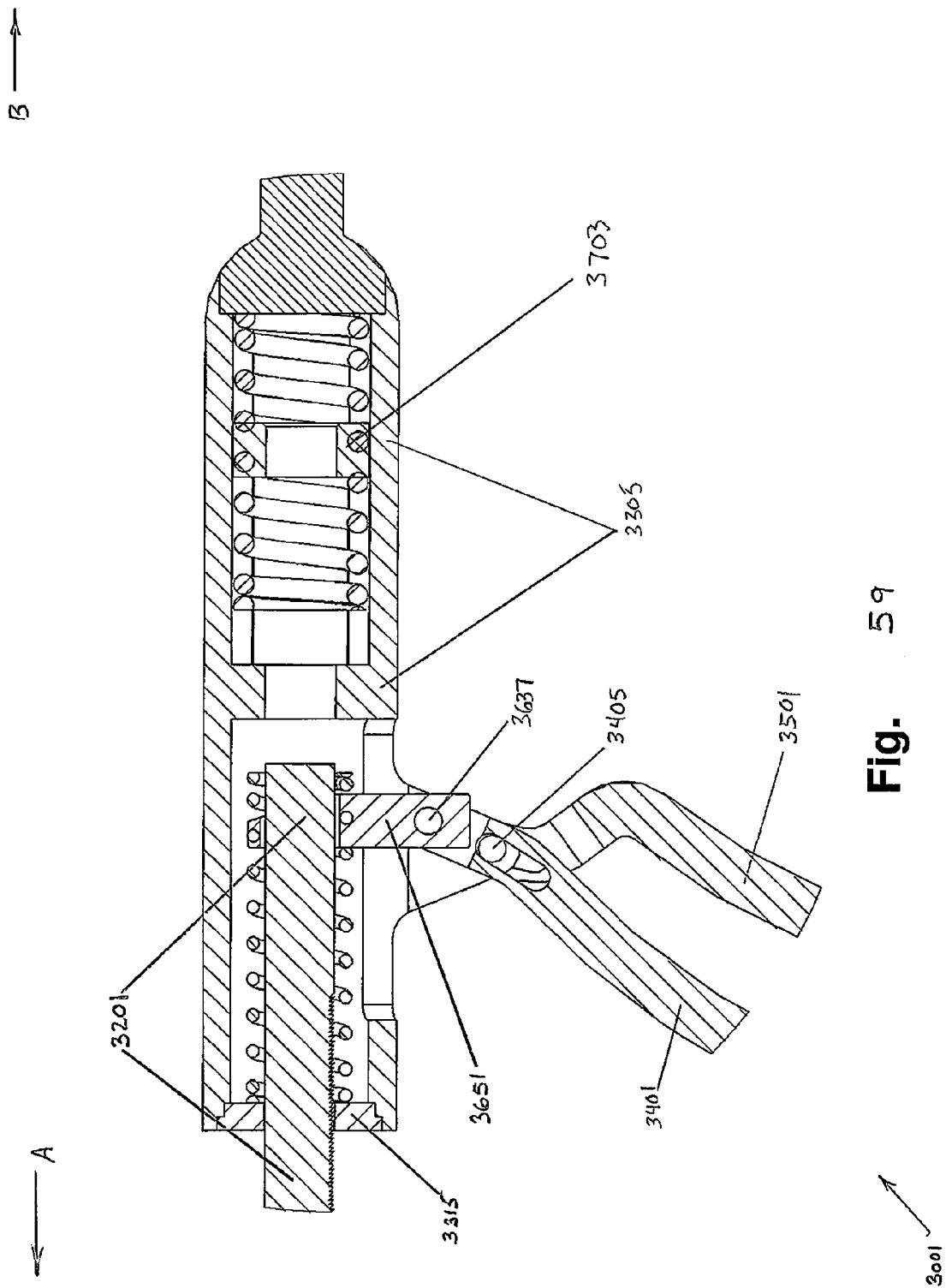
FIG. 59 is a detailed front sectional view of the drive mechanism of the third embodiment of the pistol grip tensioning apparatus in the fully extended condition.
Figure 60:
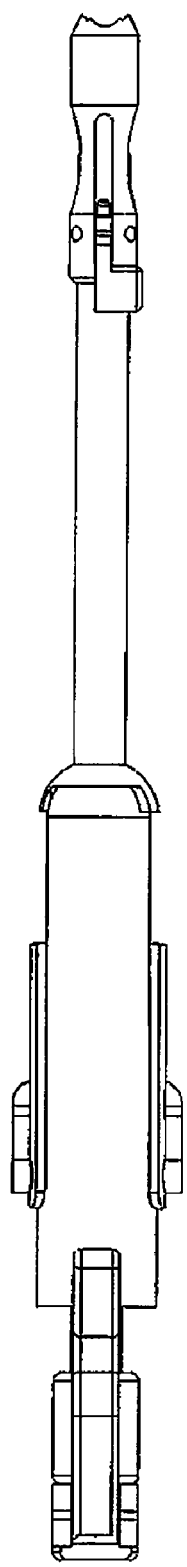
FIG. 60 is a top view of the third embodiment of the pistol grip tensioning apparatus in the initial condition.
Figure 61:
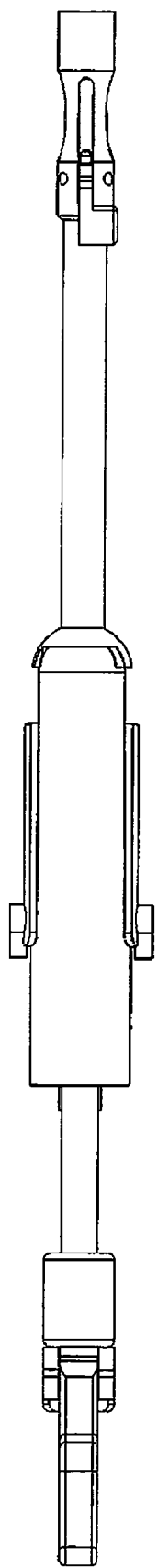
FIG. 61 is a top view of the third embodiment of the pistol grip tensioning apparatus in the fully extended condition.
Figure 80:
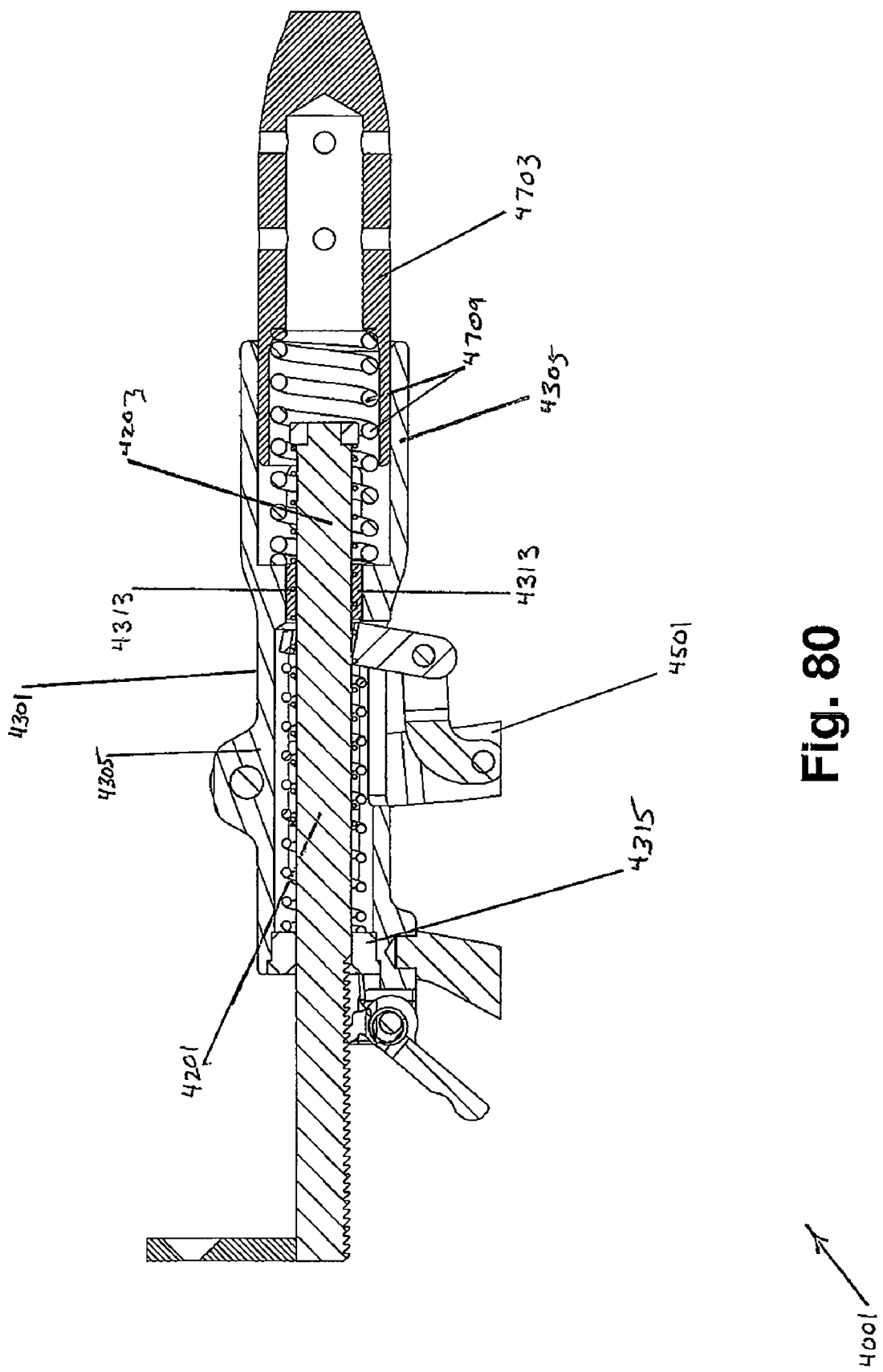
FIG. 80 is a detailed front sectional view of the drive mechanism of the fourth embodiment of the pistol grip tensioning apparatus in the fully extended condition.

However, the advantages of the offset cable clamp assemblies 1101, 1801, 3101, 3801, 4101, and 4801 were only achieved with mechanical innovations to accommodate the improved approach of the offset clamp assembly design. The superior operational results were not predictable because it was not expected that the drive mechanism 1601, 2601, and 4601 would function under the high bending moment created by offset distance K of the offset cable clamp assemblies 1101, 1801, 4101, and 4801 and the tensile force of the surgical cable 12. The offset distance K shown in FIGS. 9, 10, 11, 56, 57, 75, 76, and 77 creates a mechanical bending moment within the cable tensioning apparatus 1001, 3001 and 4001 as a result of the tensile force exerted on the surgical cable 12. The bending moment creates friction in the shifting between the housing structure 1305, 3305, 4305 and the indicator structure 1703, 3703, 4703 as shown in FIGS. 16, 59 and 80. The friction in turn creates the potential for galling or welding of the high points of the metal which cause stoppage or ceasing between the housing structure 1305, (or 3305, 4305) and the indicator structure 1703, (or 3703, 4703). The friction also creates the potential of friction induced mechanical interference or mechanical stoppage of the indicator mechanism 1701, 3701, 4701 because the high normal forces may cause ceasing or mechanical interference thereby preventing the indicator structure 1703, 3703, 4703 from shifting within the housing structure 1305, 3305, 4305. To prevent the potential stoppage of the mechanical operation of the indicator mechanism 1701, (or 3701, 4701) the indicator structure 1703, (or 3703, 4703) is made from gall-resistant stainless steel.

The pistol grip cable tensioning apparatus 1001, 3001 and 4001 takes advantage of metallurgical innovations by utilizing gall-resistant stainless steels for proper functioning which were not widely commercially available previously. Commercially available gall-resistant metals such as the super alloy Nitronic 60 or Gall-Tough are utilized in the fabrication of the indicator structure 1703, 3703, and 4703. Gall-resistant stainless steels, such as Nitronic 60 or Gall-Tough, prevents the potential of galling or cold welding created by the high loading conditions caused by the bending moment created by the offset cable passage 1112, 3112, 4112 on the components of the cable tensioning apparatus 1001, 3001, 4001. In the one embodiment, gall-resistant stainless steels, such as Nitronic 60 or Gall-Tough, are used because gall-resistant steels outperform most other stainless steels in corrosion and pitting resistance. Sufficient reliability of mechanical operation is maintained by the usage of gall-resistant stainless steels, such as Nitronic 60 or Gall-Tough, with the offset race 1003, 3003, 4003 design. Alternatively, Nitronic 60 or Gall-Tough can also be utilized in the rear insert 1315, 2315, 3315, 4315 of the housing member 1301, 2301, 3301, 4301 to further reduce galling or binding as shown in FIG. 12, FIG. 35, FIG. 58, and FIG. 79.

Figure 79:
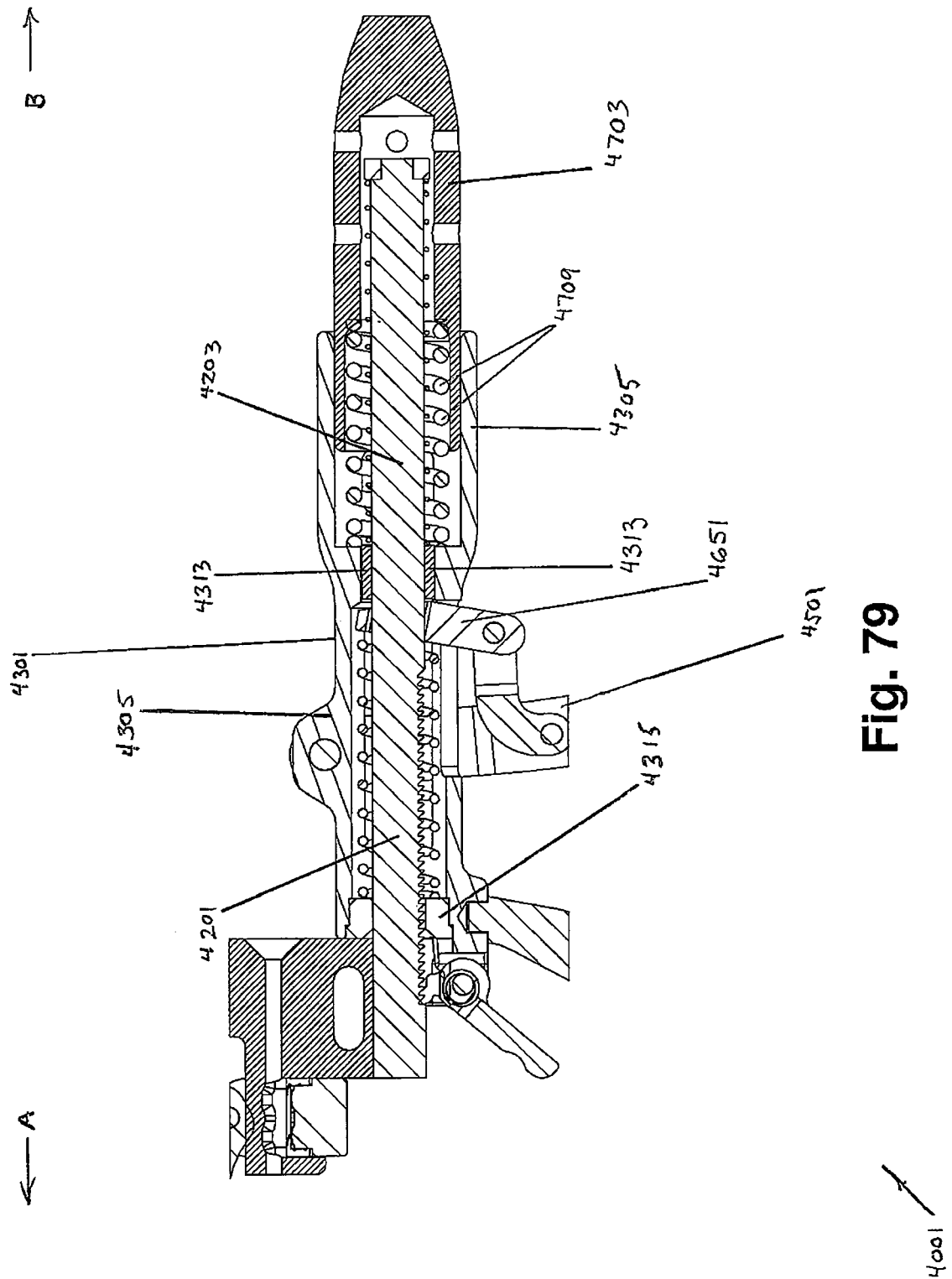
FIG. 79 is a detailed front sectional view of the drive mechanism of the fourth embodiment of the pistol grip tensioning apparatus in the initial condition.

Another mode or means to limit galling or binding is through the utilization of polyaryletheretherketone (hereinafter PEEK) as a bearing material. As shown in FIGS. 79 and 80, the bearing 4313 in the form of a PEEK bushing is centrally located in the cable tensioning apparatus 4001. The housing structure 4305 of the housing member 4301 holds the bearing 4313 in place with pins 4317 and lateral bore in the bearing 4313. Alternatively, the bearing 4313 can be held in place with epoxy or other adhesives. The cylindrical portion 4203 of the drive rod 4201 shifts in the proximal and distal direction A and B. The drive rod 4201 has shiftable mechanical engagement because the bearing 4313 only allows the drive rod 4201 linear motion along central longitudinal axis of housing member 4301 since the bearing 4313 has a low coefficient of static and dynamic friction.

PEEK is an appropriate material to use as a bearing 4313 because PEEK has a low coefficient of friction with excellent resistance to mechanical wear. PEEK is also a biocompatible thermoplastic to mitigate any risk of wear debris potentially entering the patient. Finally, PEEK has high chemical resistance necessitated by sterilization of the instrument 1001, 2001, 3001, and 4001. Alternatively, the bearing 4313 could utilize Gall-Tough or Nitronic 60 to reduce galling. Yet another mode to limit binding is to extend the length of components and increase bearing surfaces as was done in the fourth embodiment 4001.

The third and fourth embodiments of the cable tensioning apparatus 3001, 4001 have the same advantages of cleanability and rapidity through "pre-tensioning" as discussed above for the first embodiment 1001. The offset cable race 3003, 4003 is shown as the phantom line in FIGS. 54 and 73. The short distance of the clamp passages 3112, 3805, 4112, 4805 shown in FIGS. 56 and 75 allows efficient flushing of those passages. The housing and indicator structures 3305, 3703, 4305, and 4703 also shield internal components of the apparatus 3001, 4001 from contamination.

Enhanced rapidity can be achieved by "pre-tensioning" cable 12 both between the clamp assemblies 3101, 3801 and 4101, 4801 and between the bones and connectors. The surgeon can still visually see and tactilely feel the cable 12 position during the resetting process to detect errors or slack as a result of inadvertent mechanical interference.

The only significant difference in operation between the first apparatus 1001 and the third apparatus 3001 is the requirement that both the handle 3401 and lever 3501 must be simultaneously squeezed while the cable clamp assemblies 3101 and 3801 are adjusted. The third embodiment 3001 does not have the ability of the first embodiment 1001 of being able to depress the lever 1501 and having the release mechanism preventing travel in the distal direction.

The improvements in the design approach of the offset cable race 1003, 3003, and 4003 provided the functional improvements of rapidity of operation and cleanability. The increased rapidity of operation is multiplied by each cable 12 that is to be tensioned by the cable tensioning apparatus 1003, 3003, and 4003. The dramatic decrease in time in cable tensioning and corresponding decrease in time under anesthetic ultimately reduces complications and saves lives. The increased cleanability also saves lives because the risk of the fatal Creutzfeldt-Jakob disease (CJD) can be also dramatically reduced. The offset cable race 1003, 3003, and 4003 provides one means of clamping surgical cable and centrally locating the cable race 2003 provides an alternative means.

Centrally Located Cable Passage

The centrally located cable race 2005 is a feature that improves the reliability of mechanical operation, and allows for greater tension loading of surgical cable 12. The apparatus 2001 is generally more reliable in mechanical operation because the centrally mounted clamp assemblies 2101 and 2801 reduce the bending moment created by the tension in the cable 12 and thus reduces the risk of galling or mechanical interference. The apparatus 2001 can generally provide greater cable tension again because of the reduction of the large bending moment that allows the structural components to support a greater tension load.

Figure 29:
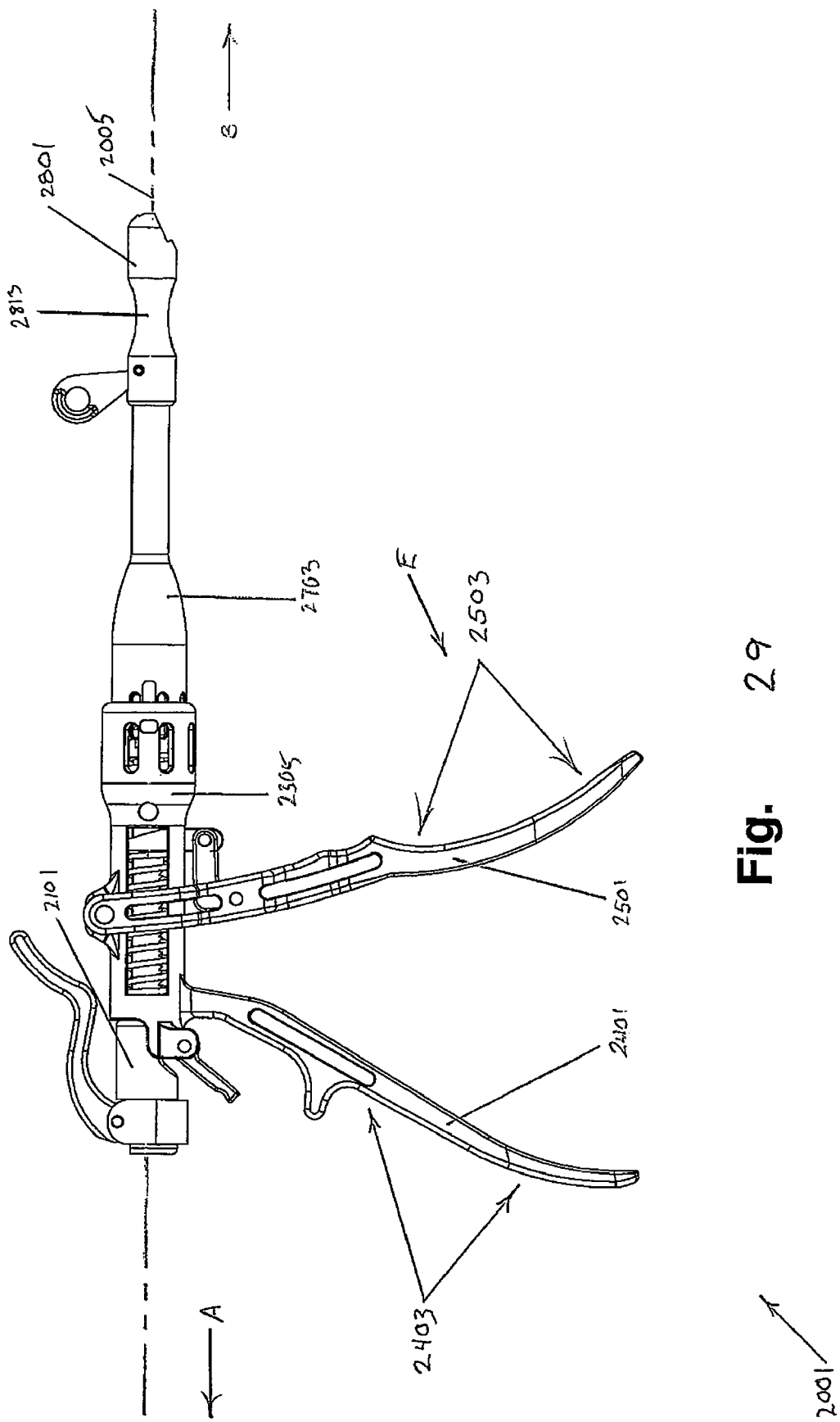
FIG. 29 is a front view of the second embodiment of the pistol grip tensioning apparatus in the initial condition.
Figure 30:
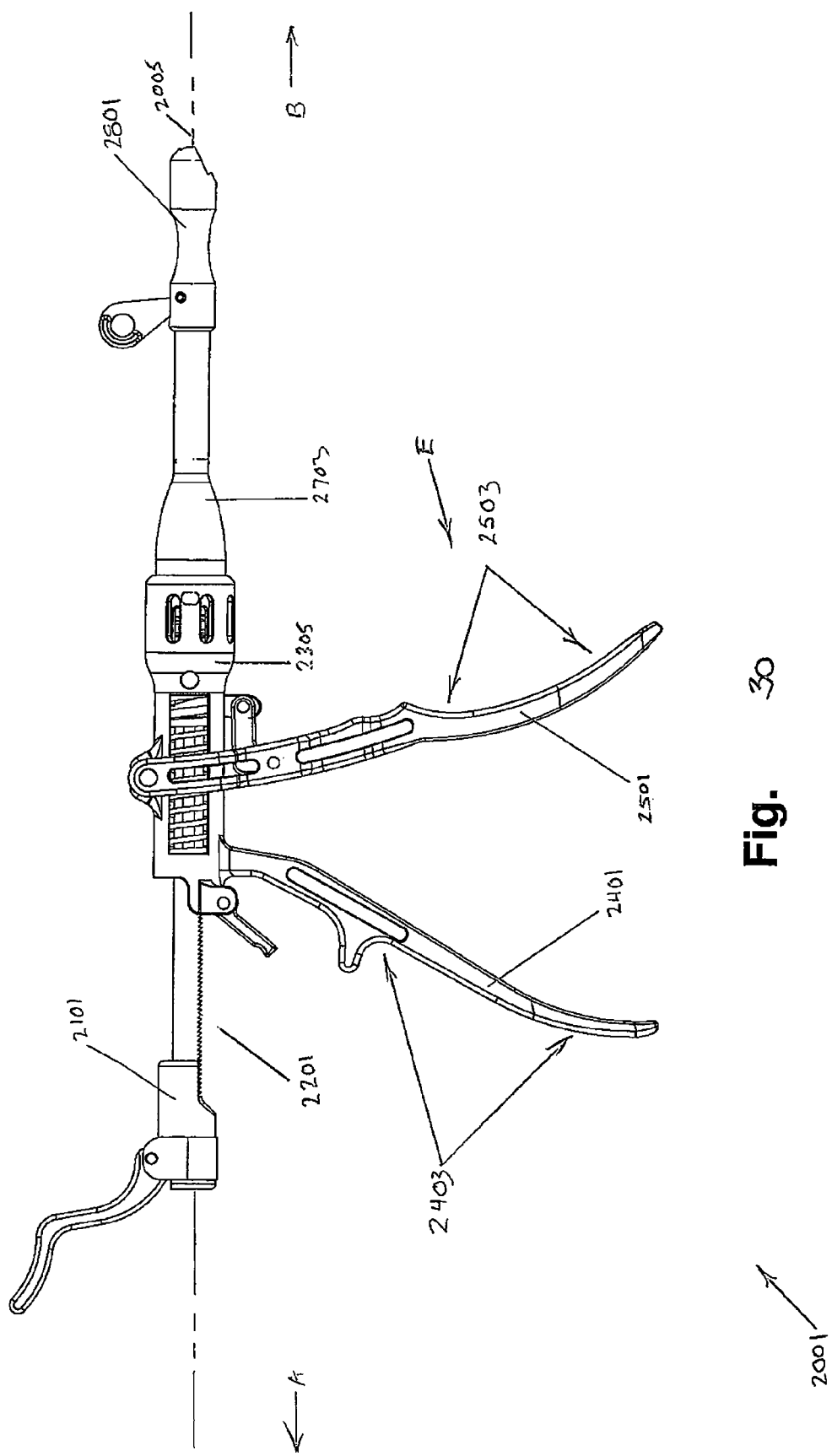
FIG. 30 is a front view of the second embodiment of the pistol grip tensioning apparatus in the fully extended condition.
Figure 31:
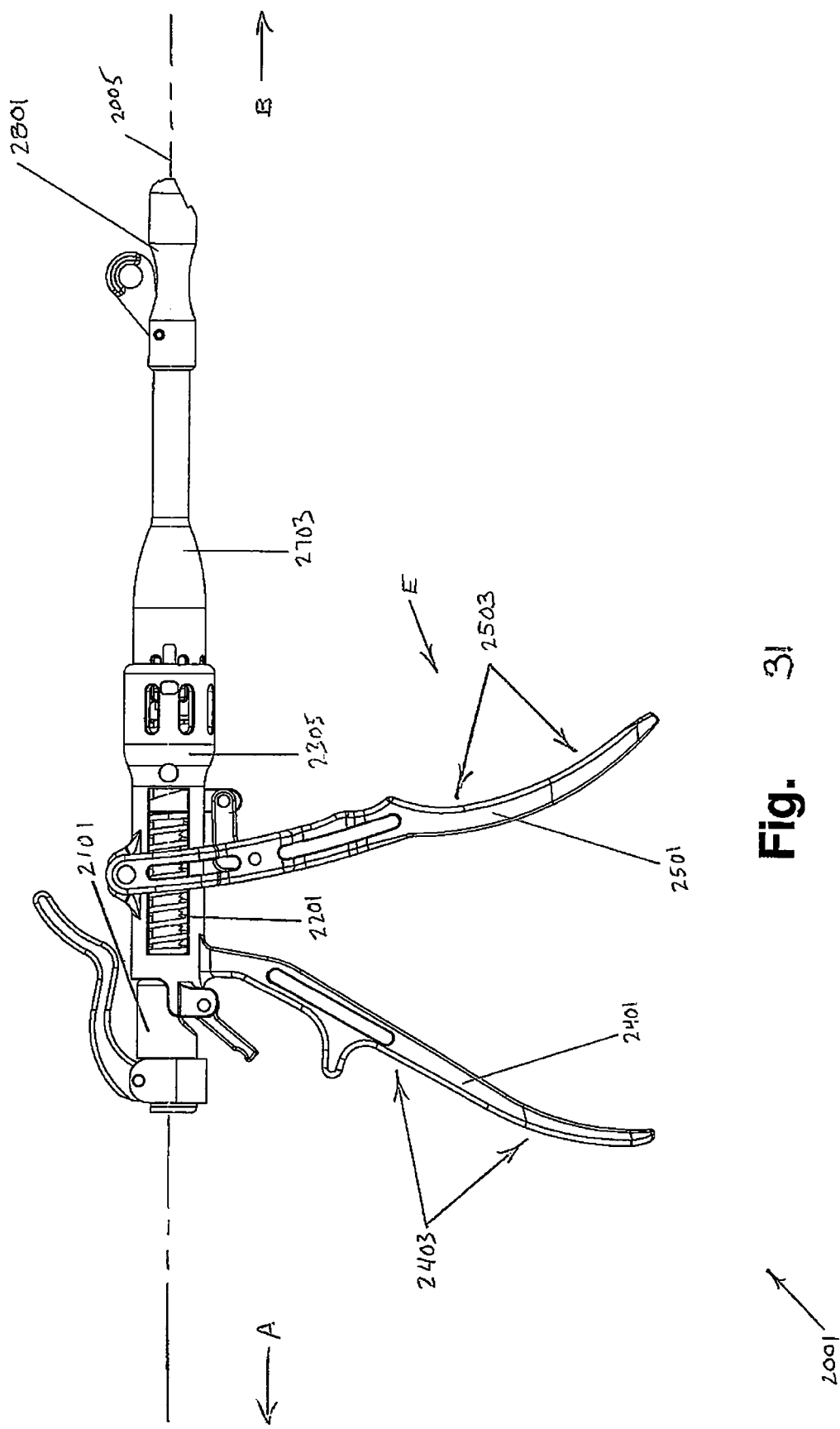
FIG. 31 is a front view of the second embodiment of the pistol grip tensioning apparatus in the secured or locked configuration.

FIG. 29 through 31 helps show the reason for the enhanced mechanical reliability. The centrally located cable race 2005 shows the external path of the surgical cable 12 by the dashed phantom line. The cable race 2005 runs into the distal clamp passage 2805 of the distal clamp assembly 2801, through the indicator passage 2711 of the indicator structure 2703, and then out the proximal clamp passage 2112 of the central portion of the housing structure 2305. The tensioning of the cable 12 along the central longitudinal axis of the tool in the central portion of the cable tensioning apparatus 2001 coincident with the cable race 2005 reduces any bending moment that exists in the offset race 1003, 3003, 4003 of the other embodiments 1001, 3001, 4001.

Figure 9:
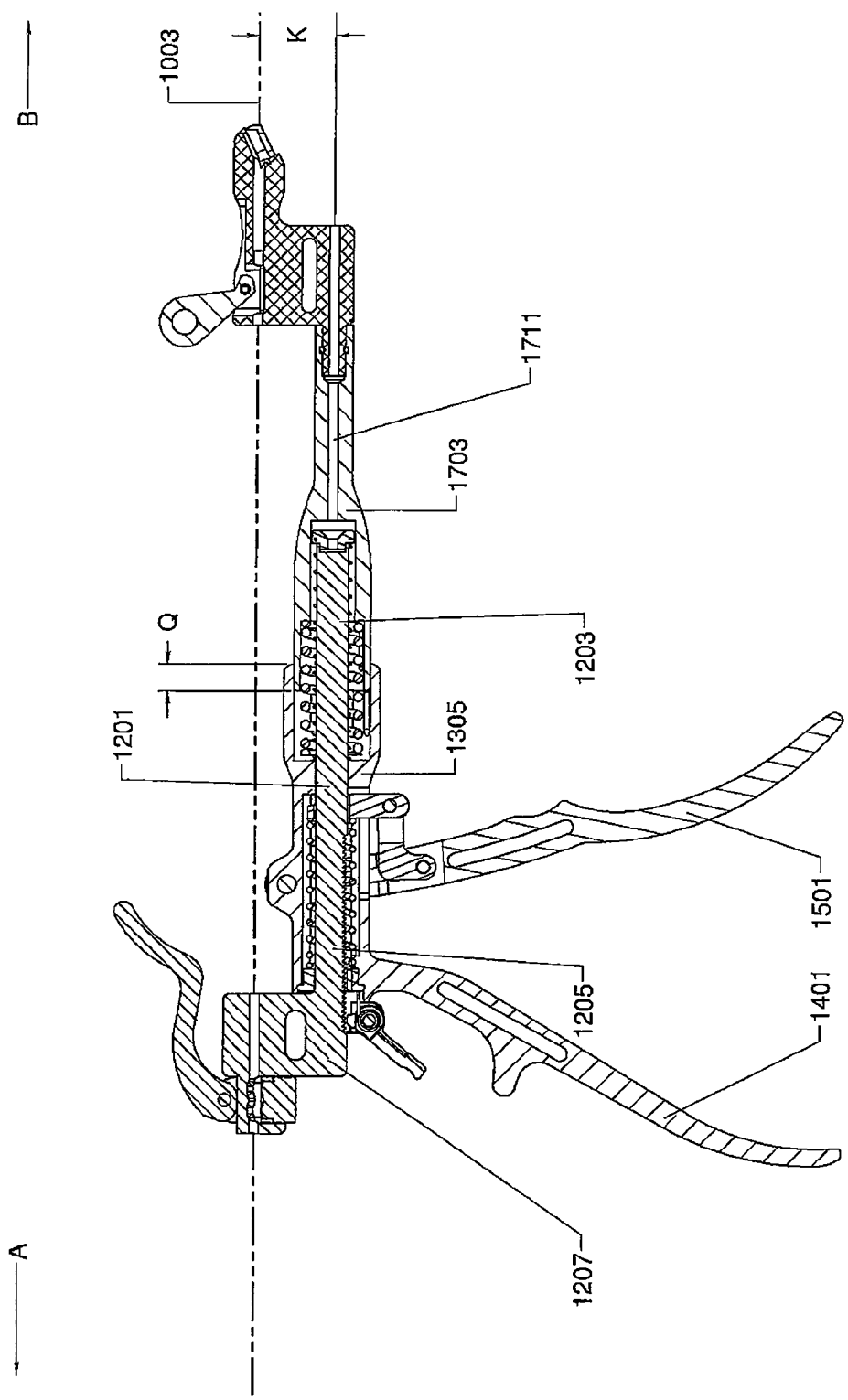
FIG. 9 is a front sectional view of the first embodiment of the pistol grip tensioning apparatus in the initial condition.
Figure 32:
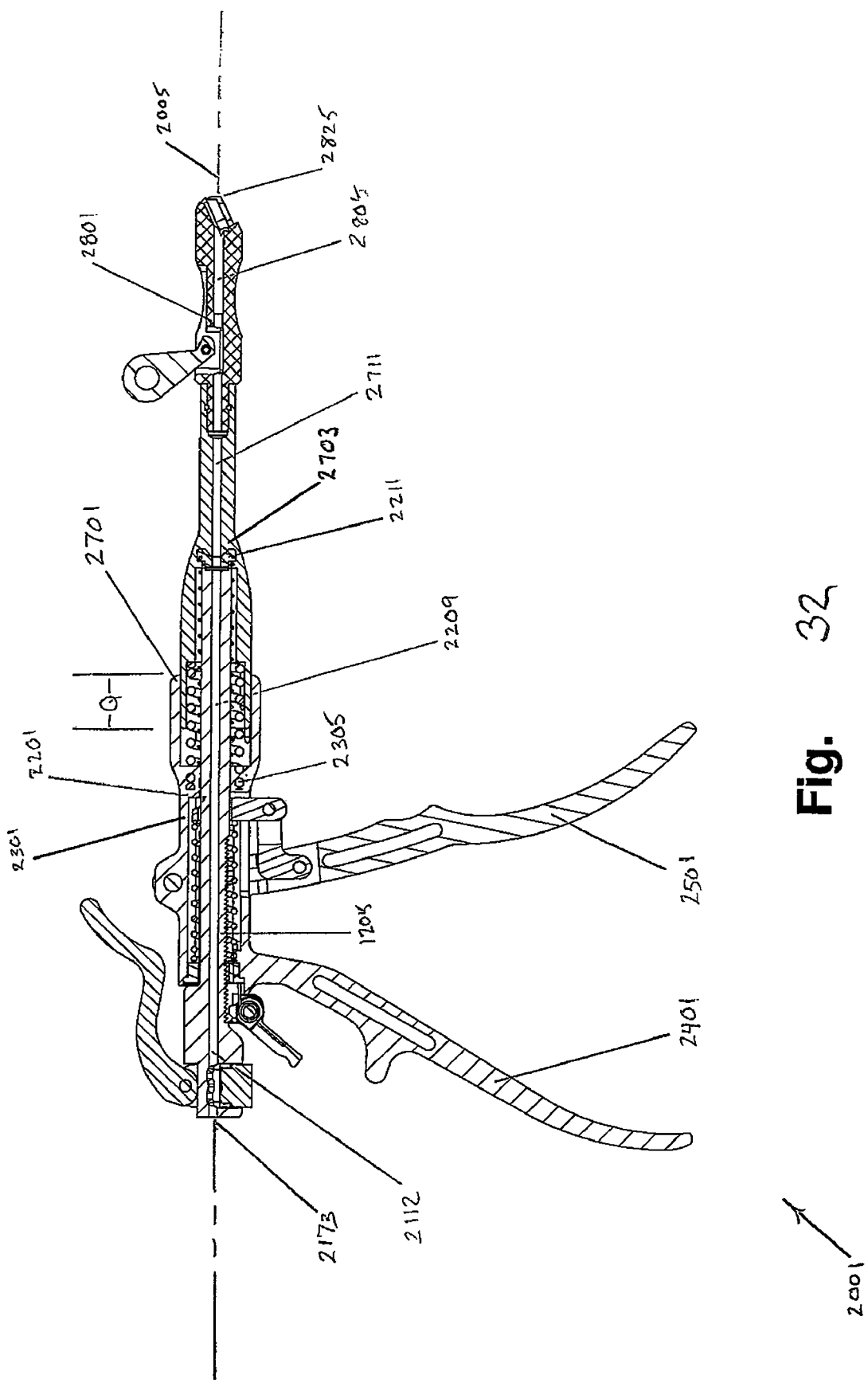
FIG. 32 is a front sectional view of the second embodiment of the pistol grip tensioning apparatus in the initial condition.
Figure 33:
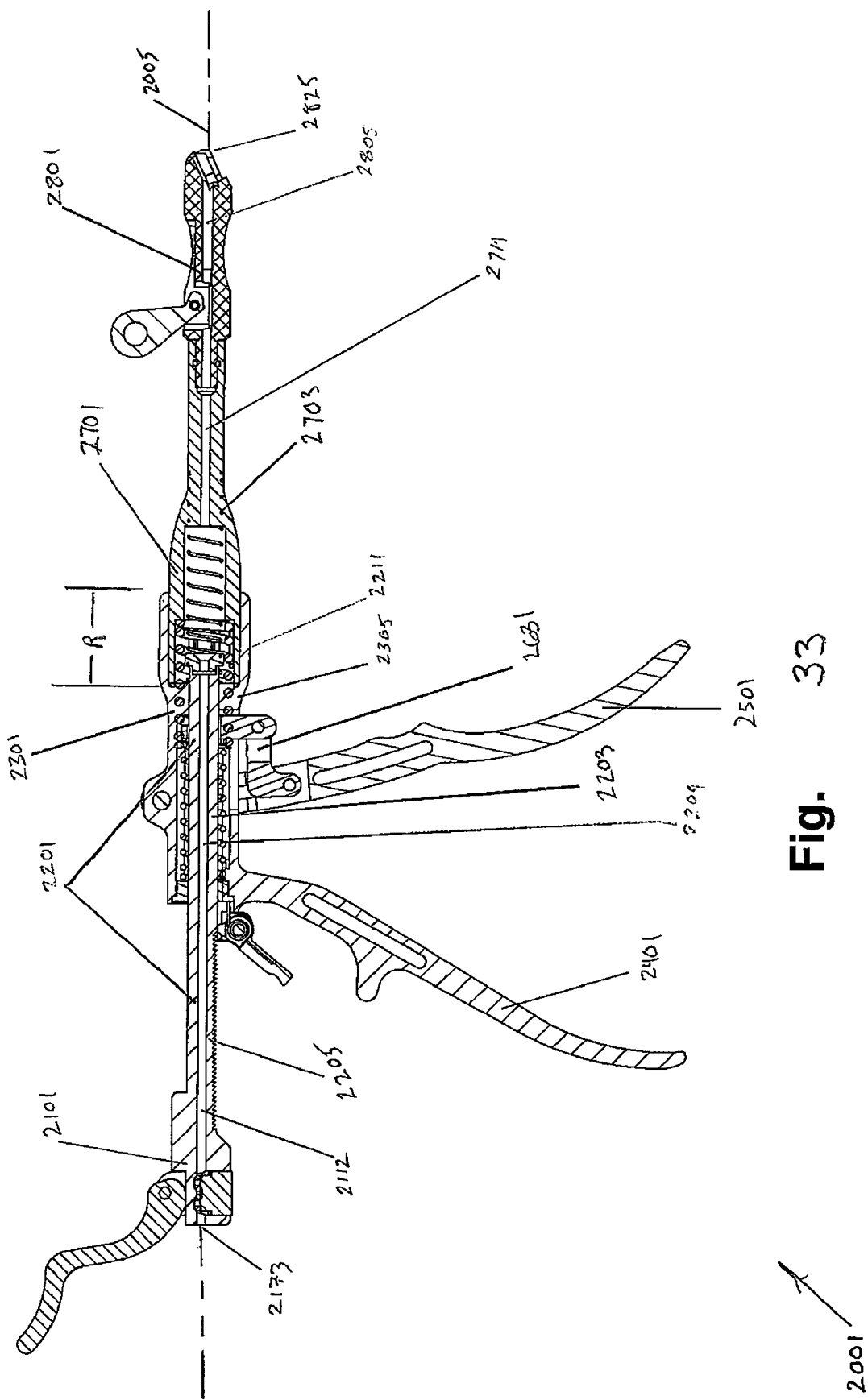
FIG. 33 is a front sectional view of the second embodiment of the pistol grip tensioning apparatus in the fully extended condition.
Figure 34:
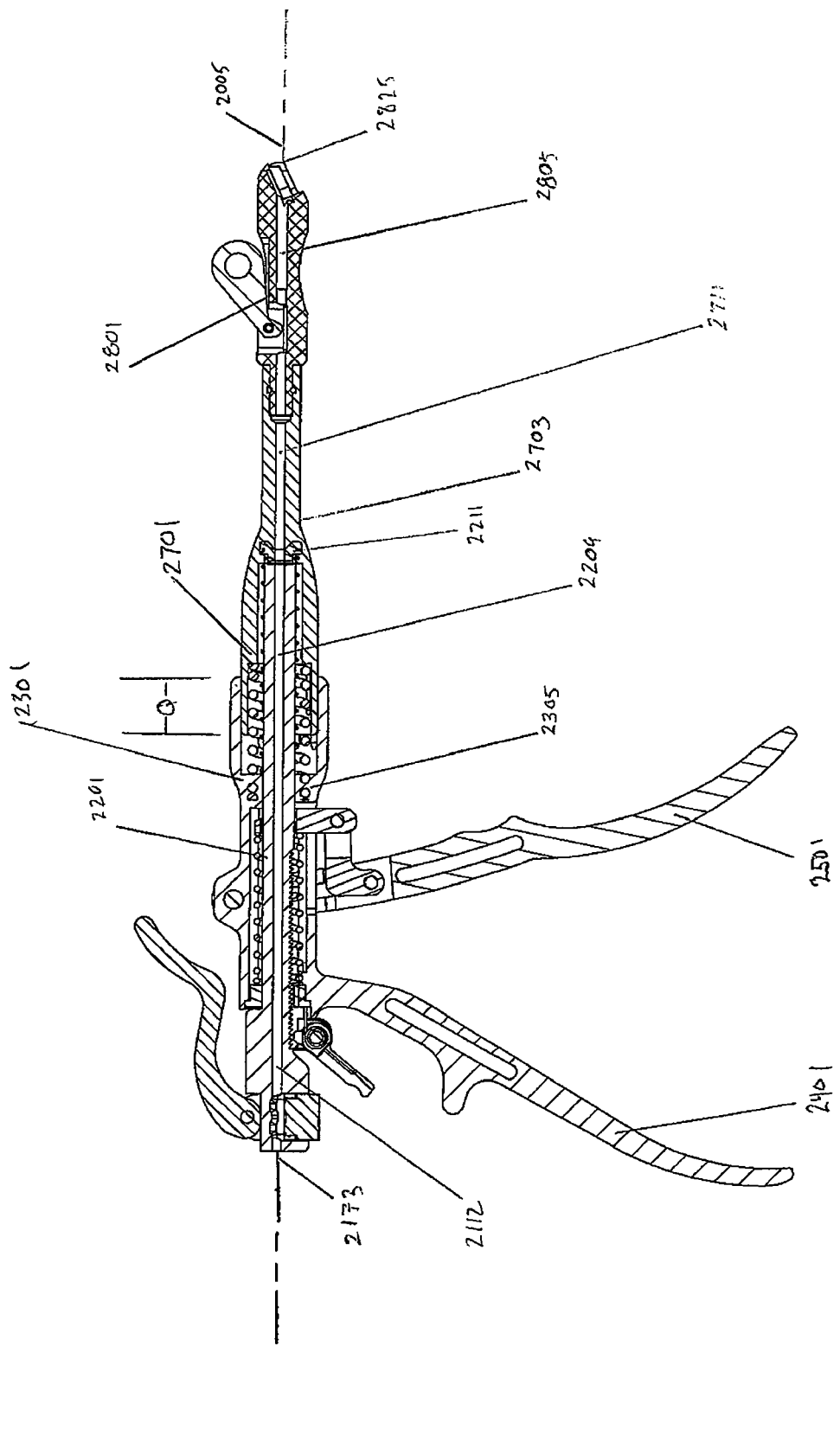
FIG. 34 is a front sectional view of the second embodiment of the pistol grip tensioning apparatus in the secured or locked configuration.

The bending moment can best be seen by comparing the bending moment created by offset distance K in FIG. 9 with the lack of an offset distance shown in FIG. 32. As shown in FIG. 33, when the cable tensioning apparatus 2001 has locked the cable 12 (not shown) in the proximal clamp assembly 2101 and applied tension to the cable 12, the cable 12 is then under a tensile load with corresponding tensile stress in the cable 12. The drive rod 2201, indicator structure 2703, and distal clamp assembly 2801 are then only under a substantially equal compressive load and stress. The substantial elimination of the offset distance K shown in FIG. 10 substantially eliminates the additional bending stress present in the drive rod 1201, the indicator structure 1703, and distal clamp assembly 1801 present in the other embodiments 1001, 3001, and 4001 during tensile loading.

The substantial elimination of a bending moment also substantially eliminates additional friction forces primarily between the housing 2301 and indicator structure 2703 that may interfere with the mechanical operative reliability of the apparatus 1001, 3001, and 4001. The substantial elimination of a bending stress eliminates additional elastic deformation of the apparatus 2001 which can cause undesired mechanical interference when parts are shifted out of position from one another due to the bending stress. Because the bending stress is eliminated when the clamp assemblies are mounted centrally, the apparatus 2001 has the ability to absorb more stress and thus the ability to apply a greater force to the surgical cable 12. The ability to apply greater force by the apparatus 2001 translates into the ability to apply greater tension to the surgical cable 12. The need for applying high cable tension would occur, for example, during arthrodesis where two plates are connected together with wire or cables.

The central cable race 2005 still allows some "pre-tensioning" of the surgical cable 12 because slack in the cable 12 can be removed manually from the race 2005 out of the unlocked proximal clamp assembly 2101 shown as the phantom line in FIG. 29. As shown in FIG. 30, much of the surgical cable 12 is not visible during the tensioning process. However, the condition of the proximal and distal clamp assemblies 2101 and 2801 can readily be determined visually or tactilely because of the positive locking nature of the clamp cam surfaces and cam 2164 and 2807 which cause the clamp assemblies 2101 and 2801 to rest in either the locked or unlocked configuration. For example, the secure or locked configuration of the distal clamp assembly 2801 is readily visible in FIG. 31.

The internal structural components of the central cable race 2005 and internal passages allow for the passing of a cable 12 into and out of the cable tensioning apparatus 2001. The cable 12 enters the cable entrance 2825 at the distal end and passes through the distal clamp passage 2805 as shown in FIG. 32. (The exact details of the distal clamp assembly 2801 are described in more detail subsequently.) The surgical cable 12 then enters the indicator passage 2711 which abuts and is in line with the clamp passage 2805.

Figure 39:
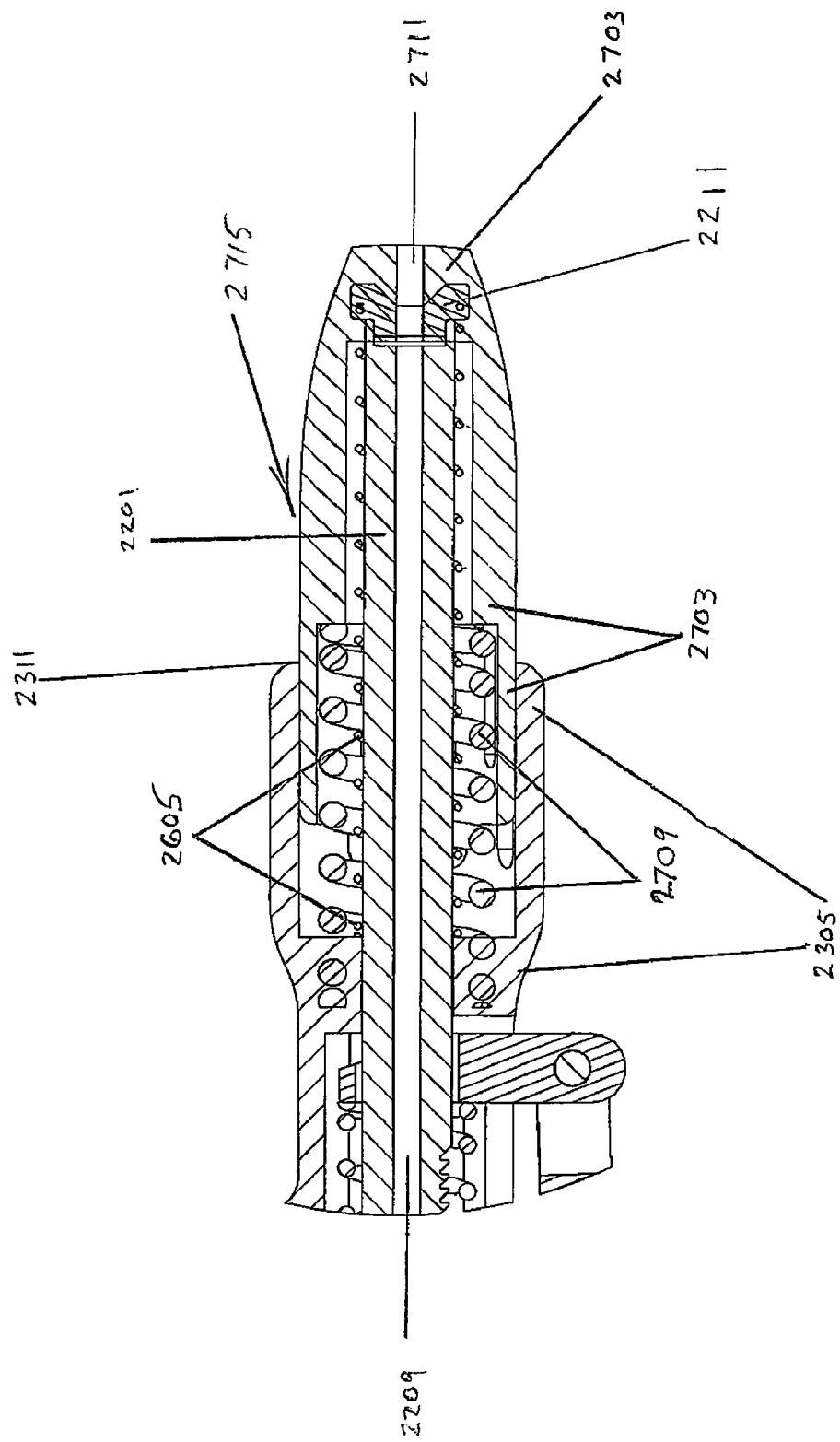
FIG. 39 is a detailed front sectional view of the tension indicator mechanism of the second embodiment of the pistol grip tensioning apparatus in the initial condition.

When the cable 12 is manually passed through the cable tensioning apparatus 2001 in the initial condition, the drive rod passage 2209 of the distal portion 2211 of the drive rod 2201 abuts and is in line with the indicator passage 2711 as shown in FIG. 39. As shown in FIG. 32, the distal portion 2211 of the drive rod 2201 has a concave, funnel shape to direct the surgical cable 12 into the throughbore of the drive rod 2201. Alternatively, the drive rod 2201 could have arcuate, parabolic, or other shapes to direct the surgical cable 12 into the drive rod 2201.

Figure 40:
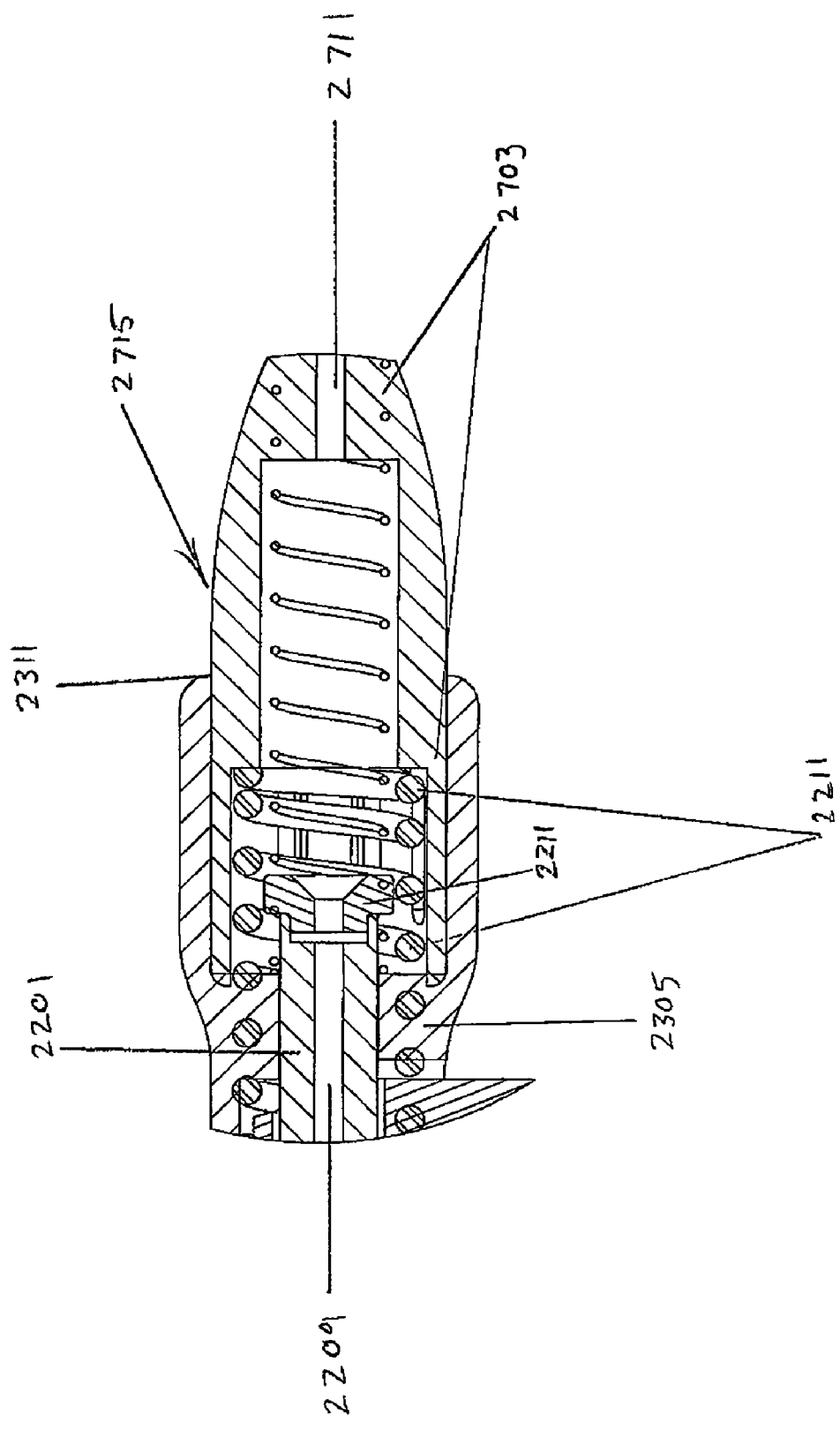
FIG. 40 is a detailed front sectional view of the tension indicator mechanism of the second embodiment of the pistol grip tensioning apparatus in the fully extended condition.

As shown in FIG. 39, the drive rod reset spring 2605 is held in place by the distal tip portion 2211 which is laser welded on to the drive rod 2201. The rod reset spring 2605 has its smaller diameter coils arranged in a nested arrangement with the larger diameter coils of the calibrated compression spring 2709. Normally, the surgical cable 12 will not be fed into the distal portion 2211 of the drive rod 2201 when the cable tensioning apparatus 2001 is in the extended condition as shown in FIG. 40 thus making the possibility of a malfunction while feeding of surgical cable 12 remote. However, the funnel shape of the distal portion 2211 mitigates this possibility of malfunction while feeding surgical cable 12.

The cable 12 will pass through the drive rod passage 2209 and continue to be fed through the proximal clamp passage 2112 as shown in FIG. 32. The surgical cable 12 can be locked into position shown in FIG. 33 (described in detail subsequently) after exiting the cable exit 2173 as in FIG. 32. Note that the internal structural components of the first, second, and fourth apparatuses 1001, 2001 and 4001 are substantially the same so that components of the first apparatus 1001 can be used interchangeably with the components of the second apparatus 2001. Therefore, the housing member 2301, handle 2401, lever 2501, and indicator 2701 of the second apparatus 2001 are the same as the first apparatus 1001 for interoperability.

Proximal Cable Clamp Assembly

The proximal cable clamp assembly 1101 does not damage surgical cable 12 by compression or shear forces on the surgical cable 12 due to the design herein. Any damage to the cable 12 could cause the potential of failure of the cable 12 and injury to the patient. The proximal cable clamp assembly 1101 avoids damage to the cable 12 by applying normal forces distributed over a large surface and thereby reducing the amount of force applied to any one local section of the surgical cable 12.

Figure 13:
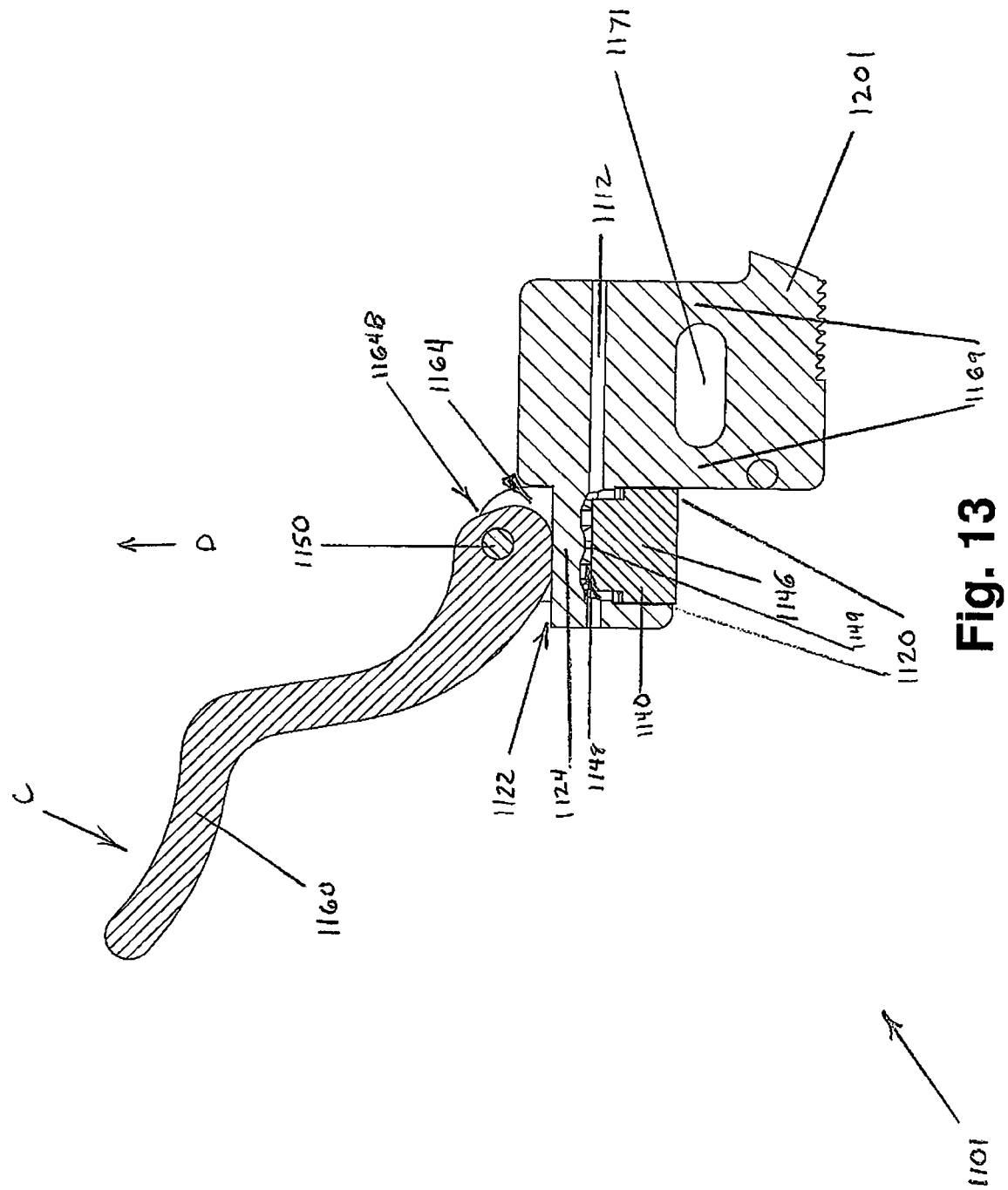
FIG. 13 is a detailed front sectional view of the proximal cable clamp assembly of the first embodiment of the pistol grip tensioning apparatus in the fully extended condition.

The proximal cable clamp assembly 1101 is shown in an unlocked configuration in FIG. 12 and in a secured or locked configuration in FIG. 13. As shown in FIG. 12 and FIG. 13, the proximal cable clamp assembly 1101 is comprised of a generally cylindrical housing, and a generally U-shaped saddle 1140 movably mounted thereon. The saddle 1140 is disposed within a saddle guide 1120 formed in the housing. A cam lever 1160 pivotably cooperates with saddle 1140 by way of a pivot pin 1150 retained within holes formed in the legs of the saddle 1140. Cam lever 1160 includes a cam surface 1164 which engages a cam support surface 1122 provided on the housing. As cam lever 1160 is pivoted with respect to saddle 1140 in a clamping direction C, indicated by arrow C, saddle 1140 is moved in a saddle locking direction D to apply a clamping force to the cable (not shown) as will be described below.

The saddle 1140 is provided with a generally rectangular-shaped saddle jaw 1146 that defines an undulating saddle jaw surface 1148. As illustrated and in order to simplify manufacture, the saddle jaw engaging surface 1167 is formed from a series of curved recesses 1149 separated by flat portions. The invention contemplates other jaw surface shapes, however, including serpentine jaw surfaces.

The saddle jaw 1146 extends into the bore or passage 1112 of the housing for engaging a periphery of the cable (not shown). The saddle jaw 1146 cooperates with a complementarily-shaped housing jaw housing 1124 in order to form a generally undulating clamping space. The undulating surface of jaw housing 1124 shown in FIG. 12 and FIG. 13 may be formed as a series of annular ribs within the passage 1112.

As will be appreciated by those of ordinary skill, the movement of the cam lever 1160 from a released position in the direction C to a clamping position shown in FIG. 13 causes the cam surface 1164 to move with respect to the cam support surface 1122, thereby moving saddle 1140 within saddle guide 1120 in direction D which is substantially transverse to the longitudinal extent of bore or passage 1112 and into a clamping position. The surface of the jaw housing 1124 and the saddle jaw surface 1148 cooperate to redirect the cable 12 from a substantially straight path to an undulating path when the saddle 1140 is moved to a clamping position. It will be appreciated that the undulating surfaces of the saddle jaw 1146 and jaw housing 1124 increase the area of the cable to which the clamping force is applied. Thus, the amount of force that may be safely applied to a cable without risk of damage is increased compared to prior art clamping devices.

The cam lever 1160 is provided with a multifaceted cam surface. The cam surface 1164 includes two facets: facet 1164A and facet 1164B, which each define a clamping position for clamping cables. Each facet 1164A and 1164B of the cam lever 1160 is preferably provided as a substantially flat surface for engaging the cam support surface 1122 on the housing 1124. Each facet has associated with it a radial dimension measured from the cam lever pivot axis. The radial dimensions are selected to provide optimum clamping force for cable 12 used with the cable clamp assembly.

Preferably, cam surfaces 1164A and 1164B are provided with respective flat portions that extend on both sides of respective radial lines to facilitate the positive locking aspects of the invention. That is, cam surface 1164 includes a first flat portion of the cam surface 1164A that engages the cam support surface 1122 and positively locks the proximal clamp assembly 1101. Cam surface 1164 also includes a second, flat portion of the cam surface 1164B that engages the cam support surface 1122 and positively unlocks the clamp assembly 1101. Cam surface 1164A and 1164B provide for stable locking positions of the cam lever 1160 and positive tactile indication that the desired locking position has been reached.

As will be recognized by those of ordinary skill, the clamp assembly 1101 applies a clamping force to the cable 12 without direct contact between the cam lever 1160 and the cable 12, thereby minimizing damage from abrasion and shear forces. Clamping force is applied through the saddle, which applies a lateral force against the cable surface and redirects the cable 12 into an undulating or non-linear path defined between the housing jaw and saddle jaw. Thus, the potential for damage to the cable surface is reduced compared to prior art cable clamps. Moreover, less clamping force occurs with cable tension, since the cable attempts to straighten and consequently applies normal forces to the obstructing internal surfaces of the clamp. These cable tension induced normal forces reduce the normal forces generated by the clamp body through action of the lever. It will also be recognized that clamping devices herein may be used to clamp different sized cables, without refitting parts or clamping jaws with new dimensions. Moreover, the clamping devices herein provide for positive tactile determination as to when the cam lever 1160 has been moved to one of a plurality of clamping positions.

As shown in FIGS. 12 and 13, the cam surface 1164 of lever 1160 cooperates with the cam support surface 1122. As lever 1160 is pivoted about pivot pin 1150, the saddle 1140 moves relative to the jaw housing 1124 in a direction D.

The engaging surface 1167 is formed from the housing member 1301 to engage the cable 12. The engaging surface 1167 is formed in any variety of shapes so as to engage a portion of the periphery of the elongate member. In particular, The engaging surface 1167 can be non-linear along at least a portion of its lengthwise cross-section, and/or concave along at least a portion of its widthwise cross-section. In these two exemplary forms, the engaging surface 1167 respectively serves to redirect the cable 12 into a non-linear path and to cup a length of the cable 12 at the point of clamping. The engaging surface 1167 also serves to increase the normal force for clamping the cable 12, without damaging the cable 12. The proximal cable clamp assembly 1101 is described in further detail in U.S. Pat. No. 7,452,360, filed Nov. 14, 2001 titled "Method and Apparatus for Clamping Surgical Wires or Cables" which is incorporated by reference in its entirety herein.

Figure 35:
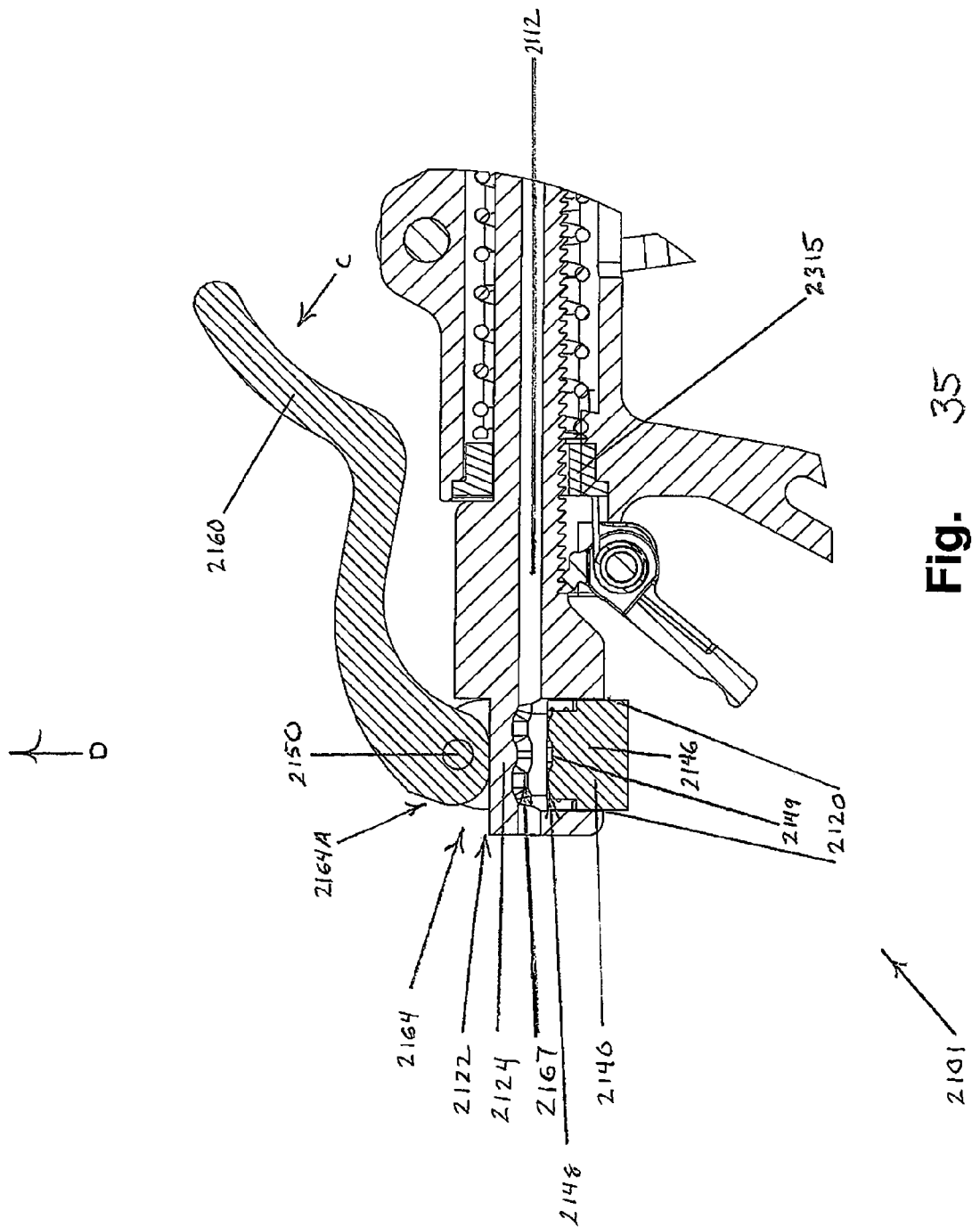
FIG. 35 is a detailed front sectional view of the proximal cable clamp assembly of the second embodiment of the pistol grip tensioning apparatus in the initial condition.
Figure 36:
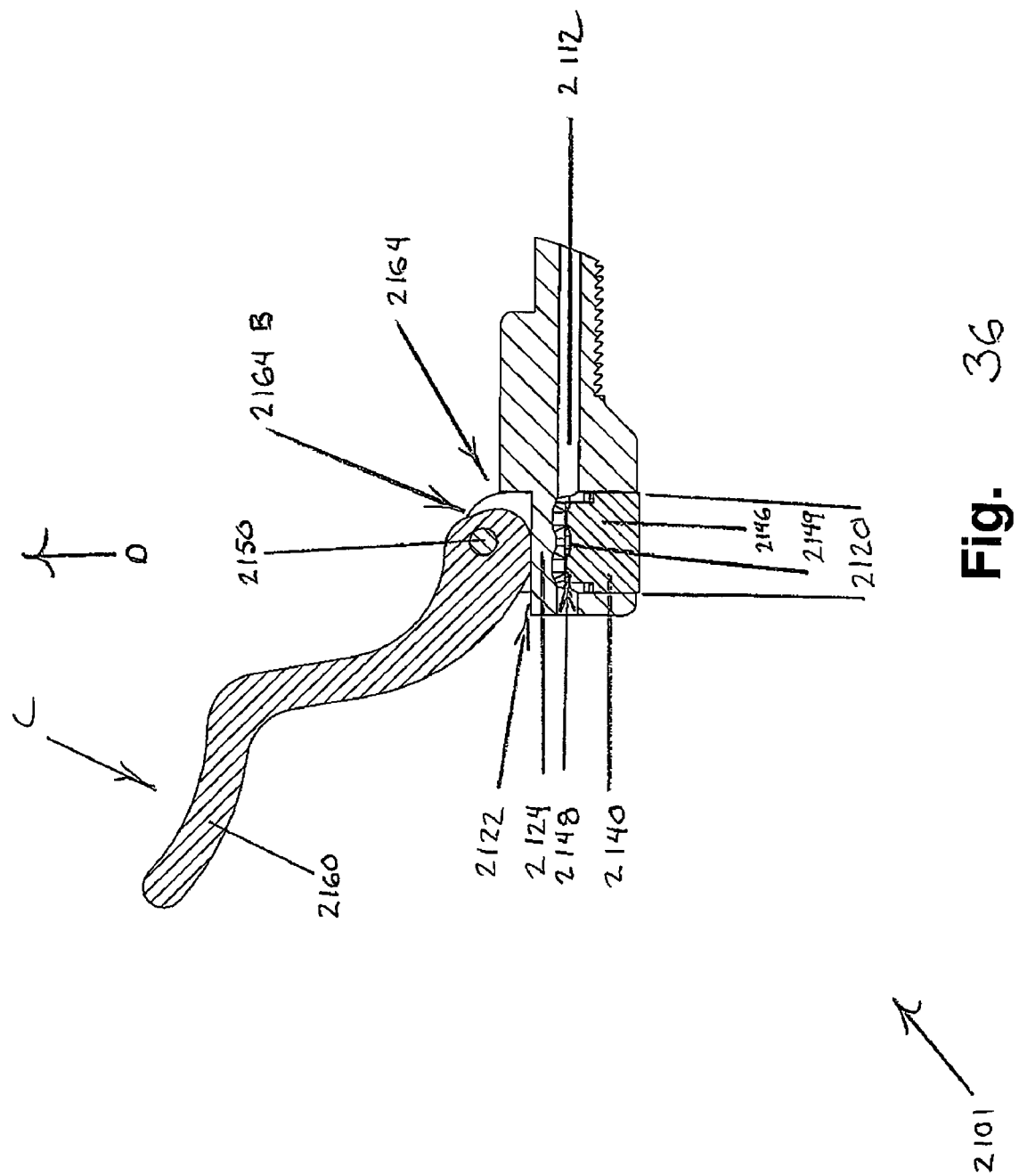
FIG. 36 is a detailed front sectional view of the proximal cable clamp assembly of the second embodiment of the pistol grip tensioning apparatus in the fully extended condition.

The second locking clamp assembly 2101 is shown in FIG. 35 and FIG. 36 and is similar to locking clamp assembly 1101 described previously. The passage 2112 in the second embodiment 2001 passes through the entire length of the cable tensioning apparatus 2001 unlike the foreshortened passage 1112 in the first embodiment 1001. The proximal locking clamp assembly 2101 is in line and contiguous with the drive rod 2201.

In contrast, the first, third and fourth apparatuses 1001, 3001, 4001 include bridging material 1169, 3169, 4169 to connect the proximal clamp assembly 1101 to the drive rod 1201 in a radially offset arrangement as shown in FIG. 12, 13, 56, 57, 78, 79. The proximal locking clamp assembly 1101 of the first apparatus 1001 is identical to the proximal locking clamp assembly 3101 of the third apparatus 3001 and proximal locking clamp assembly 4101 of the fourth apparatus 4001. In addition, the same indirect proximal locking cable clamp assembly is used on all the apparatuses 1001, 2001, 3001, 4001 in the proximal position.

Figure 78:
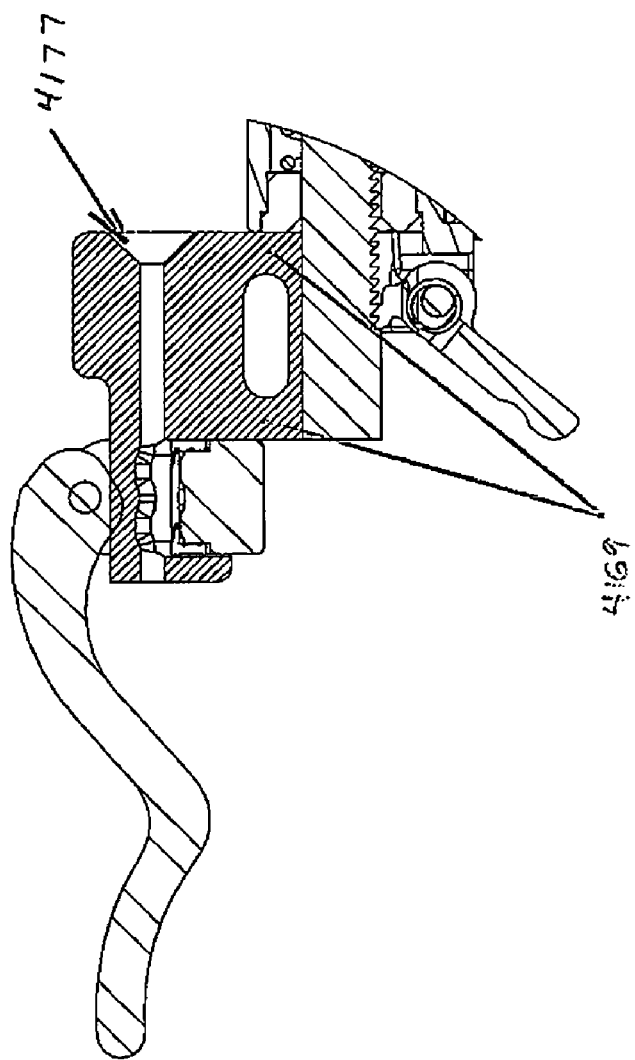
FIG. 78 is a detailed front sectional view of the proximal cable clamp assembly of the fourth embodiment of the pistol grip tensioning apparatus in the initial condition.

The fourth apparatus 4001 utilizes the indirect proximal locking cable clamp assembly, i.e. the U-shaped saddle, also for the distal cable clamp assembly 4801. Finally, the fourth apparatus 4001 also illustrates the use of a funneled surface 4177 at the proximal cable entrance 4175 to assist the feeding of surgical cable 12 into the proximal cable clamp assembly 4101 as shown in FIG. 78. The funneled surface 4177 could have arcuate, parabolic, or other shapes to provide the function of improved insertion of surgical cable. Alternatively, the funneled surface 4177 could be used for the proximal cable clamp assemblies for the other pistol grip tensioning apparatuses 1001, 2001, 3001.

Distal Cable Clamp Assembly

The distal cable clamp assembly 1801, 2801, 3801 locks surgical cable 12 by compression through cam action of the clamp assembly 1801 directly on the cable 12 for the first three embodiments 1001, 2001, 3001. The distal cable clamp assembly 1801, 2801, 3801 has the ability to lock the cable 12 in the more restricted space around the incision because the reduced length of the distal clamp lever 1803, 2803, 3803. In addition, the distal cable clamp assemblies 1801, 2801, and 3801 are also detachable and interchangeable through the use of a hexagonal bit. Finally, the distal cable clamp assembly 1801, 2801, and 3801 also engages the surgical connector 10 which is described in more detail below.

Figure 19:
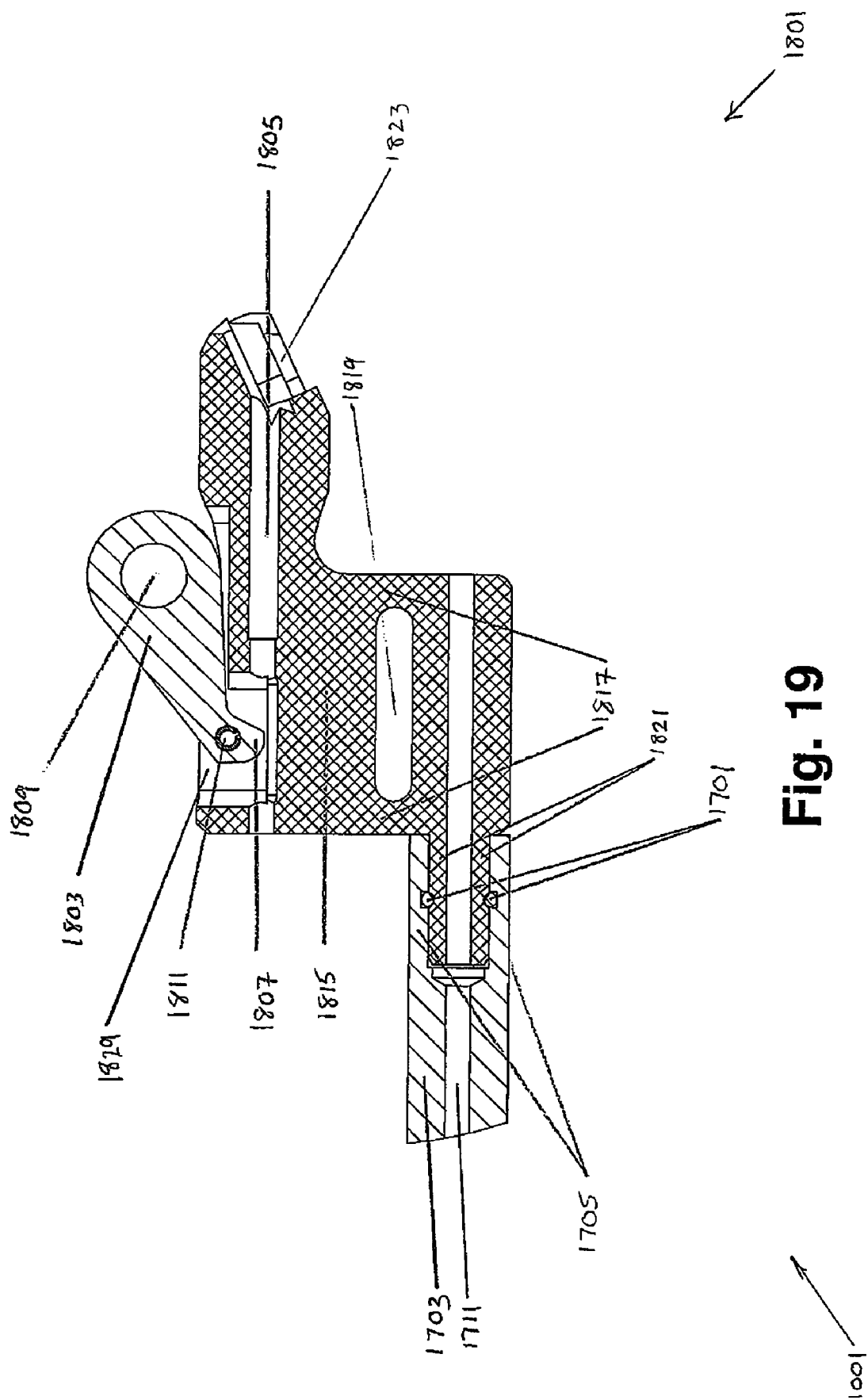
FIG. 19 is a detailed front sectional view of the distal cable clamp assembly of the first embodiment of the pistol grip tensioning apparatus in the secured or locked configuration.
Figure 20:
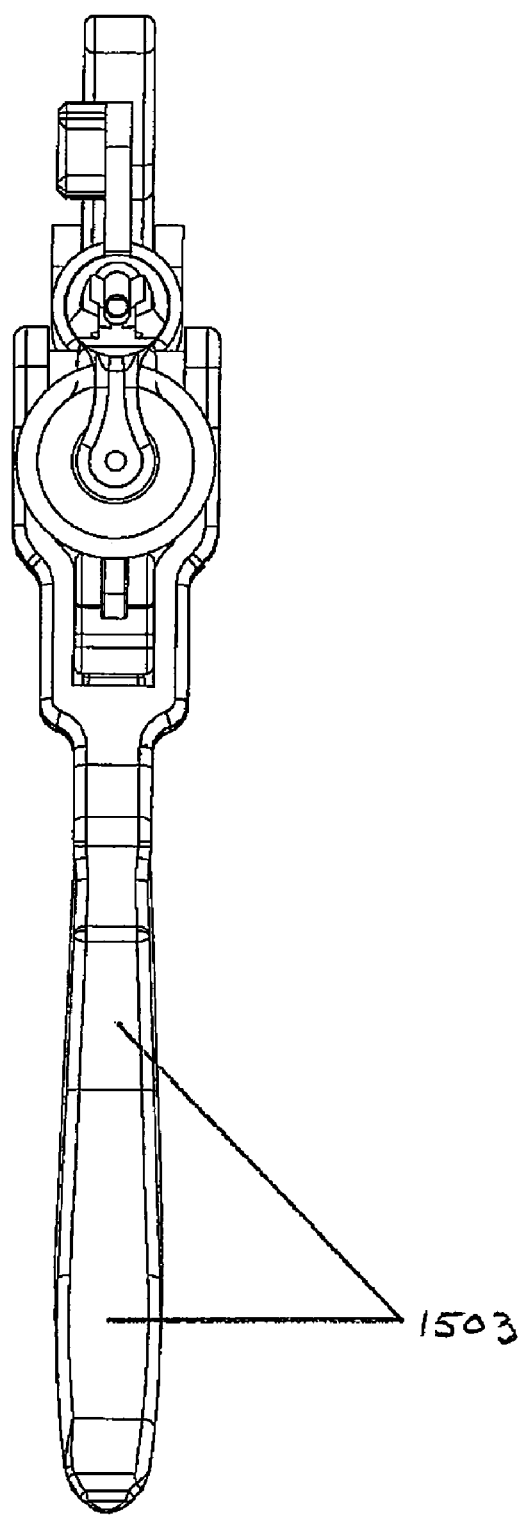
FIG. 20 is a right side view of the first embodiment of the pistol grip tensioning apparatus in the initial condition.

For the first apparatus 1001, the distal cable clamp assembly 1801 is shown in an unsecured or unlocked configuration in FIG. 18 and secured or locked configuration in FIG. 19. As shown in FIG. 18 and FIG. 19, the distal cable clamp assembly 1801 is comprised of a distal clamp lever 1803, a cam pin 1811, and the distal cam 1807 mounted on the clamp body 1815.

As shown in FIG. 18, the distal cable clamp assembly 1801 is shown in the unsecured or unlocked configuration. The rotatable distal cable clamp assembly 1801 consists of a rotatable cam 1807 connected to a distal clamp lever 1803 which is carried on the clamp body 1815 by a cam pin 1811. The cam 1807 is capable of rotating and rotating back into the unlocked position as shown in FIG. 18 where the cam 1807 is spaced from the passage 1805 to the locked position shown in FIG. 19. As shown in FIG. 18 in the unsecured or unlocked configuration, the surgical cable 12 can pass unobstructed through the space provided in the passage 1805 during the cable tensioning process.

The distal cable clamp assembly 1801 has a central portion 1813 which is filleted or radiused inwardly as shown in FIGS. 6 and 18, to facilitate the user in gripping the clamp assembly 1801 to easily engage and disengage it with the clamp assembly 1801 with the rest of the cable tensioning apparatus 1001. The distal cable clamp assembly 1801 has bridging material 1817 and an opening 1819 to structurally support the radially offset connection of the clamp assembly 1801 to the rest of the cable tensioning apparatus 1001.

Finally, the entire distal cable clamp assembly 1801 is modular and detachable to adapt the cable tensioning apparatus 1001, 2001, and 3001 to other types of surgical connectors 10. The indicator structure 1703 defines a hexagonal socket 1705 and split ring retention spring 1707 for receiving a tubular extension 1821 of the distal cable clamp assembly 1801, with the retention spring 1707 fitting into an annular groove of the extension 1821 in a conventional manner. The round modular connection of the tubular extension 1821 is self centering to assure proper position of the distal cable clamp assembly 1801. The distal cable clamp assembly 1801 is non-rotatable because its tubular extension 1821 is hexagonal (or alternatively of other non-circular cross section) fitting into a hexagonal socket 1705 at the distal end of the hexagonal socket 1705 (or alternatively other non-circular cross section).

As shown in FIG. 19, the distal cable clamp assembly 1801 is shown in the secured or locked configuration. The cam 1807 is capable of rotating into the locked position as shown in FIG. 19 where the cam 1807 partially blocks the passage 1805 in the secured or locked configuration shown in FIG. 19. As shown in FIG. 19 in the secured or locked configuration, the surgical cable 12 can not pass unobstructed through the space provided in the passage 1805 during the cable tensioning process. The cam 1807 directly engages or contacts the surgical cable 12 to create friction against movement by the friction force applied by the cam 1807 and the clamp body 1815. As shown in FIG. 19 in the secure or locked configuration, the surgical cable 12 can not pass through the passage 1805 as part of the cable tensioning process. The distal cable clamp assembly 1801, 2801, and 3801 is described in further detail in U.S. Utility Pat. No. 5,788,697, filed Mar. 15, 1996 titled "Cable Tensioning Device" which is incorporated by reference in its entirety herein.

Figure 46:
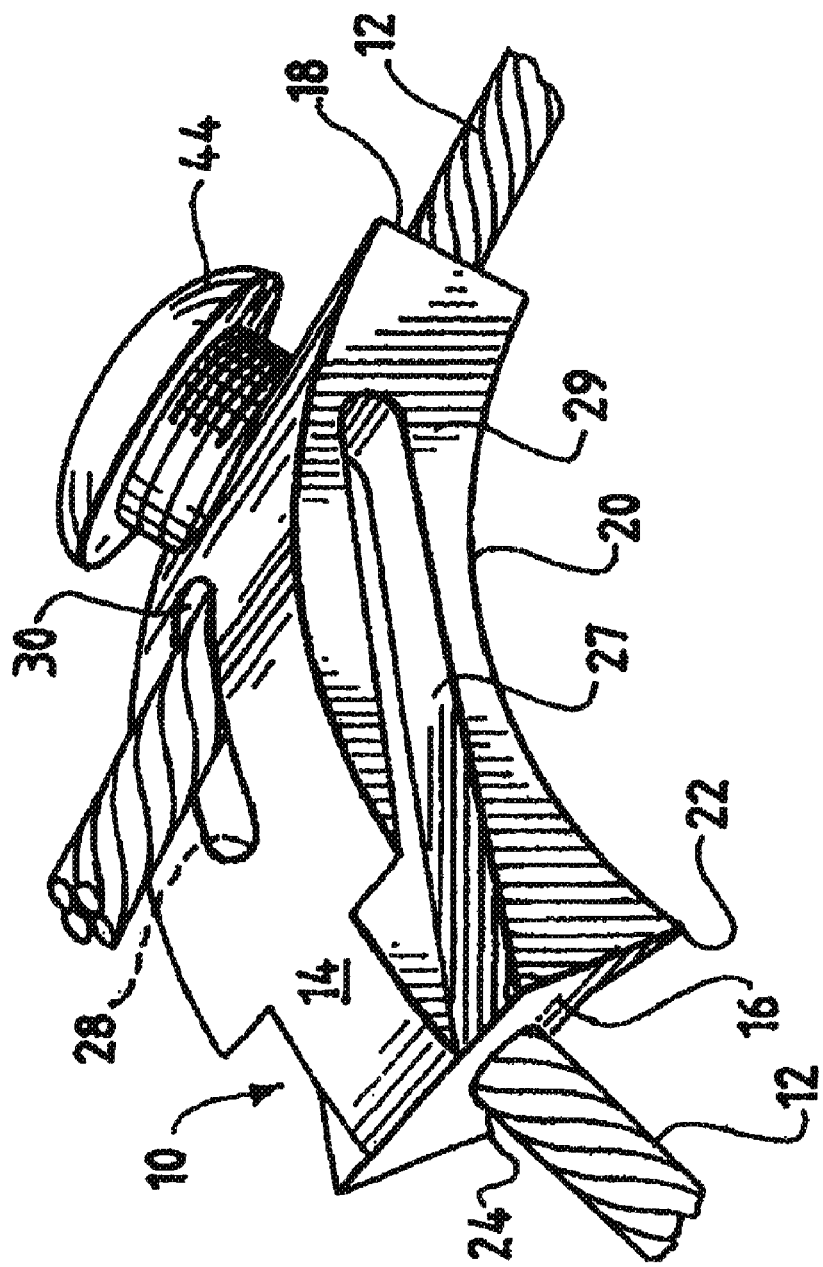
FIG. 46 is a perspective view of the connector for cable ends (which corresponds to FIG. 1 in U.S. Pat. No. 5,415,658).

The distal cable clamp assembly 1801 also engages or interfaces with the unique surgical connector 10 shown in FIG. 46. This unique surgical connector 10 is typically used with the assignees' surgical implant devices (described in more detail in U.S. Pat. No. 7,207,993 B1 which is herein incorporated by reference) for prophylactic banding. The surgical connector 10 is also described in further detail in U.S. Pat. No. 5,415,658, titled "Surgical Cable Loop Connector" filed Dec. 14, 1993 which is incorporated by reference in its entirety herein.

Figure 47:
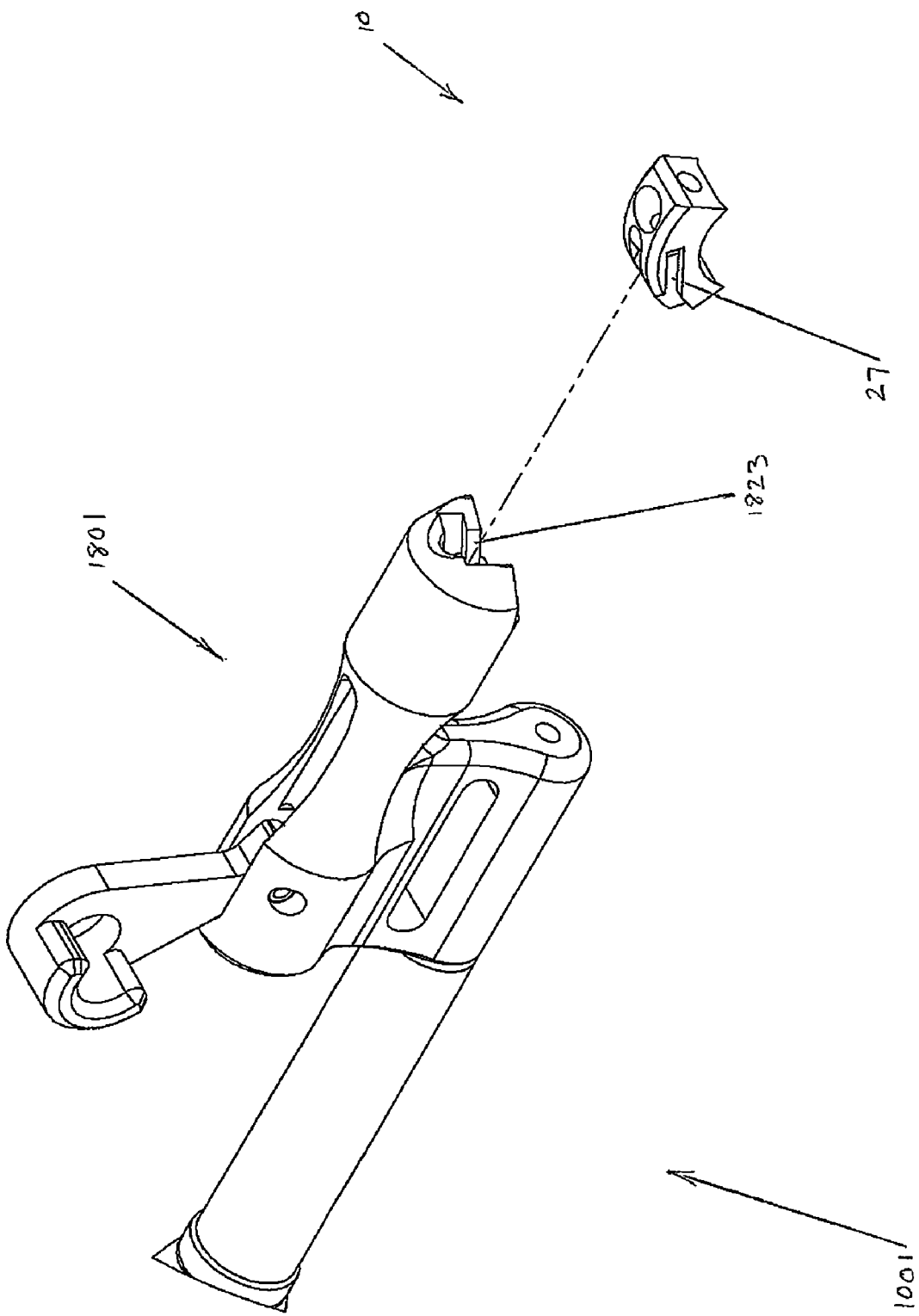
FIG. 47 is an exploded view of the first embodiment of the pistol grip tensioning apparatus in the initial condition and a surgical connector.
Figure 48:
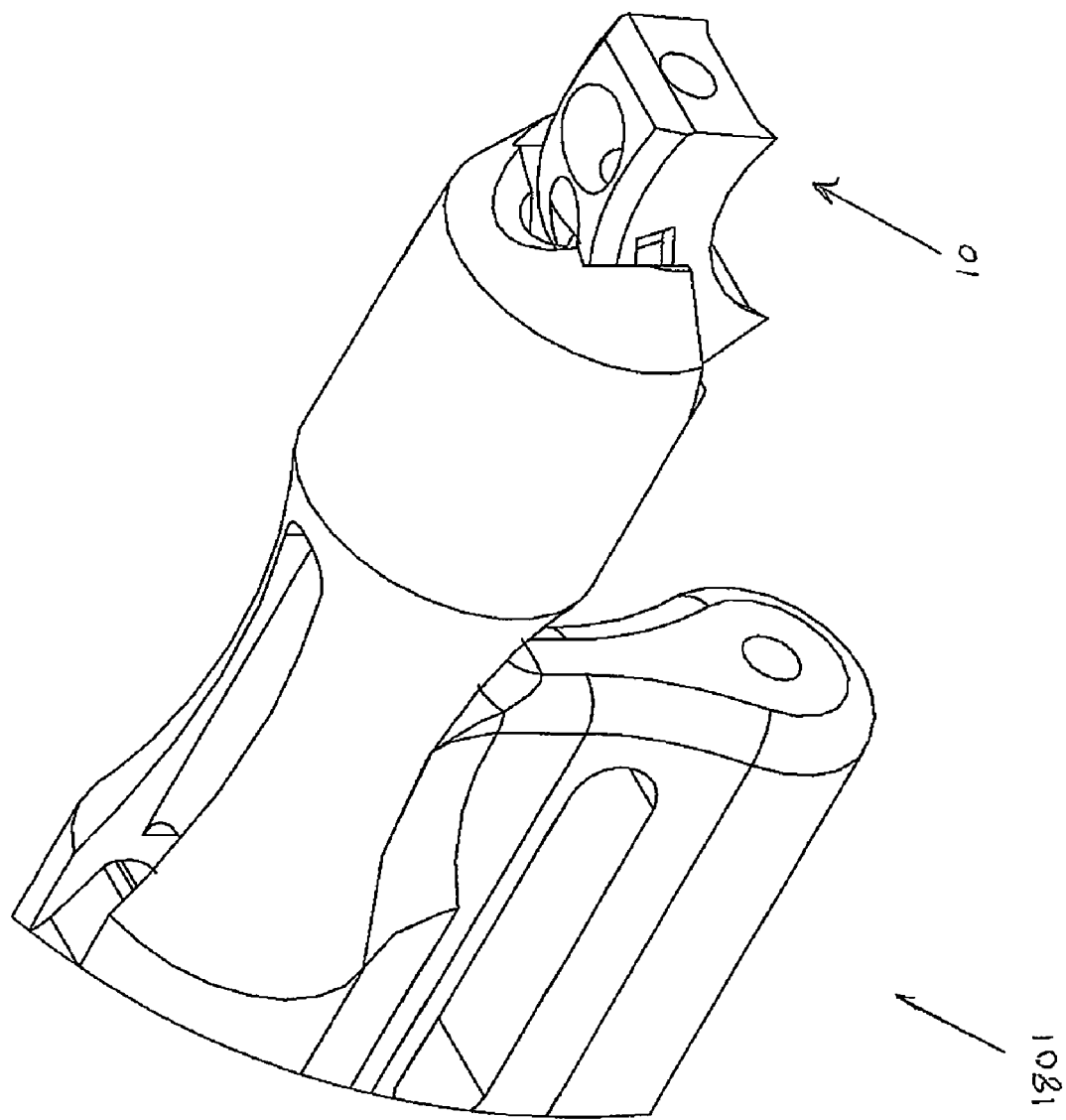
FIG. 48 is a detailed isometric view of the first embodiment of the pistol grip tensioning apparatus mechanically interfacing with a surgical connector.
Figure 49:
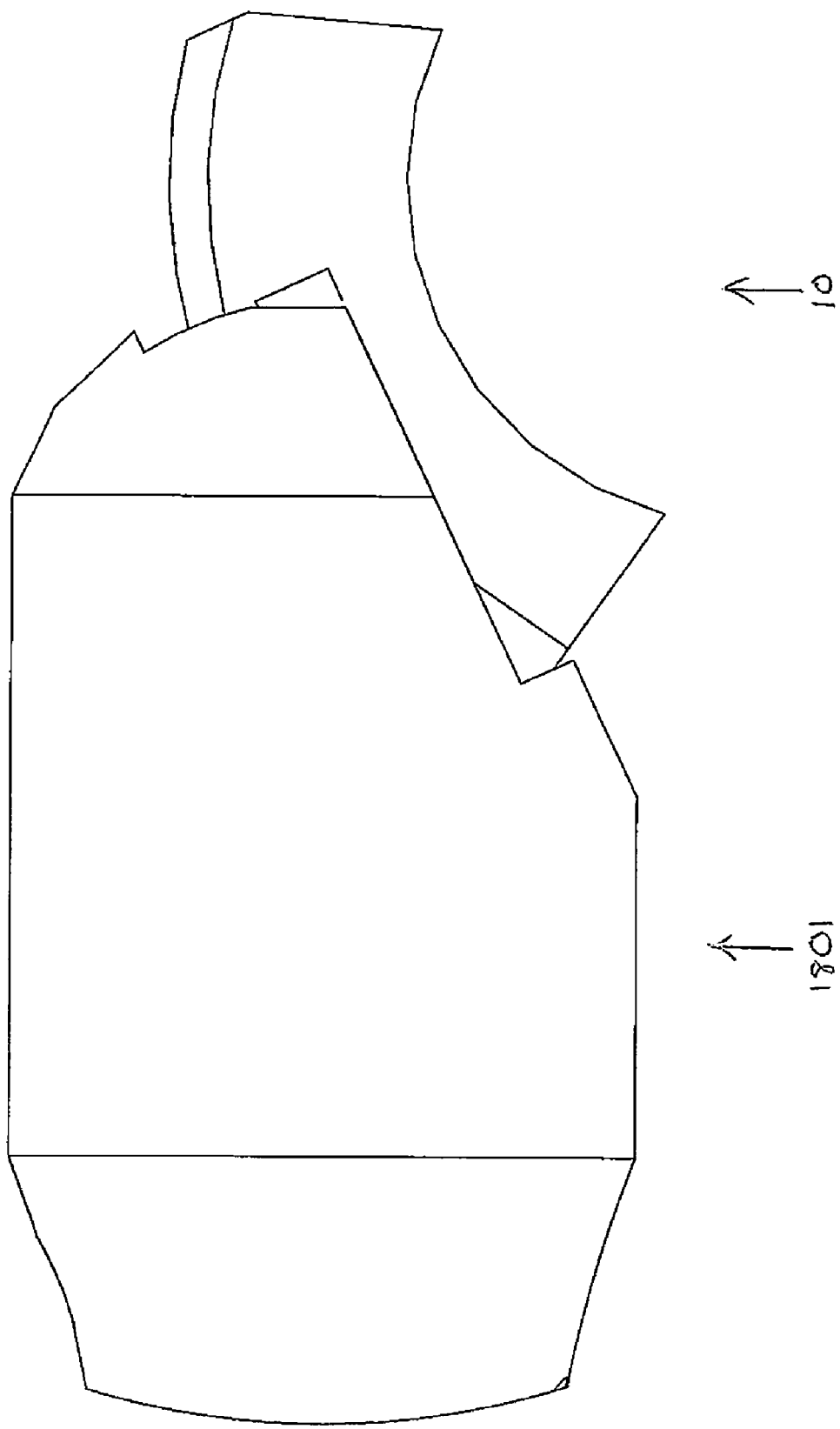
FIG. 49 is a front view of the pistol grip tensioning apparatus mechanically interfacing with a surgical connector.
Figure 50:
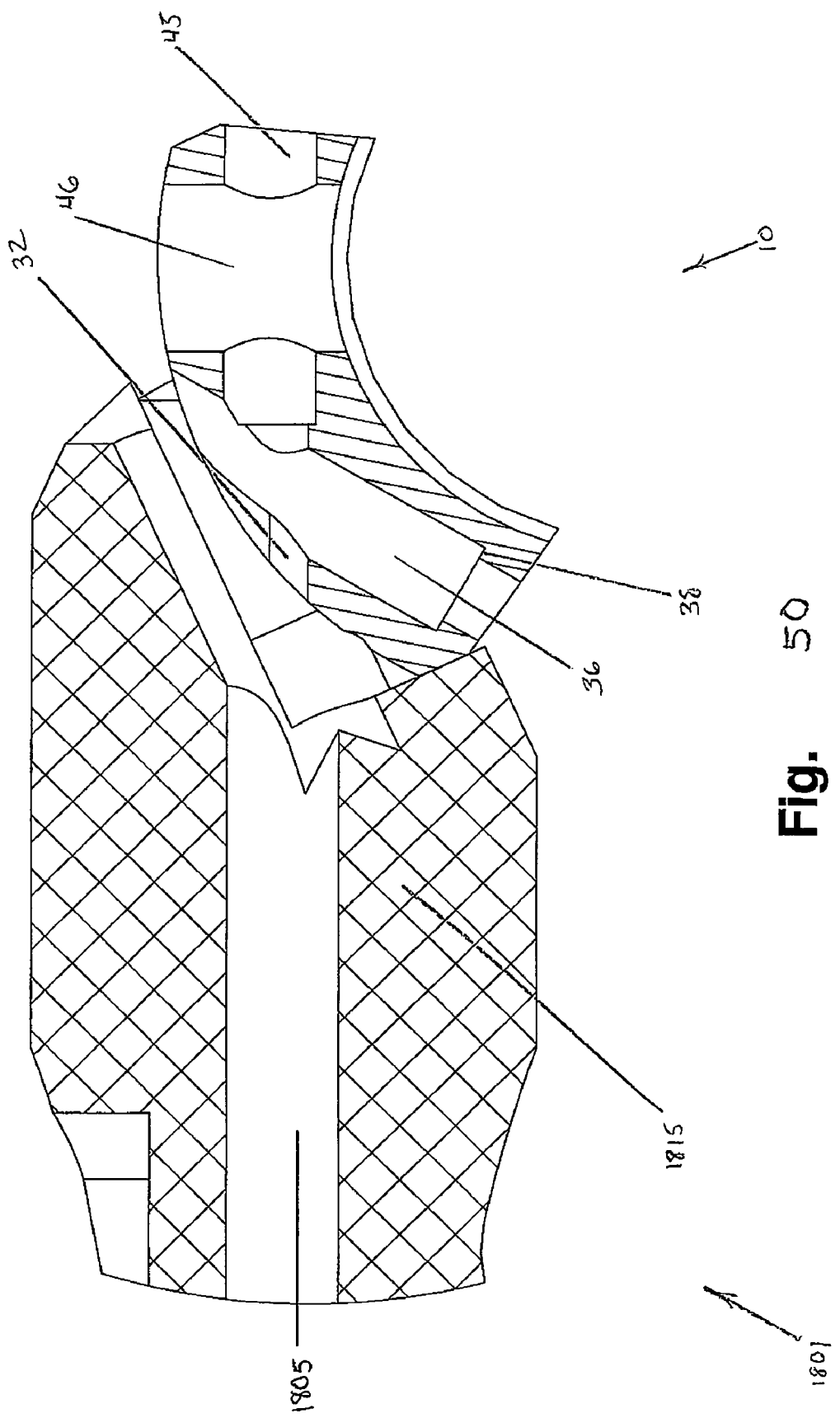
FIG. 50 is a front sectional view of the pistol grip tensioning apparatus mechanically interfacing with a surgical connector.

The distal cable clamp assembly 1801 engages the surgical connector 10 as shown in FIG. 48 and FIG. 49. As shown in FIG. 50, the distal cable clamp assembly 1801 is shown to have a sliding or shiftable fit into a slot 27 of the surgical connector 10, which in turn, is carried by the pistol grip cable tensioning device or apparatus 1001. As shown in FIG. 47, the slot 27 of the surgical connector 10 slides onto the flange 1823 of the distal cable clamp assembly 1801. As shown in FIG. 48, the surgical connector 10 meshes or engages the distal cable clamp assembly 1801 to create mechanical engagement and a partial connection between the surgical connector 10 and the cable tensioning apparatus 1001.

The structure and engagement of the distal cable clamp assembly 1801 for the first embodiment has been described as an exemplar for the other distal cable clamp assemblies 2801, 3801 for the second and third embodiments of the pistol grip tensioning apparatuses 2001, 3001. The structure of the distal cable clamp assembly 1801 with the surgical connector 10 is substantially the same as the distal cable clamp assemblies 2801 and 3801 of the second and third apparatuses 2001 and 3001 and not repeated for brevity. The surgical connector 10 meshes or engages in the same manner with the distal cable clamp assemblies 2801 and 3801 of the second and third embodiments 2001 and 3001. Alternatively, many different conventional designs of surgical connectors or crimps may be configured to be used with the cable tensioning apparatus 1001, 2001, 3001, and 4001 via the hexagonal socket, retention spring, and tubular extension described previously.

For example, the cable 12 passes through the surgical connector 10 during tensioning into the passage 1805 of the distal cable clamp assembly 1801, which is carried on to the proximal clamp assembly 1101. The cable 12 is tensioned and the cable 12 is locked with the distal cable clamp assembly 1801. As shown in FIG. 19, the cable 12 enters into engagement with the distal cam 1807, which retains the cable 12 through rotation of the distal clamp lever 1803 into its horizontal position. The cable 12 is locked in the surgical connector 10 with the screw 44 as shown in FIG. 46. The cable 12 is then cut and the cable tensioning device of this invention is disengaged from the surgical connector 10 by allowing the connector 10 to slide out of slot 27, and the cerclage is complete.

Figure 41:
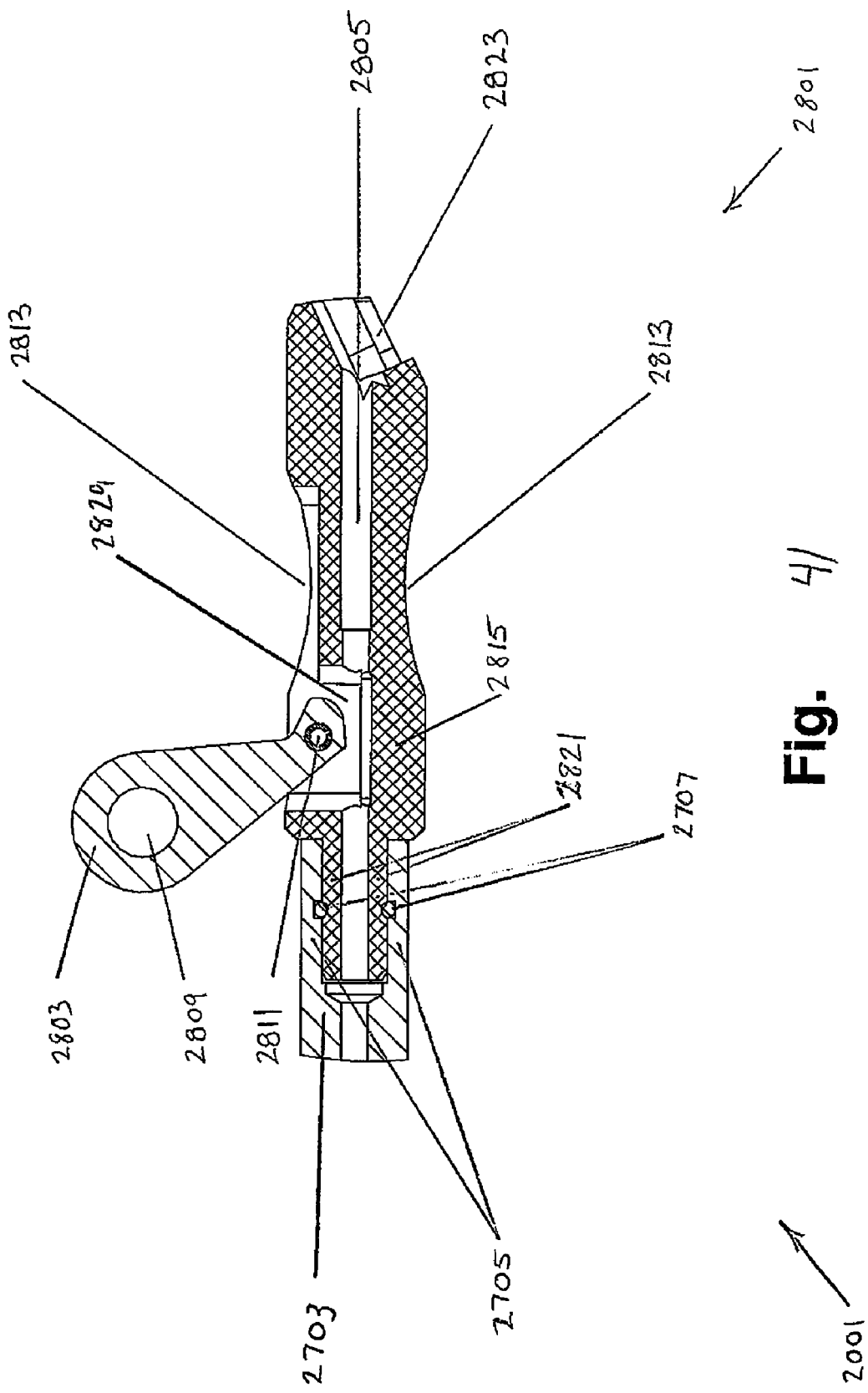
FIG. 41 is a detailed front sectional view of the distal cable clamp assembly of the second embodiment of the pistol grip tensioning apparatus in the initial condition.
Figure 42:
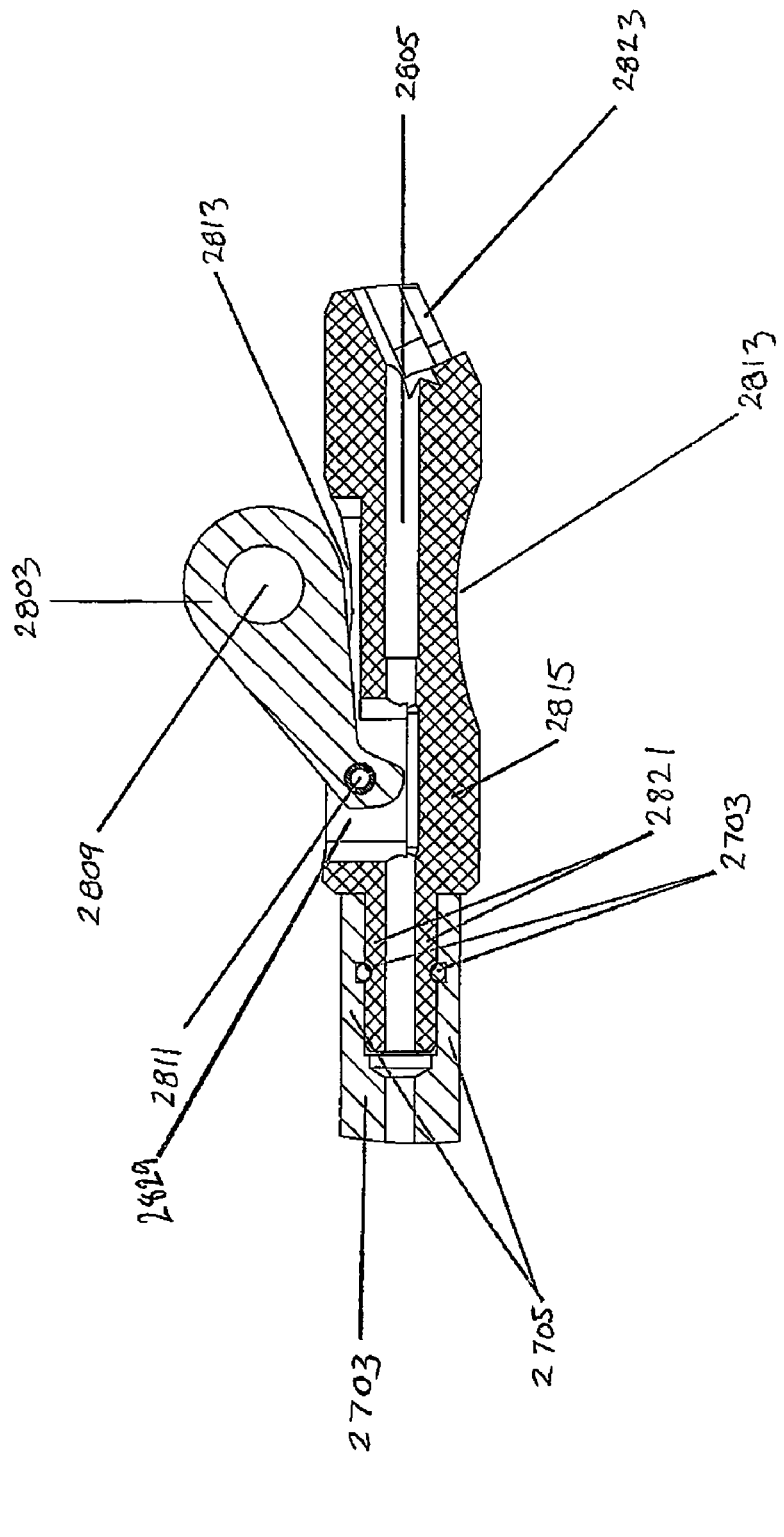
FIG. 42 is a detailed front sectional view of the distal cable clamp assembly of the second embodiment of the pistol grip tensioning apparatus in the secured or locked configuration.
Figure 43:
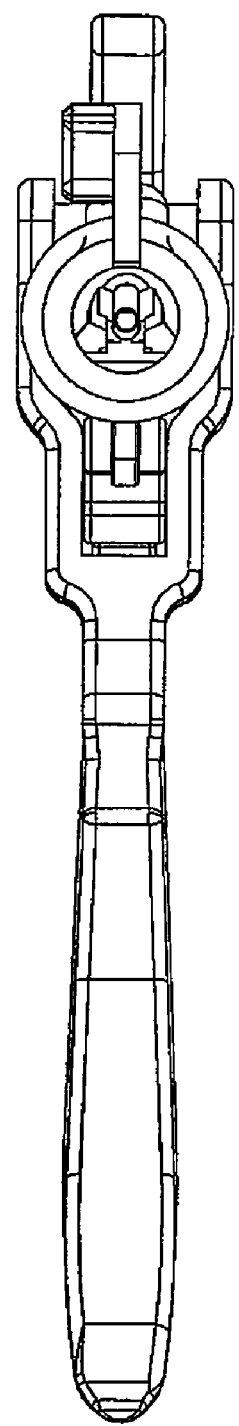
FIG. 43 is a right side view of the second embodiment of the pistol grip tensioning apparatus in the initial condition.
Figure 44:
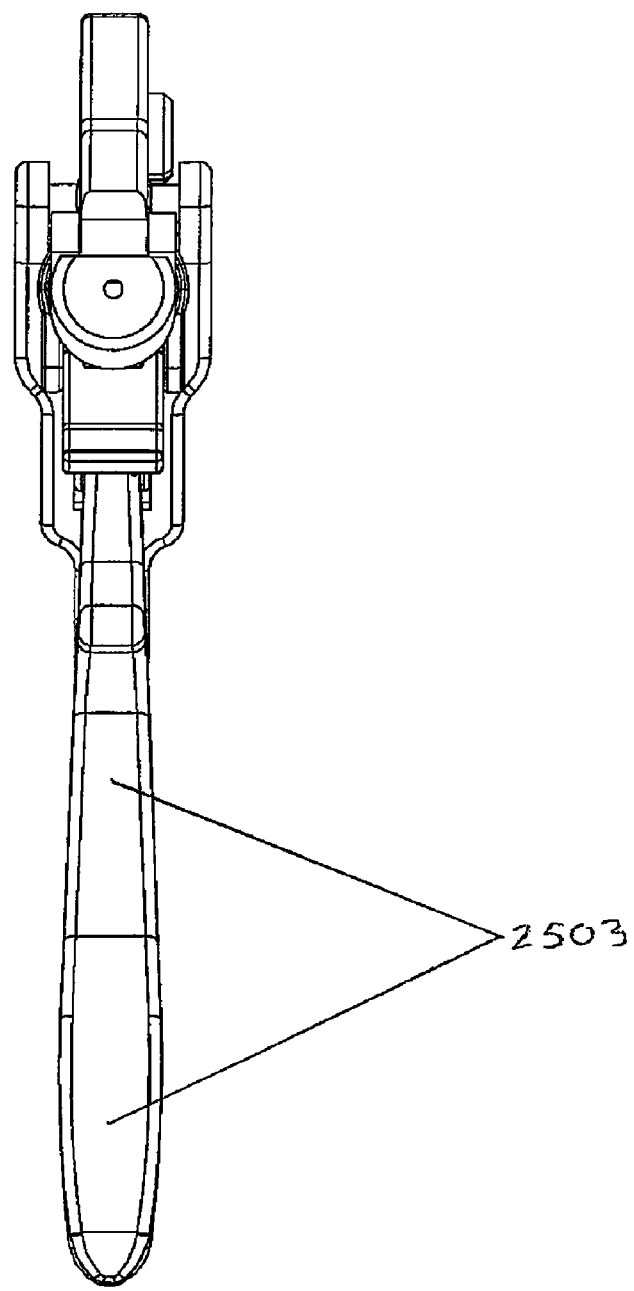
FIG. 44 is a left side view of the second embodiment of the pistol grip tensioning apparatus in the initial condition.

The distal locking clamp assembly 2801 of the second apparatus 2001 shown in FIGS. 41 and 42 is nearly identical to the distal locking clamp assembly 1801 of the first embodiment 1001 described previously. The distal locking clamp assembly 2801 locks surgical cable 12 by rotation of the distal clamp lever 2803 about the cam pin 2811 to cause the distal cam 2807 to directly engage or contact the surgical cable 12 to create friction against movement by the friction force applied by the cam 2807 and the clamp body 2815. However, the distal locking clamp 2801 does not provide the bridging material 1817 or opening 1819 to offset the clamp assembly 2801. In contrast, the distal clamp passage 2805 extends through the clamp assembly 2801 and on through to the entire length of the cable tensioning apparatus 2001 until it connects with the proximal clamp passage 2112 to form a single centrally located cable passageway throughout.

The distal locking clamp assembly 3801 of the third apparatus 3001 shown in FIG. 52 through 57 and FIGS. 60 through 67 is identical to distal locking clamp assembly 1801 of the first apparatus 1001 described previously. Alternatively, the distal and proximal locking clamp assemblies can be substituted for one another, i.e. the proximal clamp assembly can be used both at the proximal and distal portions of the apparatuses (as was done in the fourth apparatus 4001). The distal and proximal clamp assemblies 3801 and 3101 are also operated with the same method but with the alteration of a double action rather than single action friction drive.

Figure 81:
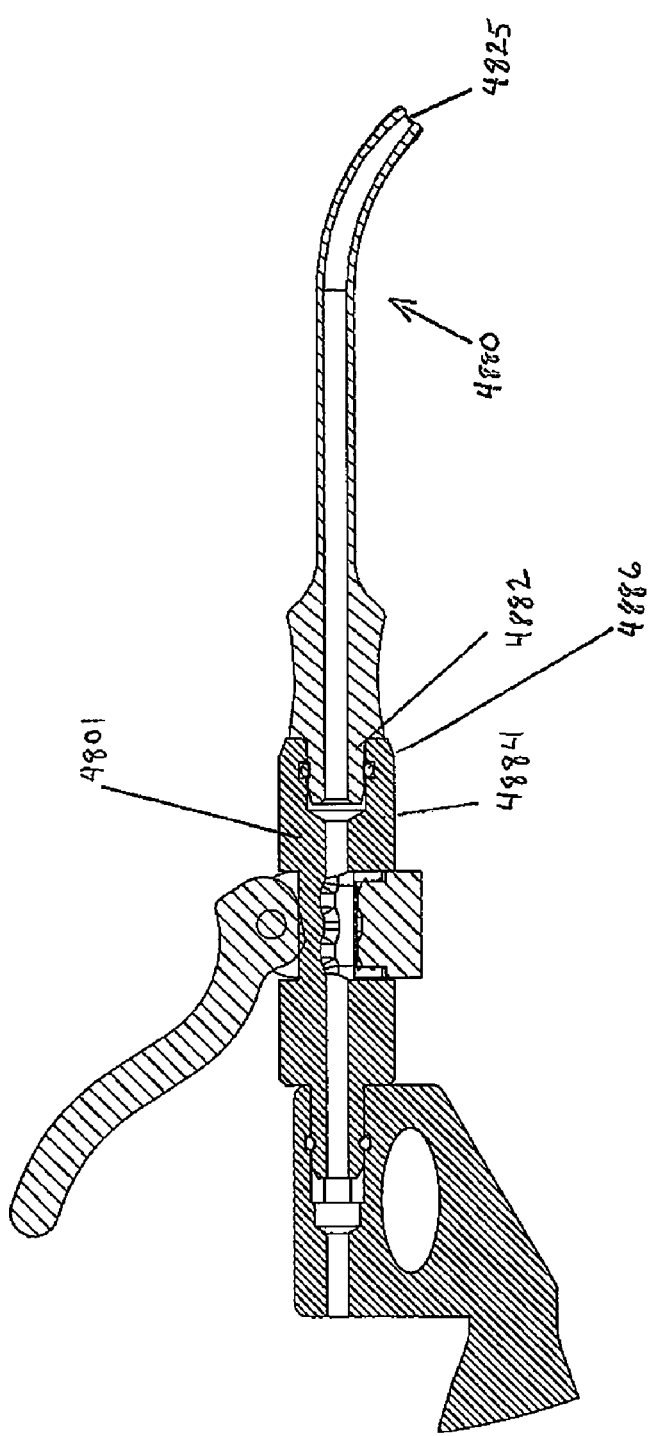
FIG. 81 is a detailed front sectional view of the fourth embodiment of the pistol grip tensioning apparatus in the initial condition.
Figure 82:
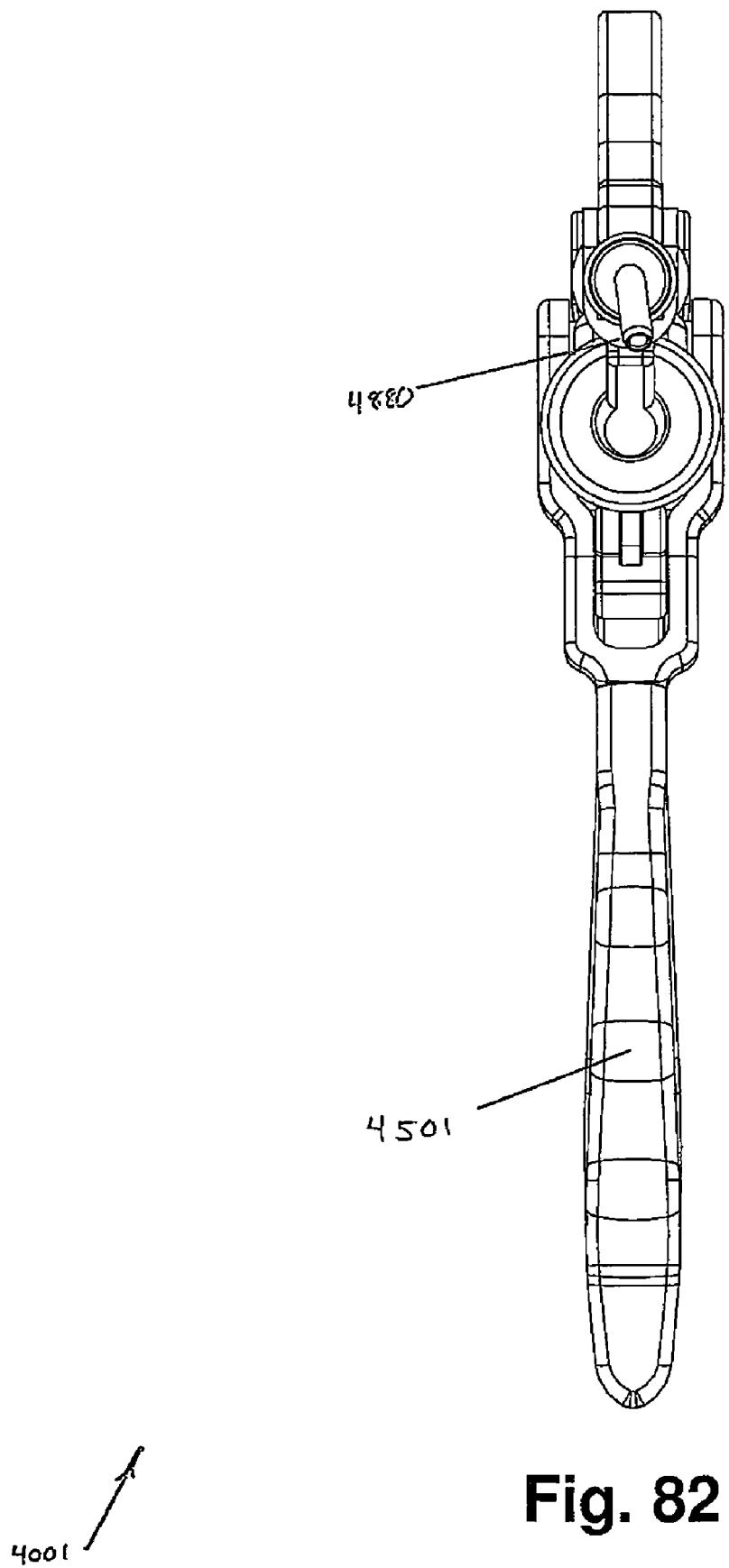
FIG. 82 is a right side view of the fourth embodiment of the pistol grip tensioning apparatus in the initial condition.

The distal cable clamp assembly 4101 for the fourth apparatus 4001, as shown in FIG. 81, has a cable guide assembly 4880 that functions primarily to allow the surgeon access to inaccessible surgical sites. The guide assembly 4880 also may be used to prevent abrupt bending in the cable during application of the tensioning force to the cable 12. The guide assembly 4880 includes a generally cylindrical guide barrel 4882 which is received in a complementarily-shaped clamp socket 4884. A deformable ring 4886 is disposed in a recess and cooperates with an annular recess formed on the outer surface. The ring 4886 and socket 4884 cooperate to allow the cable guide assembly 4880 to be quickly snapped on and off the fourth embodiment of the pistol grip tensioning apparatus 4001. Alternatively, the cable guide assembly 4880 could be used on any of the previous cable tensioning embodiments 1001, 2001, and 3001. The distal cable clamp assembly 4801 for the fourth embodiment 4001 is described in further detail in U.S. Pat. No. 7,452,360, filed Nov. 14, 2001 titled "Method and Apparatus for Clamping Surgical Wires or Cables" which is incorporated by reference in its entirety herein.

Precision Friction Drives

Figure 14:
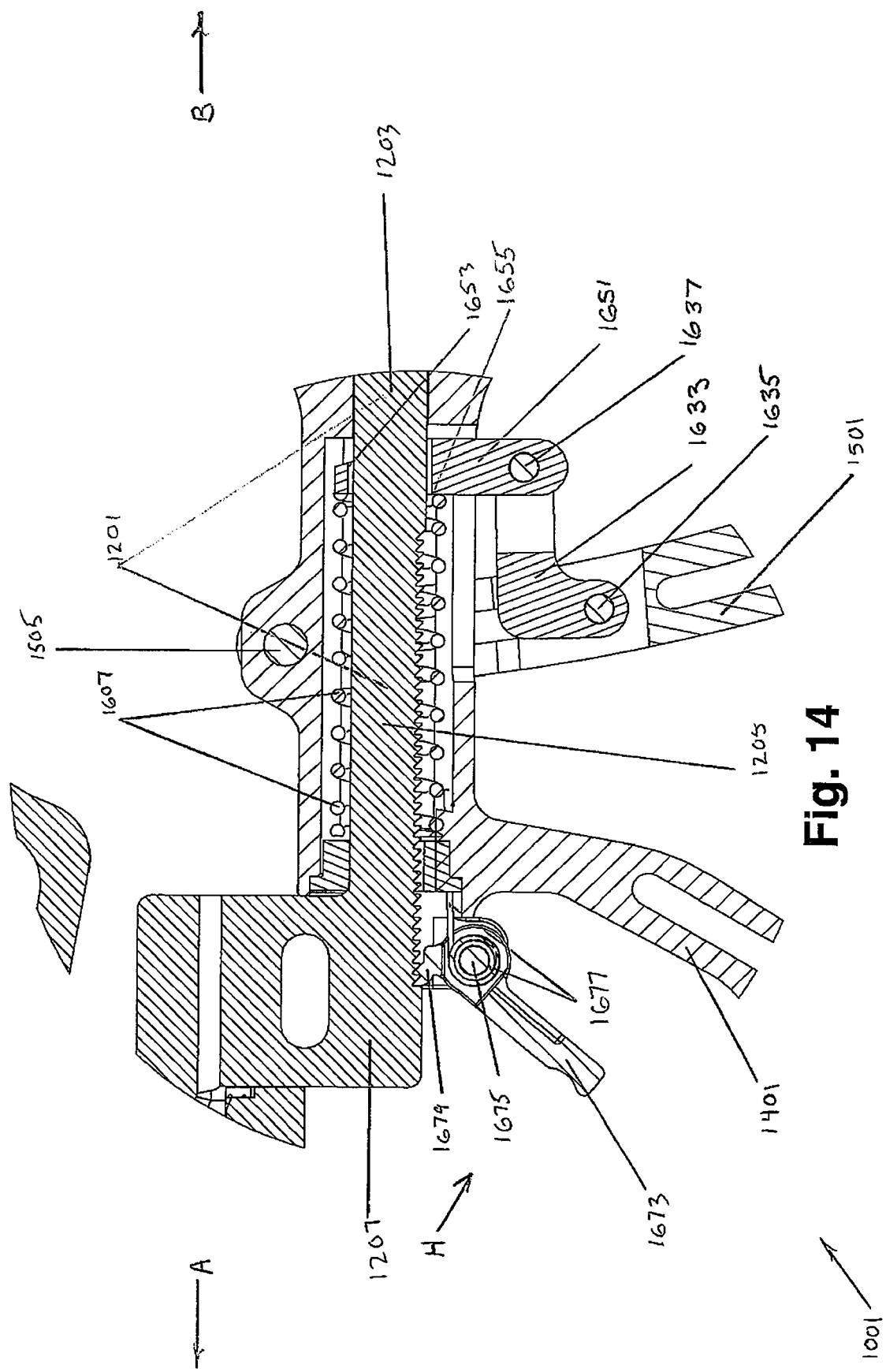
FIG. 14 is a detailed front sectional view of the drive mechanism in the first embodiment of the pistol grip tensioning apparatus in the initial condition.
Figure 15:
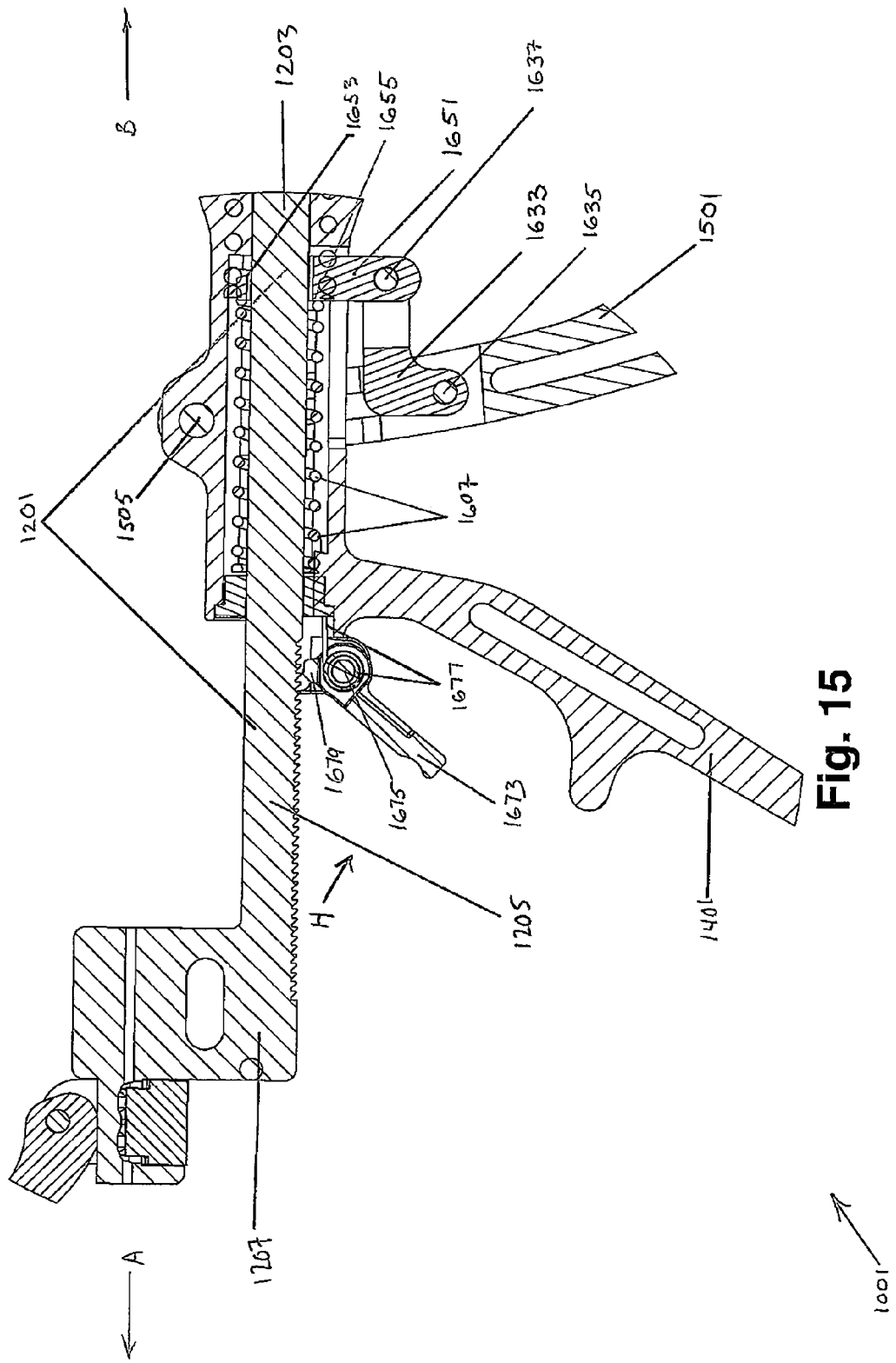
FIG. 15 is a detailed front sectional view of the drive mechanism of the first embodiment of the pistol grip tensioning apparatus in the fully extended condition.
Figure 37:
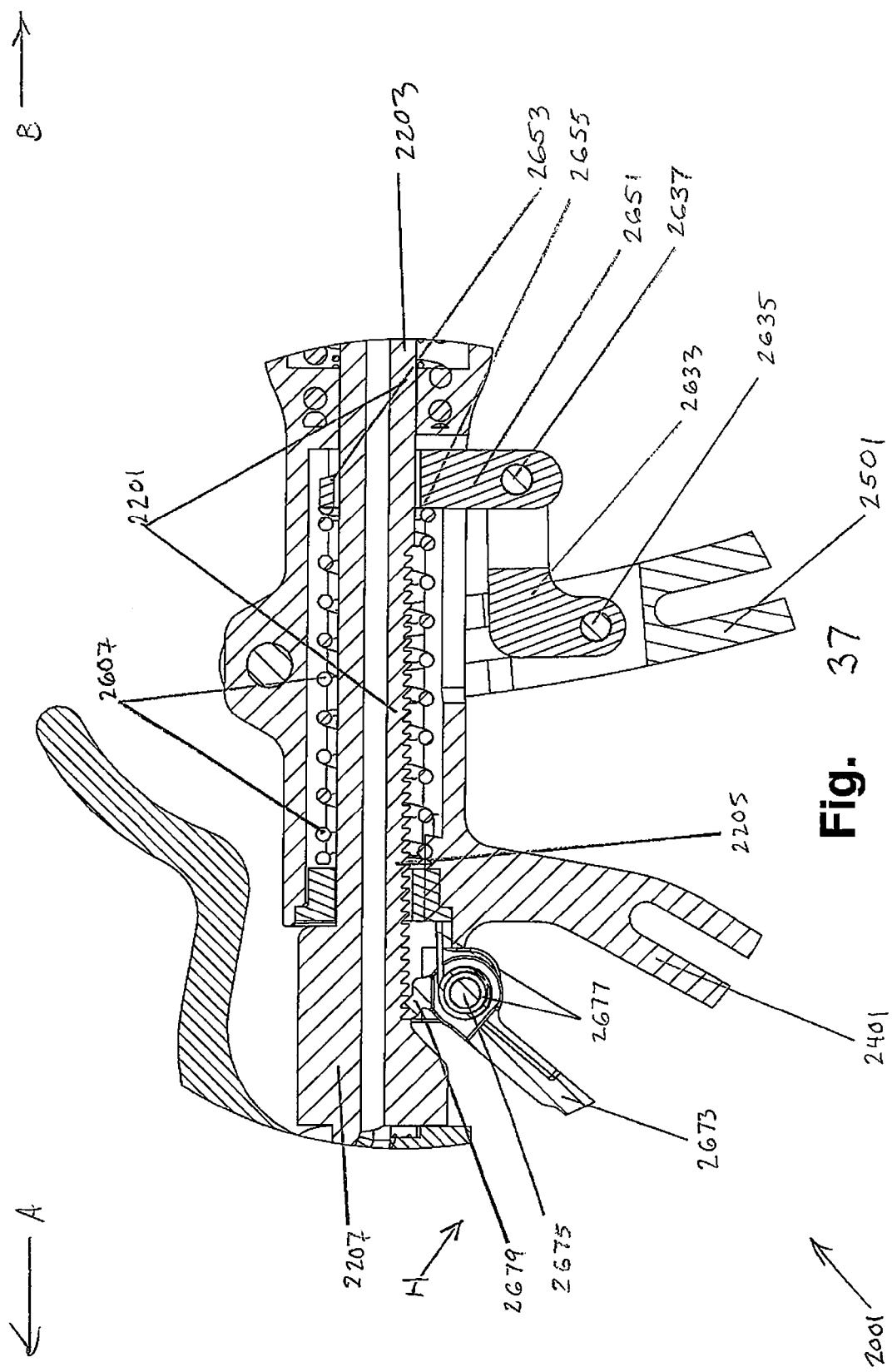
FIG. 37 is a detailed front sectional view of the drive mechanism of the second embodiment of the pistol grip tensioning apparatus in the initial condition.
Figure 38:
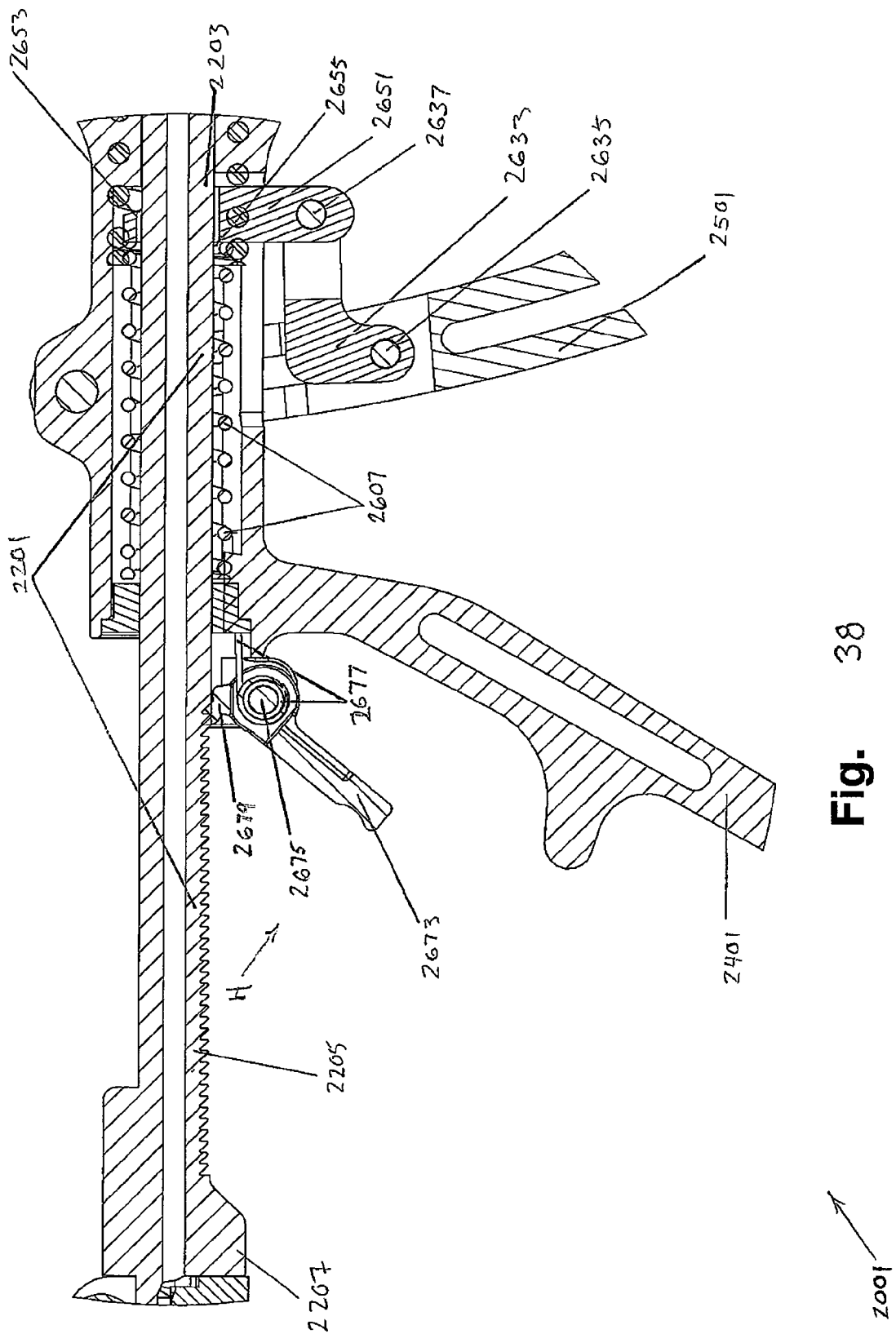
FIG. 38 is a detailed front sectional view of the drive mechanism of the second embodiment of the pistol grip tensioning apparatus in the fully extended condition.
Figure 73:
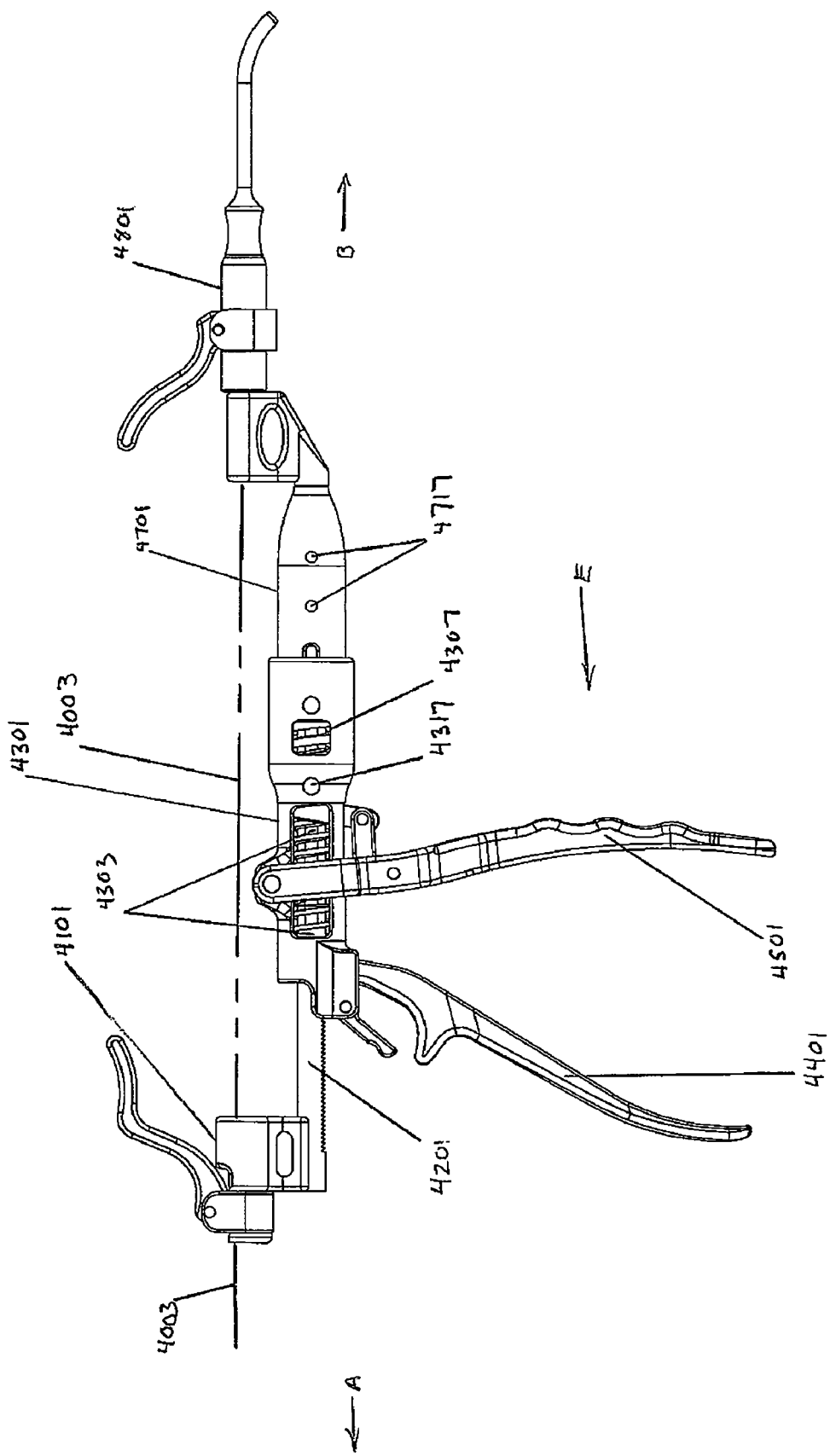
FIG. 73 is a front view of the fourth embodiment of the pistol grip tensioning apparatus in the fully extended condition.
Figure 74:
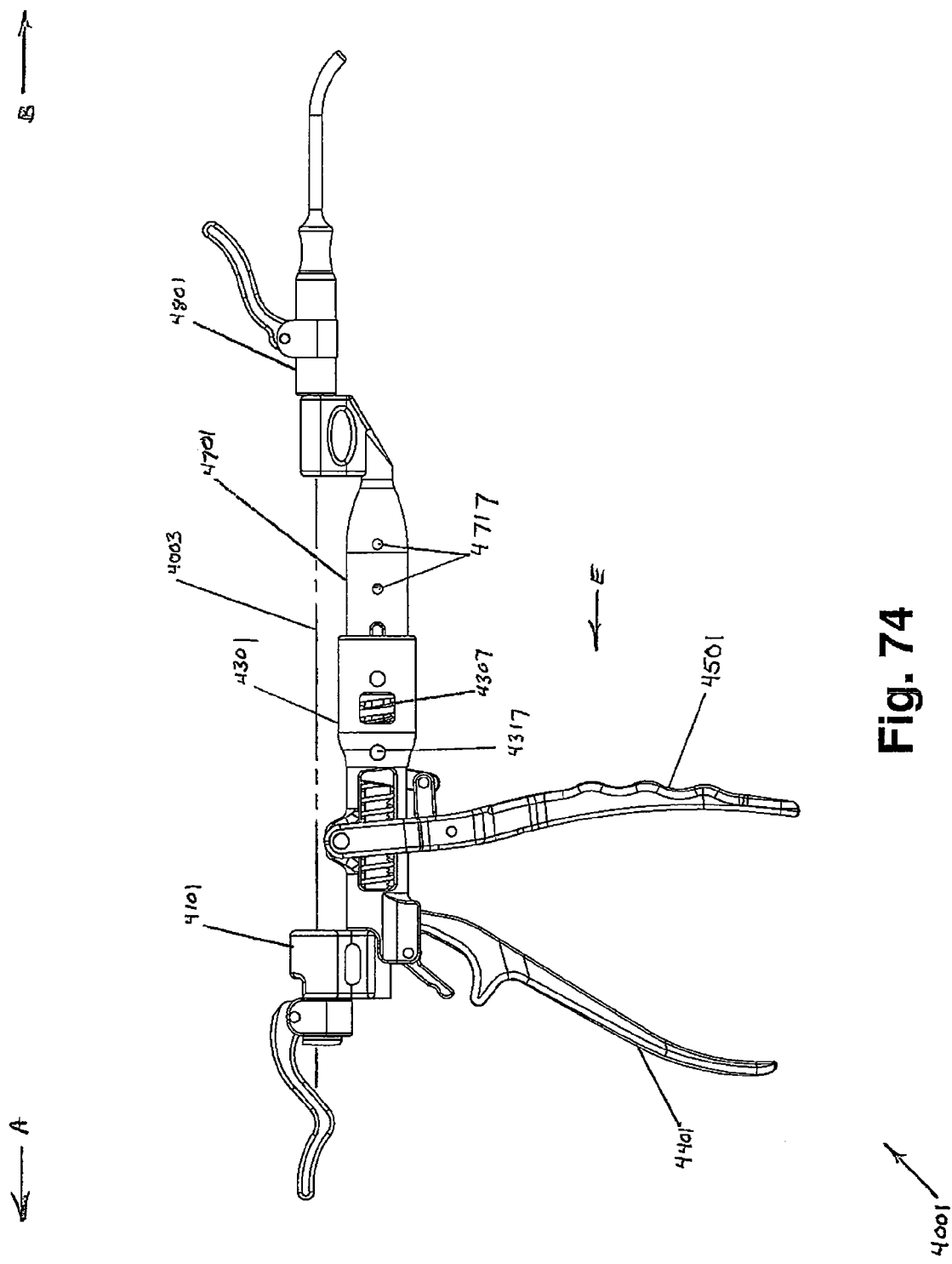
FIG. 74 is a front view of the fourth embodiment of the pistol grip tensioning apparatus in the secured or locked configuration.

The first, second, and fourth embodiments of the cable tensioning apparatuses 1001, 2001 and 4001 rely on a friction drive mechanism 1601 (2601, or 4601) that mechanically engages or locks on to the drive rod 1201 (2201, or 4201) with a canting member 1651 (2651, or 4651), otherwise known as a rocker, and is shown in FIG. 14 (FIG. 37 or FIG. 79). As shown in FIG. 15 (FIG. 38 or FIG. 80), the friction drive mechanism 1601 (2601, or 4601) transmits motion from the lever 1501 (2501, or 4501) to the smooth shaft of the drive rod 1201 (2201, or 4201) via surface friction on the smooth shaft. The friction drive mechanism 1601 (2601, or 4601) causes linear translation of the drive rod 1201 (2201, or 4201) in the rearward or proximal direction A as the lever 1501 (2501, or 4501) is depressed or pulled in direction E as shown in FIG. 7 (FIG. 30 or FIG. 73).

Figure 76:
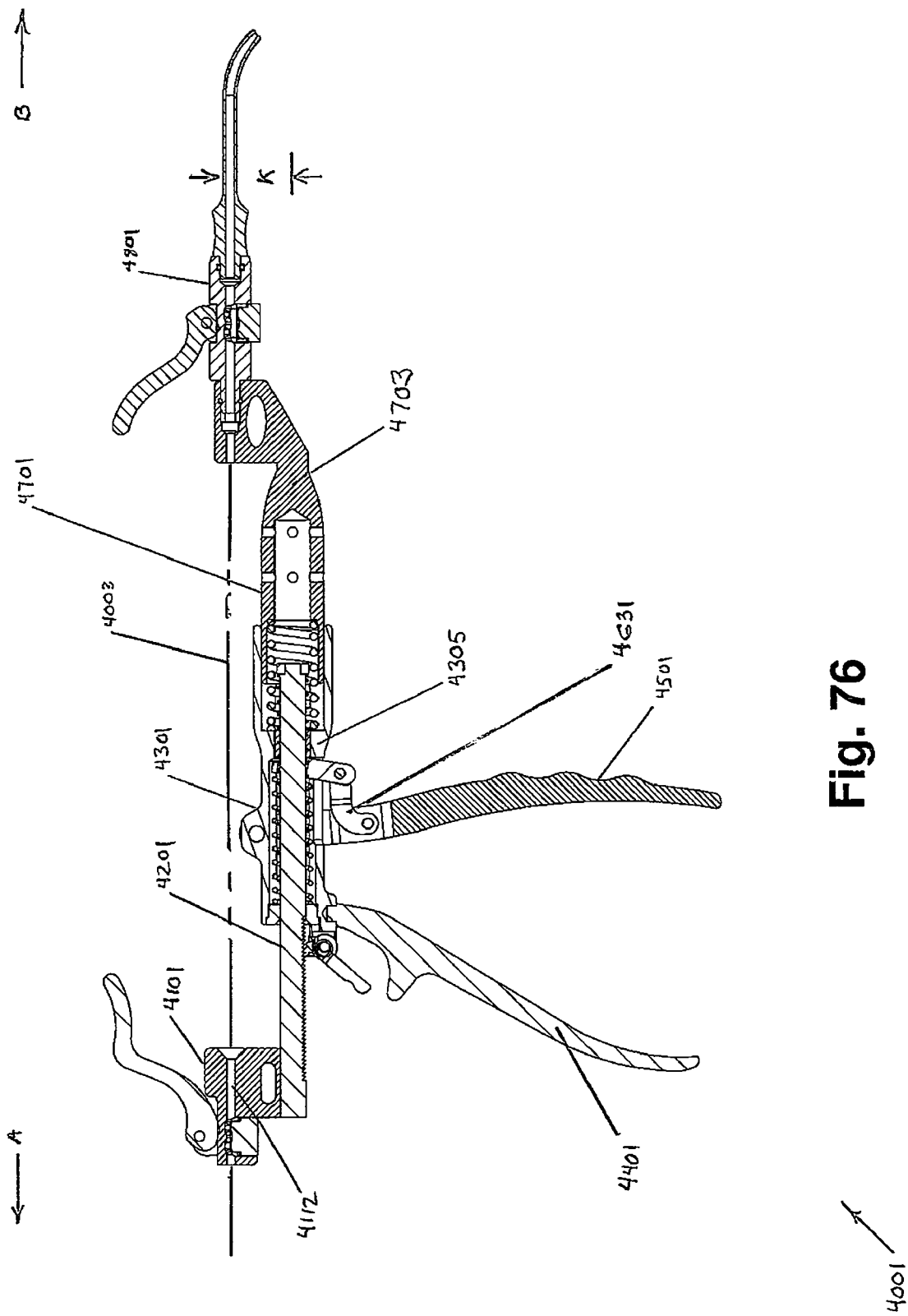
FIG. 76 is a front sectional view of the fourth embodiment of the pistol grip tensioning apparatus in the fully extended condition.
Figure 77:
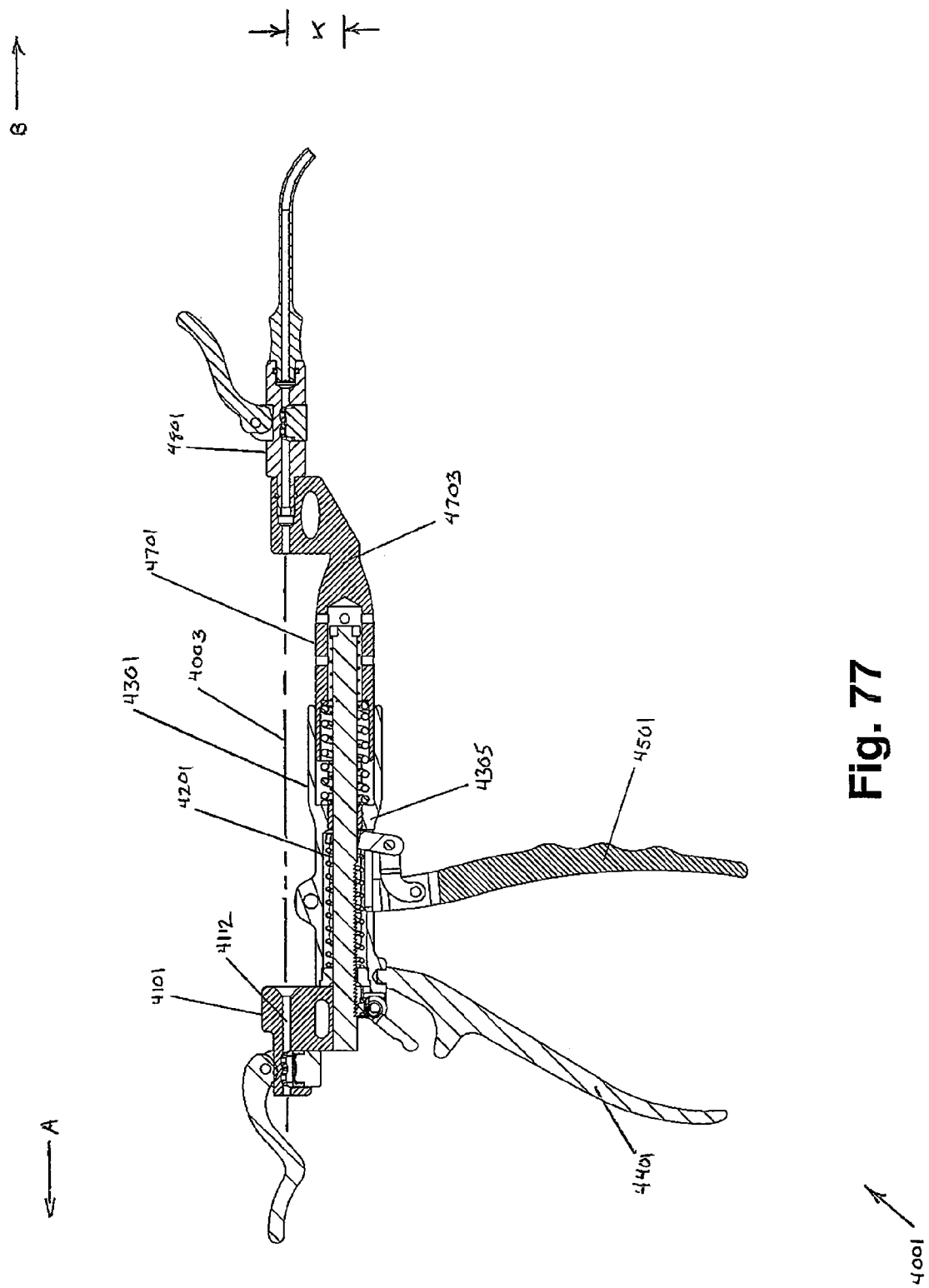
FIG. 77 is front sectional view of the fourth embodiment of the pistol grip tensioning apparatus in the secured or locked configuration.

The illustrated friction drive mechanism 1601 (2601 or 4601) includes the mechanical linkage 1631 (2631 or 4631), and the canting member 1651 (2651 or 4651). A release mechanism 1671 (2671 or 4671) is also provided. The friction drive mechanism 1601 for the first apparatus 1001, shown in FIGS. 10, 14, 15, and 23, is substantially the same as the friction drive mechanism 2601 for the second apparatus 2001, shown in FIGS. 37 and 38, and will not be repeated for brevity. Similarly, friction drive mechanism 4601 for the fourth apparatus 4001 shown in FIGS. 76, 79 and 80 is substantially the same as again to the first apparatus 1001 and will not be repeated for brevity.

Figure 10:
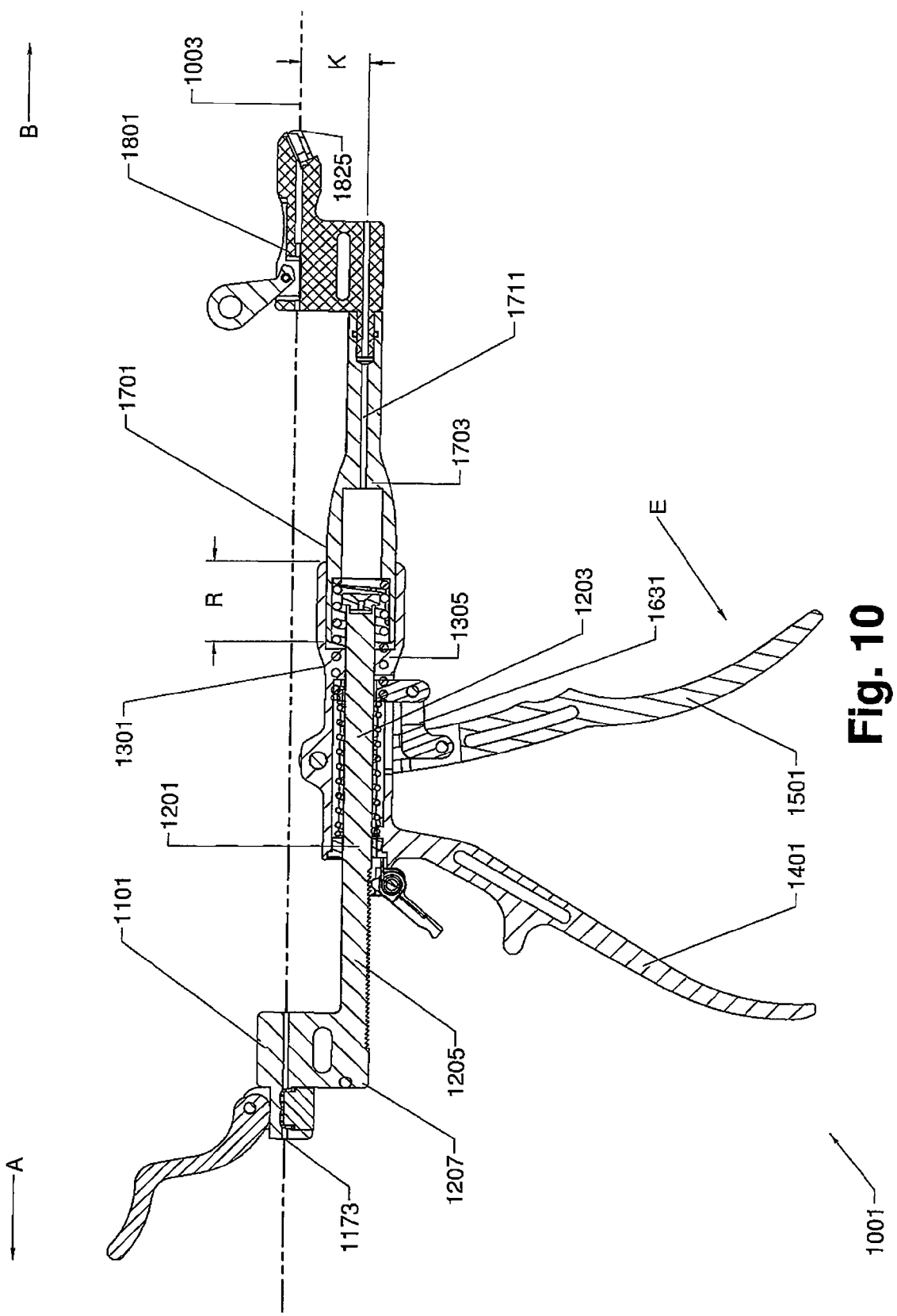
FIG. 10 is a front sectional view of the first embodiment of the pistol grip tensioning apparatus in the fully extended condition.
Figure 11:
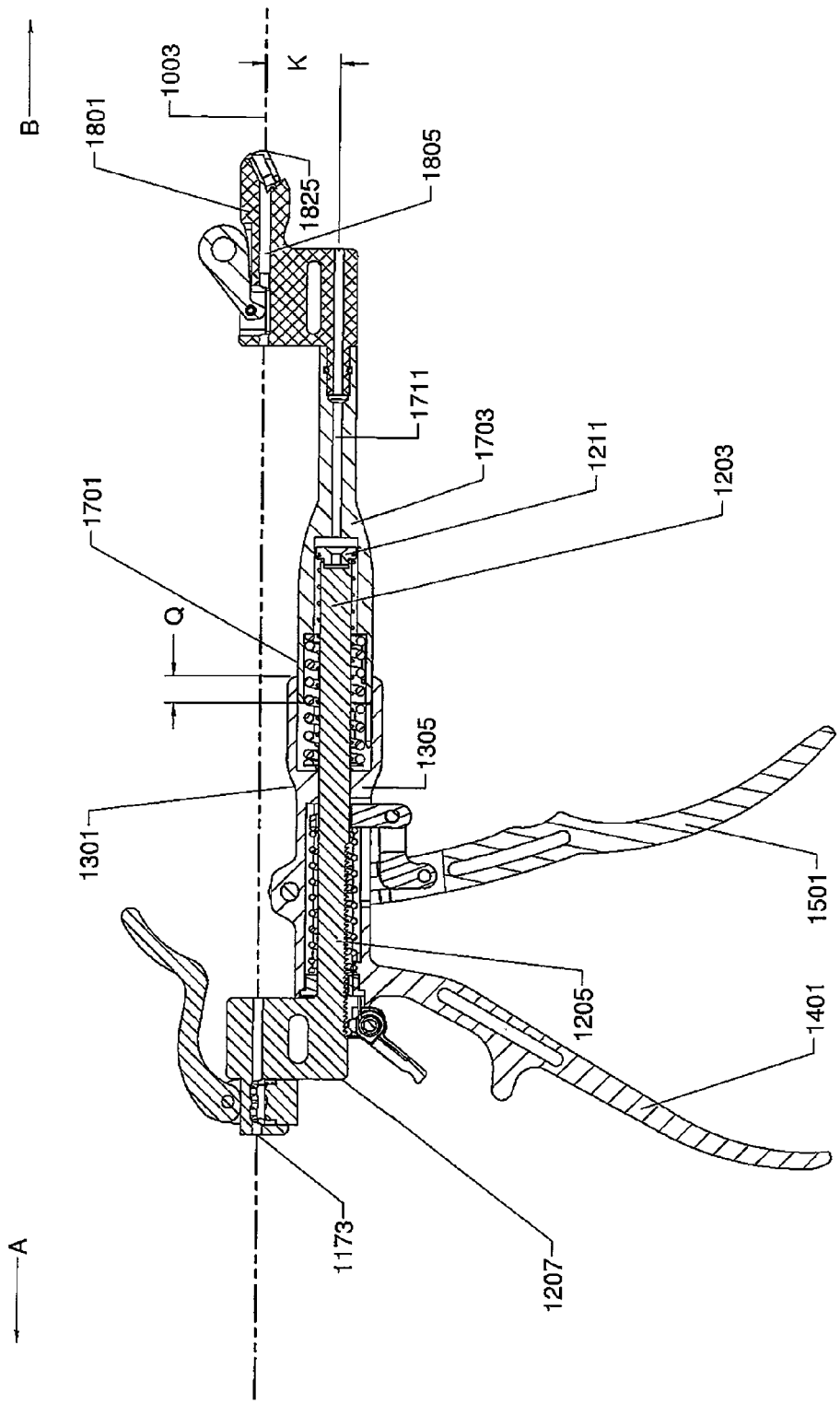
FIG. 11 is a front sectional view of the first embodiment of the pistol grip tensioning apparatus in the secured or locked configuration.

For example, in the first embodiment 1001, a mechanical linkage 1631 is mounted to the lever 1501 as shown in FIG. 10. The lever 1501 is mounted to the housing 1301 by the lever pin 1505. As shown in FIG. 14 the mechanical linkage 1631 is made up of a "L" shaped link member 1633 which is connected to the lever 1501 with the linkage pin 1635. The "L" shaped link member 1633 is connected to the canting member 1651 with the pivot pin 1637. The canting member 1651, which is a ring with a hole, receives the drive rod 1201 through the aperture or hole. The canting member 1651 wraps around the cylindrical portion 1203 of the drive rod 1201. The canting member 1651 can cant or tilt on the cylindrical portion 1203 of the drive rod 1201 as well as shift along the length of the rod 1201. The canting member 1651 structure can be seen and its relation to the drive mechanism 1601 in FIG. 23.

As shown in FIGS. 10 and 15, the operator applies a force on the lever 1501 in direction E which is transfer to the "L" shaped linkage 1633. The lever 1501 transfers the force from the operator and transmits a force multiplied approximately three times to the "L" shaped linkage 1633. The multiplied force is applied in the proximal direction A on the pivot pin 1637 to the canting member 1651. This proximal force causes the canting member 1651 to cant or tilt to the right, i.e. to rock into position. The force applied in the proximal direction A at the pivot pin 1637 is applied to the cylindrical portion 1203 of the drive rod 1201 in the proximal direction A via frictional engagement. The frictional engagement force causes the drive rod 1201 to shift, i.e. a proximal linear translation, with the locked cable 12 to the rear, i.e. proximal direction A.

The friction engagement creates a mechanical feedback loop whereby the proximal force is balanced by friction forces at the canting annular top portion 1653 and canting bottom leg portion 1655. As more tensile force is applied by the drive rod 1201 in the distal direction B then a corresponding increase in friction and normal forces will be created in the canting annular top and bottom leg portions 1653 and 1655. In other words, the greater the tension on the drive rod 1201 and cable 12 then the greater the traction for the friction drive mechanism 1601.

A release mechanism 1671 is mounted to the housing member 1301 (or 2301). The release mechanism 1671 is made up of a release lever 1673 which is connected to the housing 1301 with the release pin 1675 as shown in FIG. 14.

Figure 21:
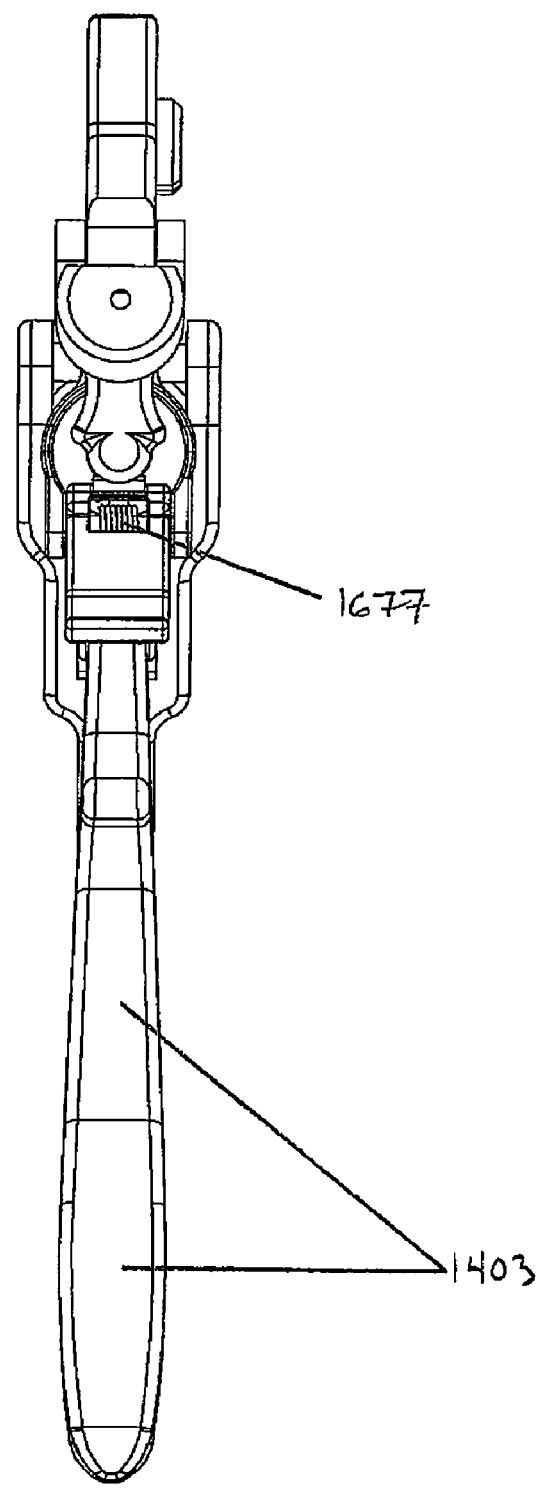
FIG. 21 is a left side view of the first embodiment of the pistol grip tensioning apparatus in the initial condition.
Figure 22:
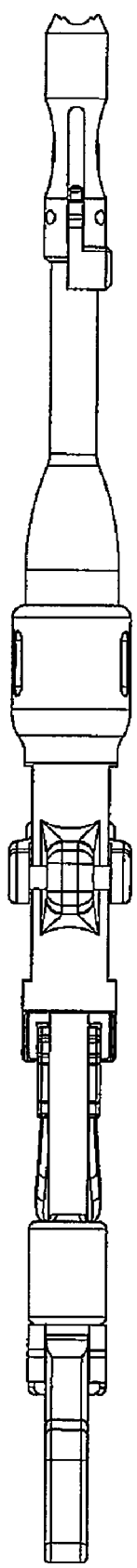
FIG. 22 is a top view of the first embodiment of the pistol grip tensioning apparatus.
Figure 23:
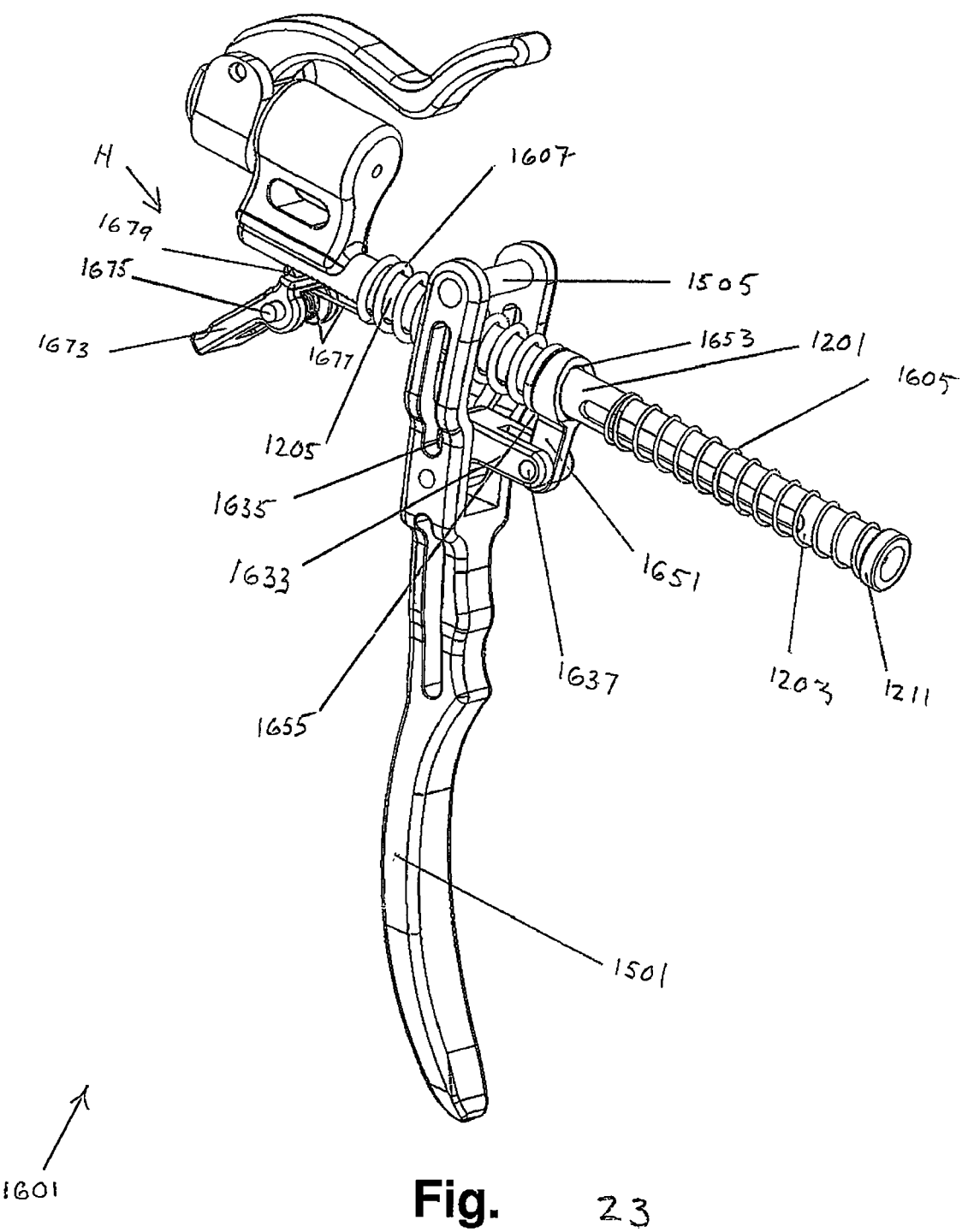
FIG. 23 is a perspective view of the drive mechanism of the pistol grip tensioning apparatus of the first embodiment in the initial condition.

A torsion spring 1677 is also part of the release mechanism 1671 and mounted to the release pin 1675 to maintain the bias of the release lever 1673 to the proximal direction A as shown in FIGS. 14, 15, and 21. A pawl 1679 is counterpoised to the release lever 1673 and mounted by the release pin 1675 to provide the last component of the release mechanism 1671.

As shown in FIGS. 10 and 15, the operator applies pressure on the release lever 1673 in direction H against its bias force for actuation of the release of the pawl 1679 to have disengagement from the rack portion 1205 of the drive rod 1201. The pawl 1679 should only be disengaged when the drive rod 1201 reaches the end of its travel and needs to be reset. Once the pawl 1679 is disengaged and the lever 1160 returned to its original position as shown in FIG. 15 then the drive rod 1201 will shift in the distal direction B until the drive rod 1201 returns to its original position as shown in FIG. 14. The drive rod 1201 returns to the original position because the drive rod reset spring 1605 which was compressed during tensioning then decompresses through expansion of the spring to return the drive rod 1201 to the initial position as shown in FIG. 14.

The release mechanism 1671 primarily functions to allow for rapid resetting of the cable tensioning apparatus 1001 by depressing the release lever 1673 in direction H which acts as a trigger. The release mechanism 1671 allows the tensioning process to repeat once the drive rod 1201 reaches the end of its travel to allow more cable 12 to be drawn. The release mechanism 1671 allows the repeated translation of the drive rod 1201, i.e. the repetition of rod 1201 moving in the opposite proximal and distal directions A and B. The repeated translation of the rod 1201 used in combination with the proximal clamp 1101 and distal clamp 1801 assemblies allow for the tightening of a potentially infinite length of cable 12.

The release mechanism 1671 also prevents the drive rod 1201 from moving in the distal direction B once the lever 1501 reaches the end of its stroke in direction E and returns to its original position. The lever 1501 automatically returns to its original position because the canting member return spring 1607 which was compressed during tensioning then decompresses to return the lever 1501 to the initial position as shown in FIG. 15.

The release mechanism 1671 allows the repeated depression of the lever 1501 without distal linear translation of the drive rod 1201, i.e. slipping of the drive rod 1201 in the distal direction when the lever 1501 is released. There is very little friction created by the canting member 1651 moving in the distal direction B because the canting member 1651 rocks back or tilts back to a vertical position to allow the canting member 1651 to easily slide or shift on the drive rod 1201.

The canting member return spring 1607 shifts the canting member 1651 back in the distal direction B to reset the canting member 1651 for another stroke or depression of the lever 1501. However, the friction drive mechanism 1601 never acts on the ratchet teeth to drive the cable 12 in the proximal direction A to create tension, but only to prevent back sliding of the drive rod 1201 during the lever 1501 return stroke.

The overall travel, rapidity and amount of cable 12 which can feed into the cable tensioning apparatus 1001 is improved because of the friction drive mechanism 1601 since the linkage causes the drive rod 1201 to travel farther with each depression of the lever 1501 than other devices. The cable tensioning apparatus 1001 is also more precise because the leverage created by the lever 1501 whose force is multiplied by the mechanical linkage 1631 allows infinite variability during the setting of the tension in the surgical cable 12. The infinite variability in setting the cable tension 1001 with the friction drive mechanism 1601 is immediately before the final locking of the distal clamp assembly 1801 and is a significant improvement over intermittent mechanical engagement such as on ratchet teeth during tensioning.

The improvement is significant because engagement on ratchet teeth has finite variability due to the necessity of meshing with the teeth and incumbent backlash present in the teeth. The engagement on ratchet teeth with a lever is also imprecise in controlling tension due to the variable shape of the ratchet teeth rather than the linear translation of leverage by the canting member 1651 to the linear drive rod 1201.

In one embodiment, the canting member 1651 has a generally diamond shaped aperture that connects to the cylindrical portion 1203 of the drive rod 1201. Alternatively, the canting member 1651 can have a circular, arcuate or elliptical aperture to frictionally engage the circular drive rod 1201. However, almost any set of geometries for drive rods can be conceived such as square, hexagonal, or triangular with matching apertures for canting members could be used as alternative means with the friction drive mechanism 1601.

Furthermore, the friction drive mechanism 1601 can alternatively utilize drive wheels, roller bearings, or clutch mechanisms to provide for the friction drive mechanism 1601 as alternative means in addition to the drive disclosed in the third embodiment 3001. For example, the linear motion from the lever 1501 can be converted into rotation via a rack and pinion to rotate a wheel or roller bearing that comes into contact with the drive rod 1201 for an alternative friction drive.

Again, the friction drive mechanism 1601 for the first apparatus 1001 is substantially the same as the friction drive mechanism 2601, 4601 for the second and fourth apparatuses 2001, 4001. The detailed description previously recited applies equally to those apparatuses 2001, 4001 and is not repeated.

Figure 56:
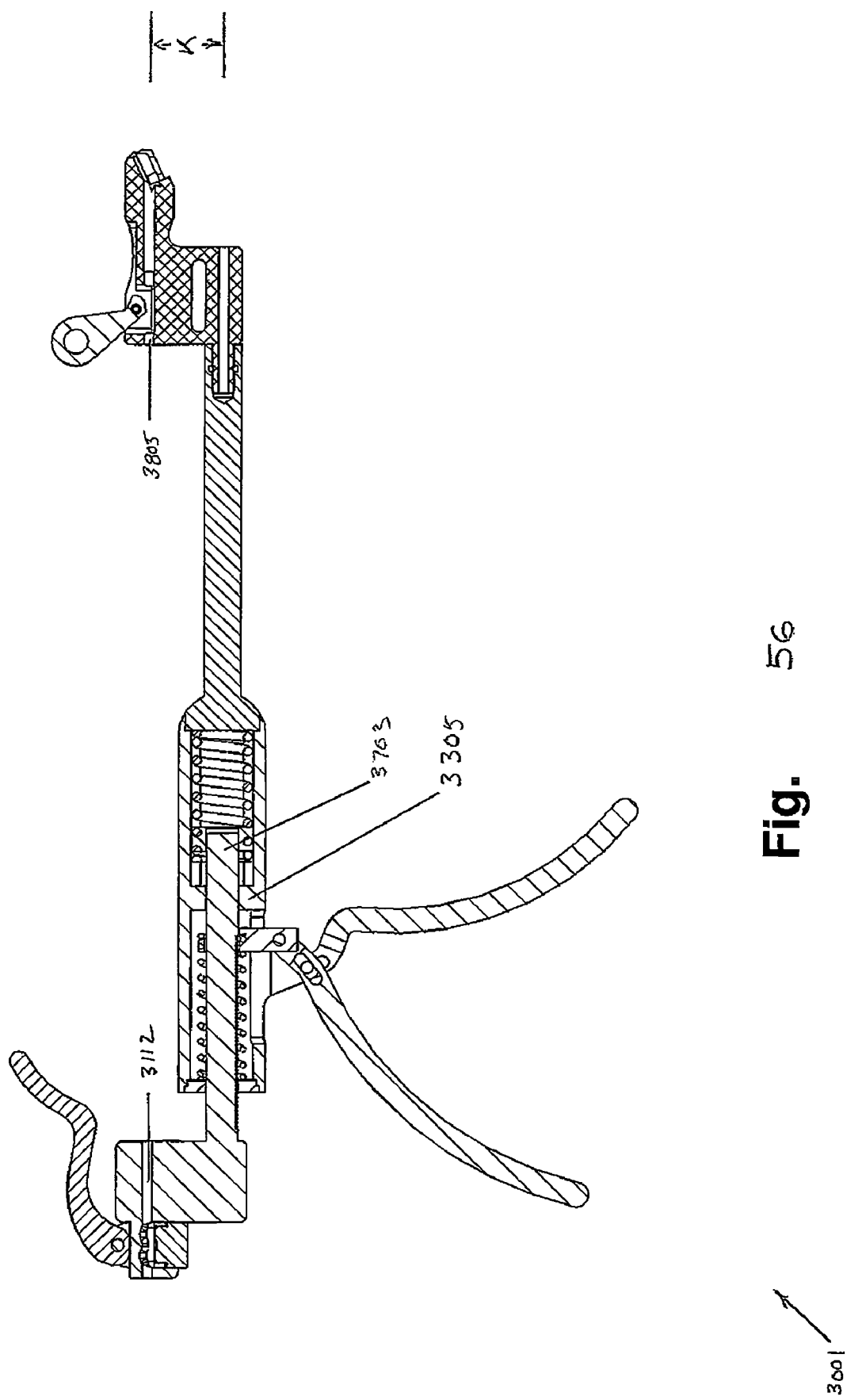
FIG. 56 is a front sectional view of the third embodiment of the pistol grip tensioning apparatus in the initial condition.
Figure 57:
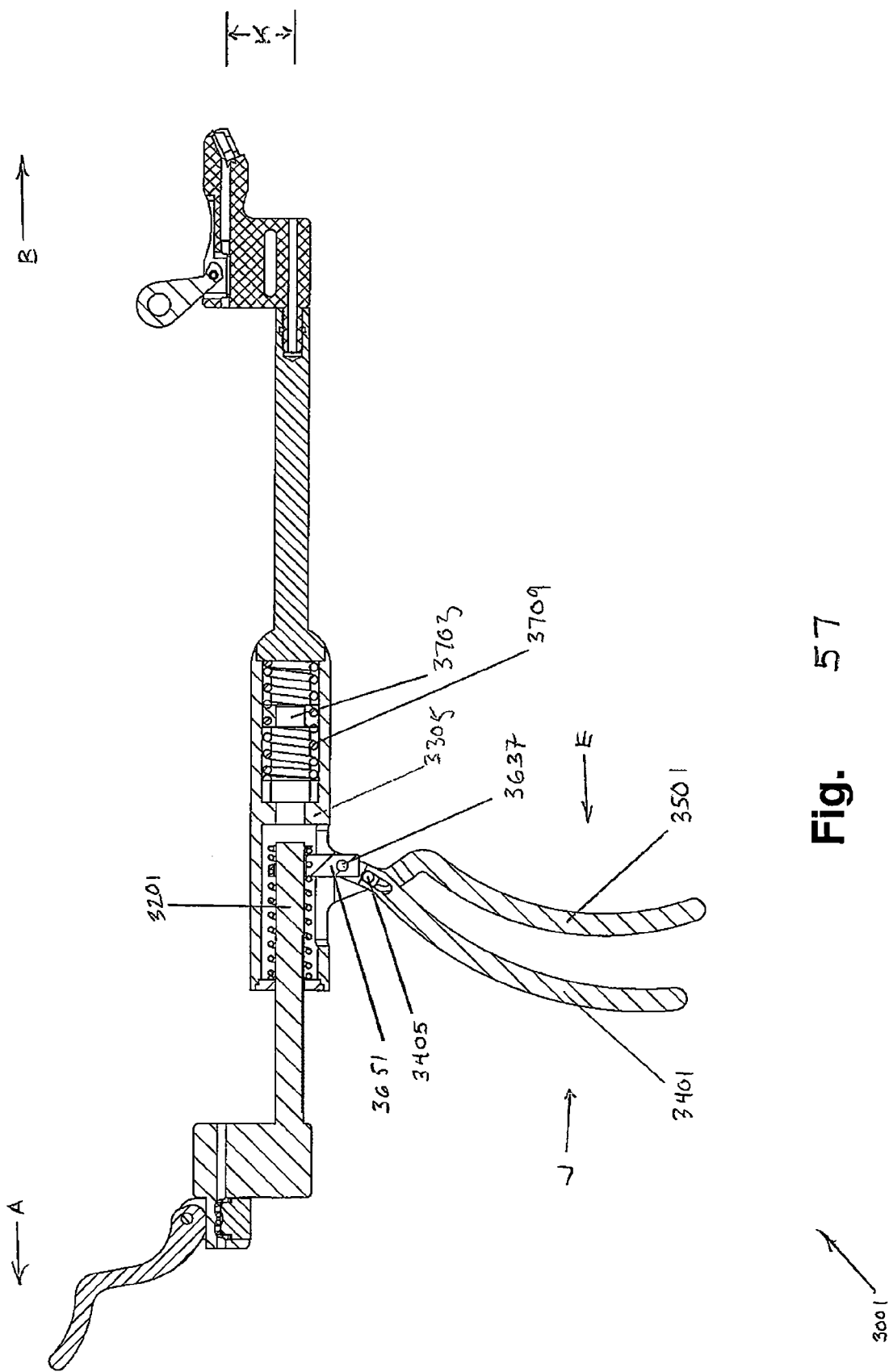
FIG. 57 is a front sectional view of the third embodiment of the pistol grip tensioning apparatus in the fully extended condition.

However, the third embodiment drive mechanism 3601 is distinct. The third apparatus 3001 is composed of a handle 3401 and a lever 3501 which again operates a friction drive 3601 as shown in FIGS. 55 and 56. The operator operates the third apparatus 3001 by compressing the handle 3401 and the lever 3501. The distal handle 3401 shifts the drive rod 3201 in the proximal direction A to tension the cable 12. The friction drive 3601 is mechanically connected to the handle 3401 to cause the drive rod 3201 to shift in the proximal direction A through frictional engagement of the drive rod 3201.

Figure 58:
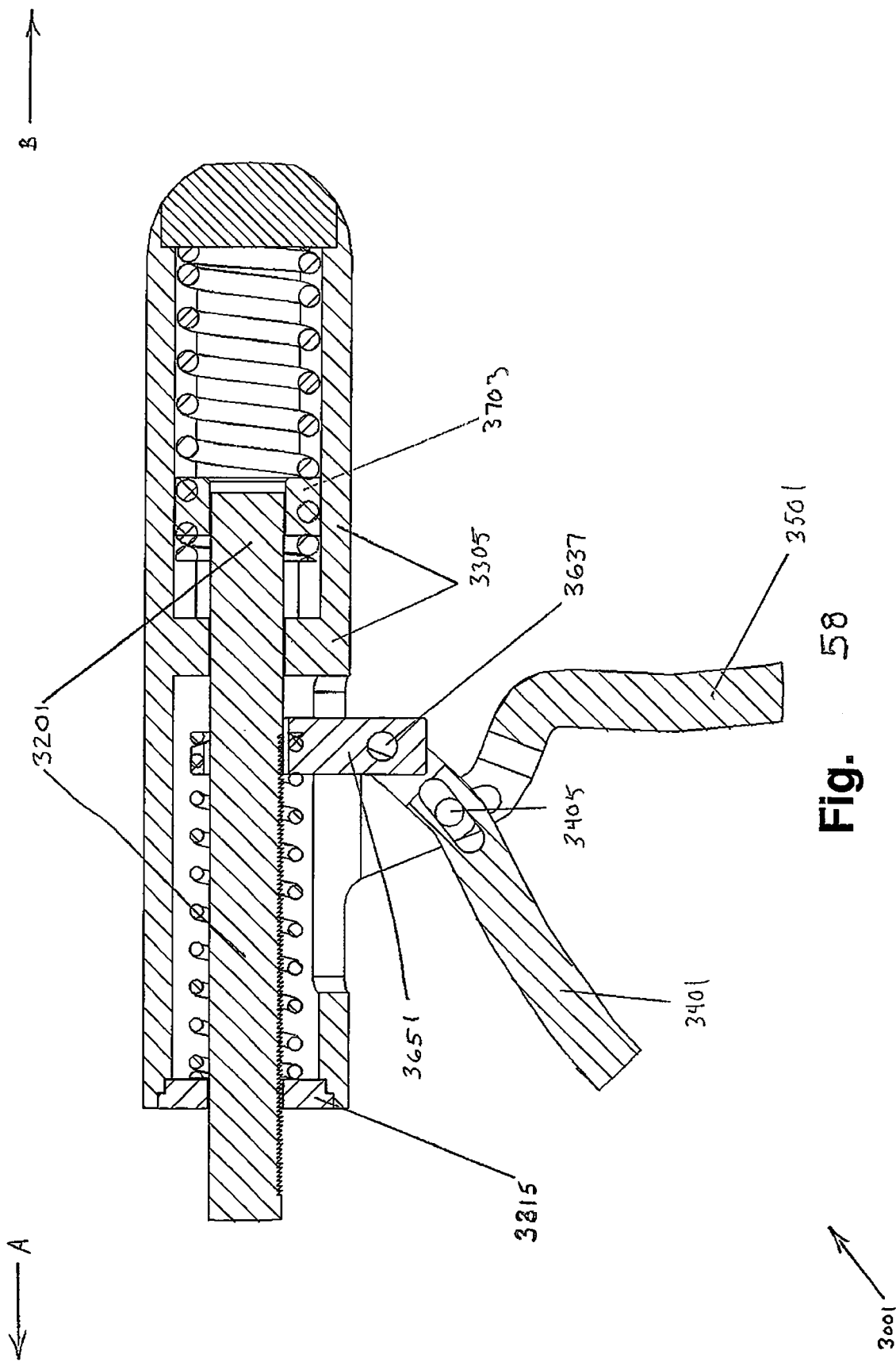
FIG. 58 is a detailed front sectional view of the drive mechanism in the third embodiment of the pistol grip tensioning apparatus in the initial condition.

As the handle 3401 shifts in the distal direction B, the handle pin 3405, which connects the lever 3501 and handle 3401, shifts the lever 3501 in the distal direction B. The handle 3401 is connected to the pivot pin 3637 which multiplies the force on the pivot pin 3637 through leverage on the handle pin 3405 in the proximal direction A. As shown in FIGS. 58 and 59, the pivot pin 3637 then causes the canting member 3651 to cant or tilt and to frictionally engage the drive rod 3201 as described previously for the drive mechanisms 1601 of the first apparatus 1001. Alternatively, the release mechanism 1671 shown in the first apparatus 1001 can be added to the third apparatus 3001 of the cable tensioning apparatus 3001 to extend the amount of travel of the drive rod 3201.

Figure 75:
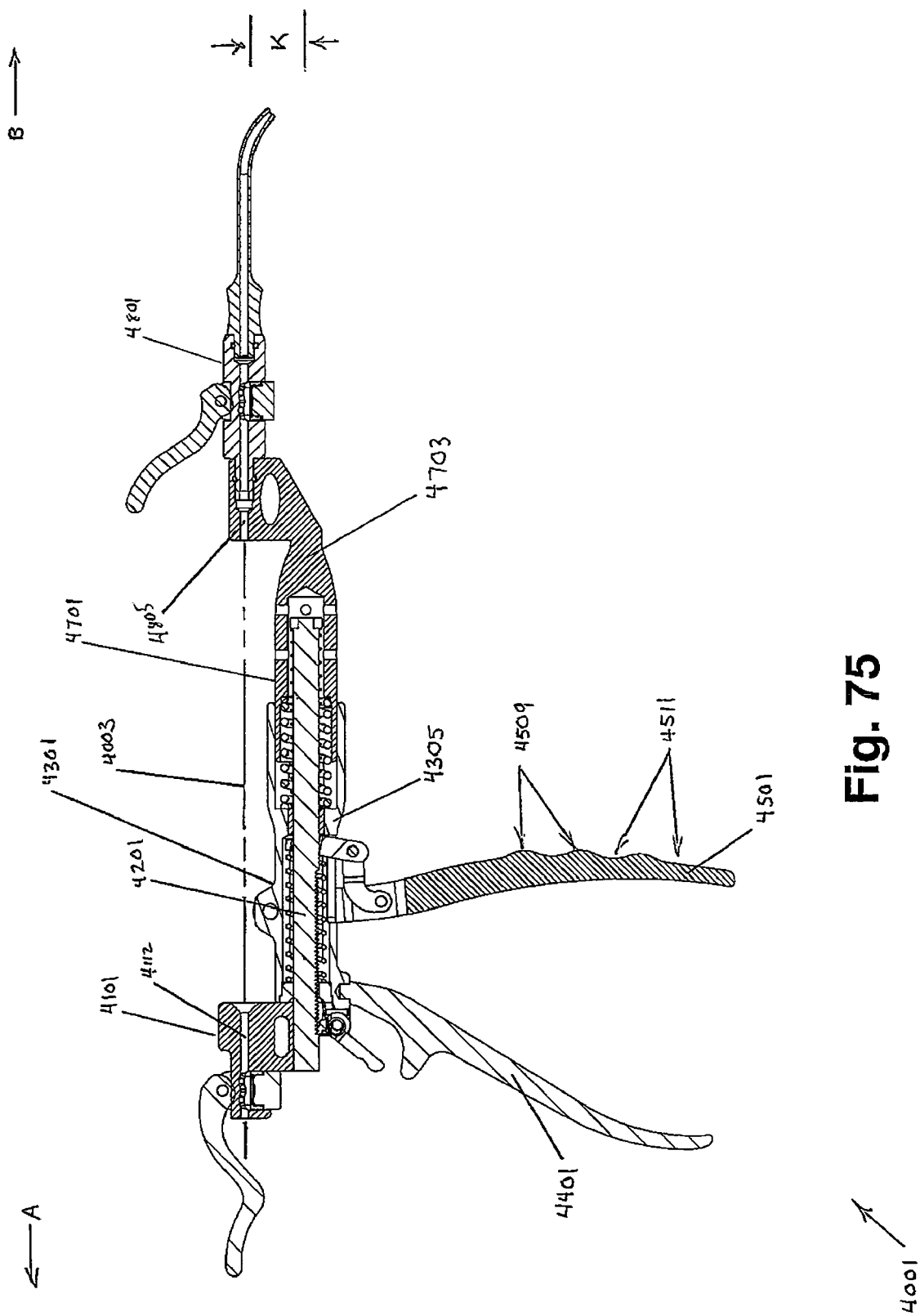
FIG. 75 is a front sectional view of the fourth embodiment of the pistol grip tensioning apparatus in the initial condition.

The fourth apparatus 4001 is again composed of a handle 4401 and a lever 4501 which again operates a friction drive as shown in FIG. 75. However, the lever 4501 of the fourth apparatus 4001 has been reversed in concavity with ridges 4509 and finger detents 4511 to improve the grip of the gloved hands of the surgeon when the instrument 4001 is soiled, i.e. slick with blood. Alternatively, the reversed concavity and ridges of the lever 4501 can be utilized by the other apparatuses 1001, 2001, and 3001 for both the lever and the handle. The various embodiments of the lever and handle are alternative means for solving the same problem and are only an exemplar of the contemplated cable tensioning apparatus.

Tension Indicator Mechanism

When the cable 12 is tensioned in conjunction with a trochanter connector 300 as shown in FIG. 45 or a surgical connector 10 as shown in FIG. 46 through 51 by the cable tensioning apparatus 1001, 2001, 3001 and 4001 then the trochanter connector 300 or surgical connector 10 will apply an approximately equal compressive force against the distal cable clamp assembly 1801 (2801, 3801, 4801) and the tension indicator 1701 (2701, 3701, 4701). This compressive force is measured by the tension indicator mechanism 1701 (2701, 3701, 4701) to prevent the operator from over tensioning of the cable 12 on bones such as a femur 150 shown in FIG. 45 from damage due to fracture or cutting by the cable 12.

The tension indicator mechanism 1701 for the first apparatus 1001 is substantially the same as the tension indicator mechanism 2701, 4701 for the second and fourth apparatuses 2001, 4001 and will not be repeated for brevity. The tension indicator 1701 has two extreme conditions; the initial uncompressed condition shown in FIG. 9 and a fully extended compressed condition shown in FIG. 10. As seen in FIG. 9, the first condition is an uncompressed calibrated compression spring 1709 shown by distance Q when the cable tensioning apparatus 1001 is in its first uncompressed configuration. As shown in FIG. 10, the second condition is a fully compressed calibrated compression spring 1709 is shown by distance R when the cable tensioning apparatus 1001 is in its fully compressed configuration.

The change in position of the indicator structure 1703 indicates the tension in the surgical cable 12. The indicator structure 1703 is able to change position in relation to the tension on the cable 12 because of the bayonet connection. The bayonet lugs 1309 of the housing structure 1305 allows the indicator structure 1703 to adjust position based on the amount of compression created on the calibrated compression spring 1709 because the housing structure 1305 shifts as a sleeve over the indicator structure 1703.

Figure 17:
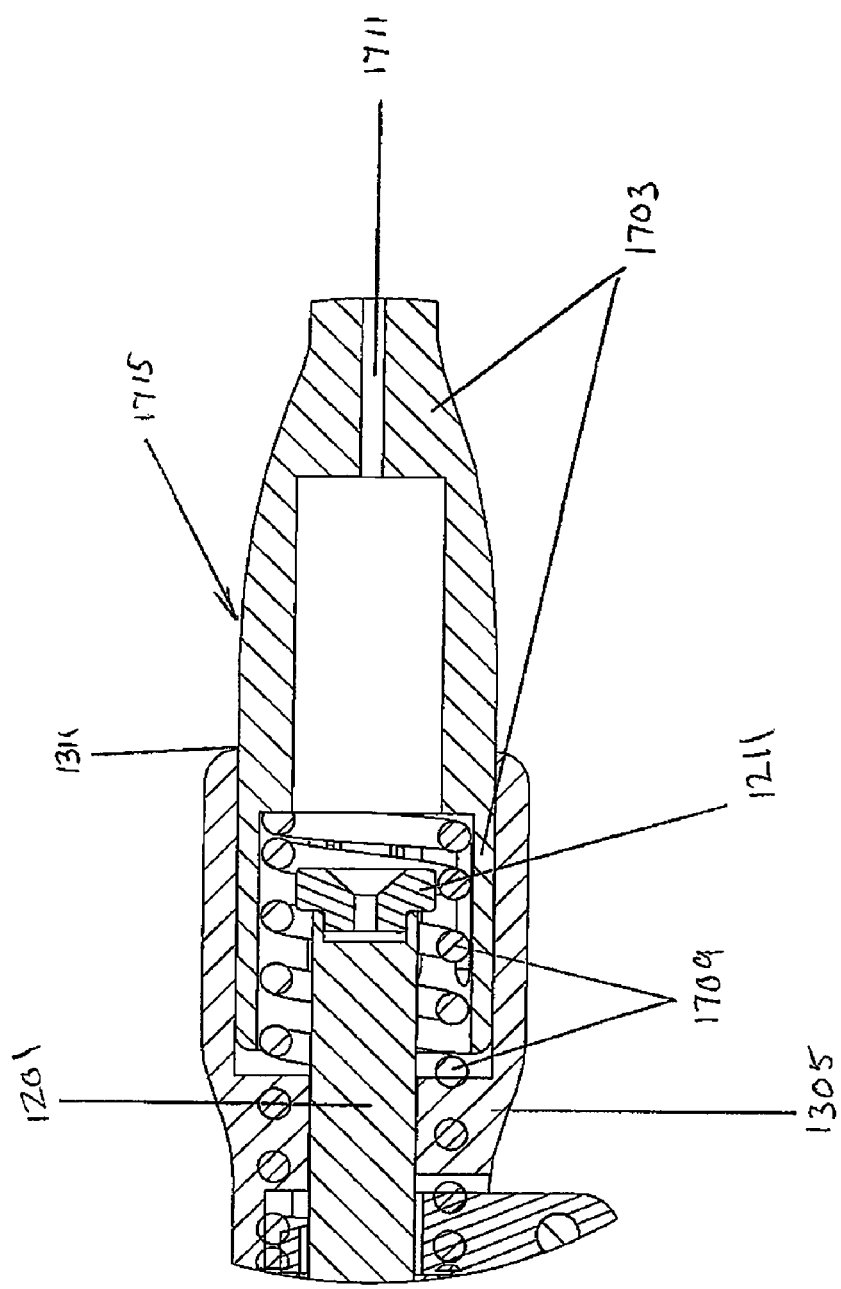
FIG. 17 is a detailed front sectional view of the tension indicator mechanism of the first embodiment of the pistol grip tensioning apparatus in the fully extended condition.

As indicated in FIGS. 16 and 17, the indicator top surface 1715 (or 2715) of the indicator structure 1703 has graduated markings in the form of laser etched lines and numbers indicating the amount of compression and corresponding tension in the surgical cable 12. When the housing structure edge 1311 matches a line and number on the indicator top surface 1715 during tensioning then that number will accurately indicate the tension on the surgical cable 12.

Again, the tension indicator mechanism 1701 for the first apparatus 1001 is substantially the same as the tension indicator mechanism 2701, 4701 for the second and fourth apparatuses 2001, 4001. The detailed description previously recited applies equally to those apparatuses 2001, 4001 and is not repeated.

However, the tension indicator 3701 for the third embodiments 3001 operates slightly differently. When the lever 3501 shifts because of the handle pin 3405, the calibrated compression spring 3709 then shifts in the distal direction to create mechanical compression of a calibrated compression spring 3709. The indicator mechanism 3701 is mechanically connected to the lever 3501 and is within the housing member 3301. When the lever 3501 is fully engaged the amount of tension can be read from markings on the indicator mechanism 3701 and the housing 3301. The tension indicator 3701 and housing 3301 for the third embodiments 3001 is an alternative means for measuring cable tension compared to the tension indicator and housing of the other embodiments.

Material Components and Manufacturing Techniques

The cable tensioning apparatus 1001, 2001, 3001 and 4001 can be made from any suitable, structurally strong material. The structural portions and other components are constructed of suitable materials which are compatible with the uses and environments into which the apparatus will be utilized. Preferably, the cable tensioning apparatus 1001, 2001, 3001 and 4001, is principally constructed of metallic materials such as 17-4 stainless steel, or 465 stainless steel.

As mentioned previously, the indicator structure and possibly some of the housing members are made of gall-resistant stainless steels such as Nitronic 60 or Gall-Tough. In addition, the calibrated compression spring 1709, 2709, 3709 and 4709 is made of stainless steel.

Alternatively, the exterior components can be made of other metal alloys such as titanium. In addition, the structural materials can also be chrome coated or plated to reduce galling, improved sterilization, for the reduction of friction and for cosmetic reasons. In yet other embodiments, medical lubricant or instrument milk can be added for improved lubrication and reduced friction.

The majority of the cable tensioning apparatus 1001, 2001, 3001 and 4001 is made using standard lathes and milling machines. Alternatively, other standard manufacturing processes such as metal casting can be use to make a majority of the components of the cable tensioning apparatus 1001, 2001, 3001 and 4001 as well. Wire Electrical Discharge Machining (or EDM) or spark machining is used to cut intricately shaped parts of the cable tensioning apparatus 1001, 2001, 3001 and 4001. EDM or spark machining is also used to cut the exotic metals of the cable tensioning apparatus 1001, 2001, 3001 and 4001 such as gall-resistant stainless steels such as Nitronic 60 or Gall-Tough. Welded components are preferably welded using laser welding and/or gas tungsten arc welding (GTAW), also known as tungsten inert gas (TIG) welding. Alternatively, other standard welding processes or epoxy can be used to connect some of the components of the cable tensioning apparatus 1001, 2001, 3001 and 4001.

The embodiments of this invention shown in the drawing and described above are exemplary of numerous embodiments that may be made within the scope of the appended claims. It is contemplated that numerous other configurations or conditions may be used, and the material of each component may be selected from numerous materials other than those specifically disclosed. In short, it is the applicant's intention that the scope of the patent issuing here from will be limited only by the scope of the appended claims.

What is claimed is:

1. A cable tensioning apparatus for generating tension in a cable, the cable tensioning apparatus comprising:
   an elongate shaft assembly having proximal and distal ends and a longitudinal axis extending therebetween;
   a proximal cable guide device mounted to the elongate shaft assembly;
   a distal cable guide device mounted to the elongate shaft assembly, longitudinally spaced from the proximal cable guide device;
   cable guideways of the proximal and distal cable guide devices that are aligned with and longitudinally spaced from each other and spaced from the elongate shaft assembly for receiving the cable therethrough, the distal cable guide device including a bridge portion extending above the shaft assembly for spacing the distal cable guideway from the shaft assembly;
   a clamping mechanism of the proximal cable guide device for clamping the cable relative to the proximal cable guide device;
   a plurality of detachable clamp mechanisms for connecting to an upper end portion of the bridge portion of the distal cable guide device to clamp the cable extending through the cable guideway,
   a detachable connection between the upper end portion of the bridge portion of the distal cable guide device and each of the plurality of clamp mechanisms so that with one of the plurality of clamp mechanisms attached to the bridge portion the clamp mechanism can be clamped on the cable and detached from the bridge portion to maintain tension in the cable so that another of the plurality of clamp mechanisms can be attached to the upper end portion of the bridge portion for tensioning another cable; and
   a drive mechanism housed in the shaft assembly and operable to shift the proximal cable guide device longitudinally in a proximal direction away from the shaft assembly distal end so that with the cable extending through the cable guideways and clamped to the proximal cable guide device, the longitudinally spaced proximal and distal cable guide devices allow an operator to observe tension develop in a length of cable exposed between the longitudinally spaced cable guide devices and spaced from the shaft assembly as the proximal cable guide device is shifted longitudinally in the proximal direction.

2. The cable tensioning apparatus of claim 1, wherein the shaft assembly includes a housing portion to which the distal cable guide device is mounted and a drive rod slidably connected to the housing portion to which the proximal cable guide device is mounted so that operation of the drive mechanism causes the drive rod to slide longitudinally in the proximal direction relative to the housing portion to shift the proximal cable guide device away from the distal cable guide device to generate tension in the cable.

3. The cable tensioning apparatus of claim 1, wherein the cable guideways each include a longitudinal throughbore each being longitudinally shorter than the longitudinal spacing between the cable guideways to allow for access for cleaning inner surfaces thereof.

4. The cable tensioning apparatus of claim 1, wherein the drive mechanism includes a lever actuator extending below the shaft assembly and pivotally connected thereto so that pivoting the lever operates the drive mechanism, and the cable guideways are spaced above the shaft assembly so that the length of cable exposed between the proximal and distal cable guide devices does not interfere with movement of the lever actuator.

5. The cable tensioning apparatus of claim 4, wherein the pivot connection between the lever actuator and the shaft assembly is positioned at an upper portion of the shaft assembly and below the cable guideways to optimize the mechanical advantage for pivoting the lever actuator without interfering with the exposed length of cable.

6. The cable tensioning apparatus of claim 1, wherein the drive mechanism includes a lever actuator, and
   a handle that depends from the shaft assembly configured to allow a user to shift the lever actuator toward the handle for operating the drive mechanism without grasping the shaft assembly.

7. The cable tensioning apparatus of claim 1, further comprising a releasable stop configured to allow the proximal cable guide device to shift in the proximal direction and to restrict the proximal cable guide device from shifting in the distal direction to maintain tension in the length of cable during tensioning thereof, and a release lever of the releasable stop pivotally connected to the shaft assembly and extending therebelow for being pivoted to release the releasable stop so that the proximal cable guide device can shift toward the distal cable guide device to reduce the tension in the length of cable.

8. The cable tensioning apparatus of claim 1, wherein the shaft assembly has a tension indicating mechanism including a proximal portion and a distal portion that is slidable relative to the proximal portion along the longitudinal axis and a resilient member mounted therebetween to bias the distal portion longitudinally away from the proximal portion so that shifting the proximal cable guide device in the proximal direction to develop tension in the cable causes the distal portion to shift in the proximal direction against the bias of the resilient member by a distance corresponding to the tension in the cable, and an indicator on one of the distal portion and the proximal portion to indicate the amount of tension in the cable.

* * * * *